US012595497B2

(12) United States Patent
Protzko

(10) Patent No.: US 12,595,497 B2
(45) **Date of Patent: *Apr. 7, 2026**

(54) PROCESSES FOR THE PRODUCTION OF TRYPTAMINES

(71) Applicant: Compass Pathfinder Limited, Altrincham (GB)

(72) Inventor: Ryan Protzko, Berkeley, CA (US)

(73) Assignee: Compass Pathfinder Limited, Altrincham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,790

(22) Filed: Apr. 17, 2023

(65) Prior Publication Data

US 2024/0084344 A1 Mar. 14, 2024

Related U.S. Application Data

(63) Continuation of application No. 17/012,737, filed on Sep. 4, 2020, now Pat. No. 11,661,617, which is a continuation of application No. PCT/US2019/021489, filed on Mar. 8, 2019.

(60) Provisional application No. 62/640,443, filed on Mar. 8, 2018.

(51) Int. Cl.

| | |
|---|---|
| ***C12P 17/10*** | (2006.01) |
| ***A61K 31/4045*** | (2006.01) |
| ***C07D 209/16*** | (2006.01) |
| ***C12N 9/02*** | (2006.01) |
| ***C12N 9/10*** | (2006.01) |
| ***C12N 9/12*** | (2006.01) |
| ***C12N 9/88*** | (2006.01) |
| ***C12N 9/90*** | (2006.01) |
| ***C12N 15/52*** | (2006.01) |

(52) U.S. Cl.

CPC .......... *C12P 17/10* (2013.01); *A61K 31/4045* (2013.01); *C07D 209/16* (2013.01); *C12N 9/0042* (2013.01); *C12N 9/0071* (2013.01); *C12N 9/0083* (2013.01); *C12N 9/1205* (2013.01); *C12N 9/88* (2013.01); *C12Y 106/02004* (2013.01); *C12Y 114/16004* (2013.01); *C12Y 114/99* (2013.01); *C12Y 207/01* (2013.01); *C12Y 401/01* (2013.01)

(58) Field of Classification Search

None

See application file for complete search history.

(56) References Cited

U.S. PATENT DOCUMENTS

| | | | |
|---|---|---|---|
| 3,075,992 | A | 1/1963 | Albert et al. |
| 6,447,784 | B1 | 9/2002 | Bermudes et al. |
| 11,136,293 | B2 | 10/2021 | Protzko |
| 2021/0108238 | A1 | 4/2021 | Protzko |
| 2021/0147888 | A1 | 5/2021 | Vogan et al. |

FOREIGN PATENT DOCUMENTS

| | | | |
|---|---|---|---|
| CN | 101283089 | A | 10/2008 |
| CN | 106414755 | A | 2/2017 |
| WO | WO-9534657 | A2 | 12/1995 |
| WO | WO-02079153 | A1 | 10/2002 |
| WO | WO-2013085922 | A1 | 6/2013 |
| WO | WO-2013127915 | A1 | 9/2013 |
| WO | WO-2015032911 | A1 | 3/2015 |
| WO | WO-2017123418 | A1 | 7/2017 |
| WO | WO-2019173797 | A1 | 9/2019 |
| WO | WO-2019180309 | A1 | 9/2019 |
| WO | WO-2021086513 | A1 | 5/2021 |

OTHER PUBLICATIONS

Mahmood, "Bioactive Alkaloids from Fungi: Psilocybin," Natural Products, pp. 523-552 (May 31, 2013).

Adams et al. In vivo production of psilocybin in *E. coli.* Metabolic Engineering 56:111-119 (2019). Available online Sep. 21, 2019.

Blaschko et al. A comparative study of hydroxyindole oxidases. Br J Pharmacol Chemother. Dec. 1960; 15(4): 625-633.

Carbonaro et al. Neuropharmacology of N,N-Dimethyltryptamine. Brain Res Bull. Sep. 2016; 126(Pt 1): 74-88. Published online Apr. 25, 2016. doi: 10.1016/j.brainresbull.2016.04.016.

Carrier, M.I., et al., Expression of Human IL-1B in *Salmonella typhimurium* a Model System for the Delivery of Recombinant Therapeutic Proteins in Vivo, The Journal of Immunology, 1992, pp. 1176-1181, vol. 148, No. 4, The American Association of Immunologists.

CAS Registry No. 1373882-09-7; entered STN database on May 16, 2012, 1 page.

CB Therapeutics Achieves Major Breakthrough in the Biosynthesis of Psilocybin, Psilocin and Related Tryptamine-based Compounds. Business Wire (Dec. 4, 2019). 2 pages.

Datsenko and Wanner, "One-step inactivation of chromosomal genes in *Escherichia coli* K-12 using PCR products". PNAS (Jun. 6, 2000); 97(12): 6640-6645.

Deloache et al. An enzyme-coupled biosensor enables (S)-reticuline production in yeast from glucose. Nat Chem Biol. Jul. 2015;11(7):465-471.doi: 10.1038/nchembio.1816. Epub May 18, 2015.

(Continued)

*Primary Examiner* — Suzanne M Noakes
*Assistant Examiner* — Jae W Lee
(74) *Attorney, Agent, or Firm* — COOLEY LLP

(57) ABSTRACT

Disclosed herein are prokaryotic and eukaryotic microbes, including *E. coli* and *S. cerevisiae*, genetically altered to biosynthesize tryptamine and tryptamine derivatives. The microbes of the disclosure may be engineered to contain plasmids and stable gene integrations containing sufficient genetic information for conversion of an anthranilate or an indole to a tryptamine. The fermentative production of substituted tryptamines in a whole-cell biocatalyst may be useful for cost effective production of these compounds for therapeutic use.

11 Claims, 19 Drawing Sheets

Specification includes a Sequence Listing.

(56) References Cited

OTHER PUBLICATIONS

Derry et al. Sumatriptan (all routes of administration) for acute migraine attacks in adults—overview of Cochrane reviews. Cochrane Database Syst Rev. May 2014; 2014(5):CD009108. Published online May 27, 2014. doi: 10.1002/14651858.CD009108.pub2, 69 pages.
Fricke et al. Enzymatic Route toward 6-Methylated Baeocystin and Psilocybin. Chembiochem. Nov. 18, 2019;20(22):2824-2829.doi: 10.1002/cbic.201900358. Epub Oct. 17, 2019.
Fricke et al. Production Options for Psilocybin: Making of the Magic. Chem. Eur. J. 2019, 25, 897-903. First published: Jul. 16, 2018. DOI: https://doi.org/10.1002/chem.201802758.
Fricke J., et al. Enzymatic Synthesis of Psilocybin, Angewandte Chemie, Sep. 2017, vol. 56(40), pp. 12352-12355.
Gartz et al. Ethnomycology, biochemistry, and cultivation of Psilocybe samuiensis Guzmán, Bandala and Allen, a new psychoactive fungus from Koh Samui, Thailand. J Ethnopharmacol. Jul. 8, 1994;43(2):73-80. doi: 10.1016/0378-8741(94)90006-x.
Gartz, J. Extraction and analysis of indole derivatives from fungal biomass. J Basic Microbiol. 1994;34(1):17-22.doi: 10.1002/jobm.3620340104.
Griffiths, R.R. et al. (Aug. 2006) Psilocybin can occasion mystical-type experiences having substantial and sustained meaning and spiritual significance. Psychopharmacol (Berl), 187(3):268-283.
Hanson et al. Codon optimality, bias and usage in translation and mRNA decay. Nat Rev Mol Cell Biol. Jan. 2018; 19(1): 20-30. Published online Oct. 11, 2017. doi: 10.1038/nrm.2017.91.
Hasler, F. et al. (Mar. 2004) Acute psychological and physiological effects of psilocybin in healthy humans: A double-blind, placebo-controlled dose-effect study. Psychopharmacology, 172(2):145-156.
Hoefgen et al. Facile assembly and fluorescence-based screening method for heterologous expression of biosynthetic pathways in fungi. Metabolic Engineering 48(2018):44-51 (May 26, 2018).
Hofmann, A. et al. (1959) "Psilocybin und Psilocin, zwei psychotrope Wirkstoffe aus mexikanischen Rauschpilzen [Psilocybin and Psilocin, two psychotropic active substances from Mexican magic mushrooms" Helvetica Chimica Acta, vol. XLII, Issue v, No. 168, pp. 1557-1572, with English translation (17 pages).
Hofmann, A. et al. (Nov. 1958) "Konstitutionsaufklärung und Synthese von Psilocybin [Constitutional elucidation and synthesis of psilocybin]" Experientia, 14(11):397-399, with English translation (3 pages).
Kelly, J.R., et al. "Measuring the activity of BioBrick promoters using an in vivo reference standard". J Biol Eng. (2009). 3:4. 13 pages.
Lenz et al. Identification of ω-N-Methyl-4-hydroxytryptamine (Norpsilocin) as a Psilocybe Natural Product. J Nat Prod. Oct. 27, 2017;80(10):2835-2838.doi: 10.1021/acs.jnatprod.7b00407. Epub Sep. 20, 2017.
Milne et al., "Metabolic engineering of *Saccharomyces cerevisiae* for the de novo production of psilocybin and related tryptamine derivatives," Metabolic Engineering 60 (2020) 25-36.
Moreno, F.A. et al. (Nov. 2006). Safety, tolerability, and efficacy of psilocybin in 9 patients with obsessive-compulsive disorder. Journal of Clinical Psychiatry, 67(11), 1735-1740. https://doi.org/10.4088/JCP.v67n1110.
Nichols, David E. The Heffter Research Institute: past and hopeful future. J Psychoactive Drugs. Jan.-Mar. 2014;46(1):20-26.doi: 10.1080/02791072.2014.873688.
Park et al. Production of serotonin by dual expression of tryptophan decarboxylase and tryptamine 5-hydroxylase in *Escherichia coli*. Appl Microbiol Biotechnol. Mar. 2011;89(5):1387-1394. doi: 10.1007/s00253-010-2994-4. Epub Nov. 16, 2010.
PCT/US2019/021489 International Search Report and Written Opinion dated May 24, 2019, 19 pages.
Quax, et al., "Codon Bias as a Means to Fine-Tune Gene Expression." Mol Cell (2015); 59(2): 149-161.
Sizemore, et al. Attenuated Shigella as a DNA delivery vehicle for DNA-mediated immunization. Science. Oct. 13, 1995;270(5234):299-302.

| Fed compound | induced bNAB003 culture | induced bNAB004 culture |
| --- | --- | --- |
| 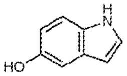 5-hydroxyindole | 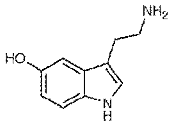 5-hydroxytryptamine | 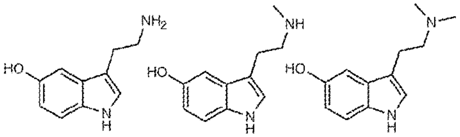 5-hydroxytryptamine; 5-hydroxymethyl tryptamine; 5-hydroxy *N,N*-dimethyltryptamine |
| 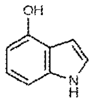 4-hydroxyindole | 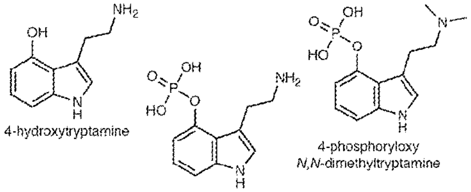 4-hydroxytryptamine; 4-phosphoryloxytryptamine; 4-phosphoryloxy *N,N*-dimethyltryptamine | Not tested |
| 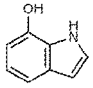 7-hydroxyindole | 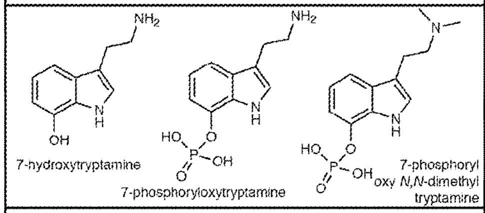 7-hydroxytryptamine; 7-phosphoryloxytryptamine; 7-phosphoryl oxy *N,N*-dimethyl tryptamine | Not tested |
| 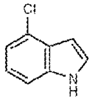 4-chloroindole | 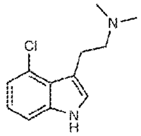 4-chloro *N,N*-dimethyltryptamine | 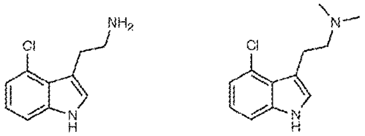 4-chlorotryptamine; 4-chloro *N,N*-dimethyltryptamine |
| 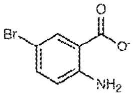 5-bromoanthranilate | Not tested | 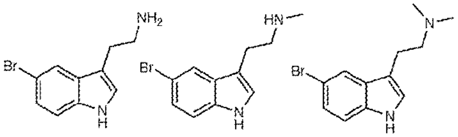 5-bromotryptamine; 5-bromo-*N*-methyltryptamine; 5-bromo-*N,N*-dimethyltryptamine |

FIG. 4

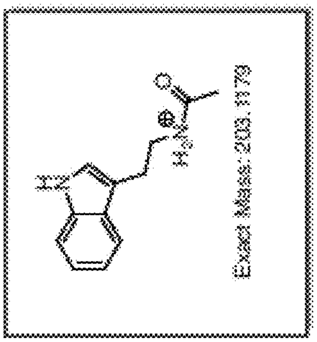
Exact Mass: 203.1179
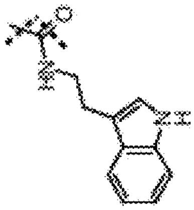
159.0917
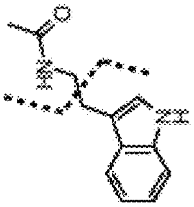
130.0651
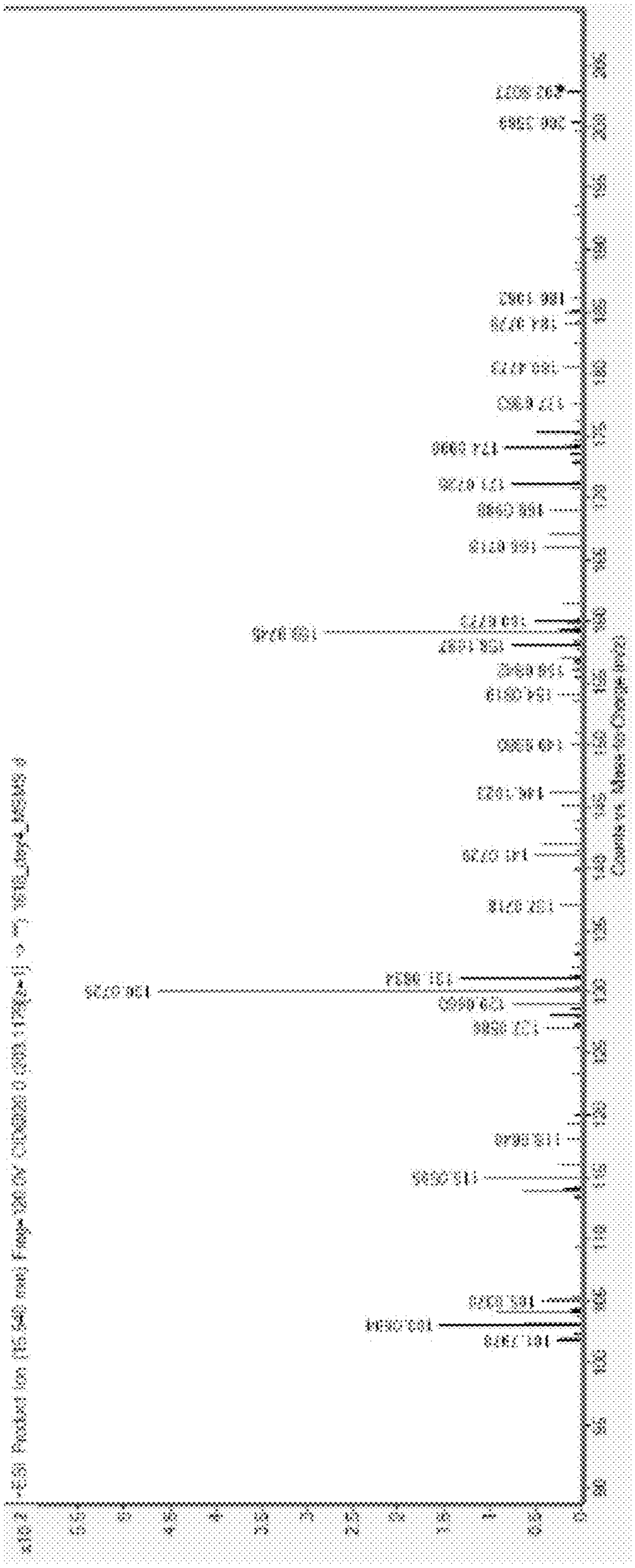
FIG. 11

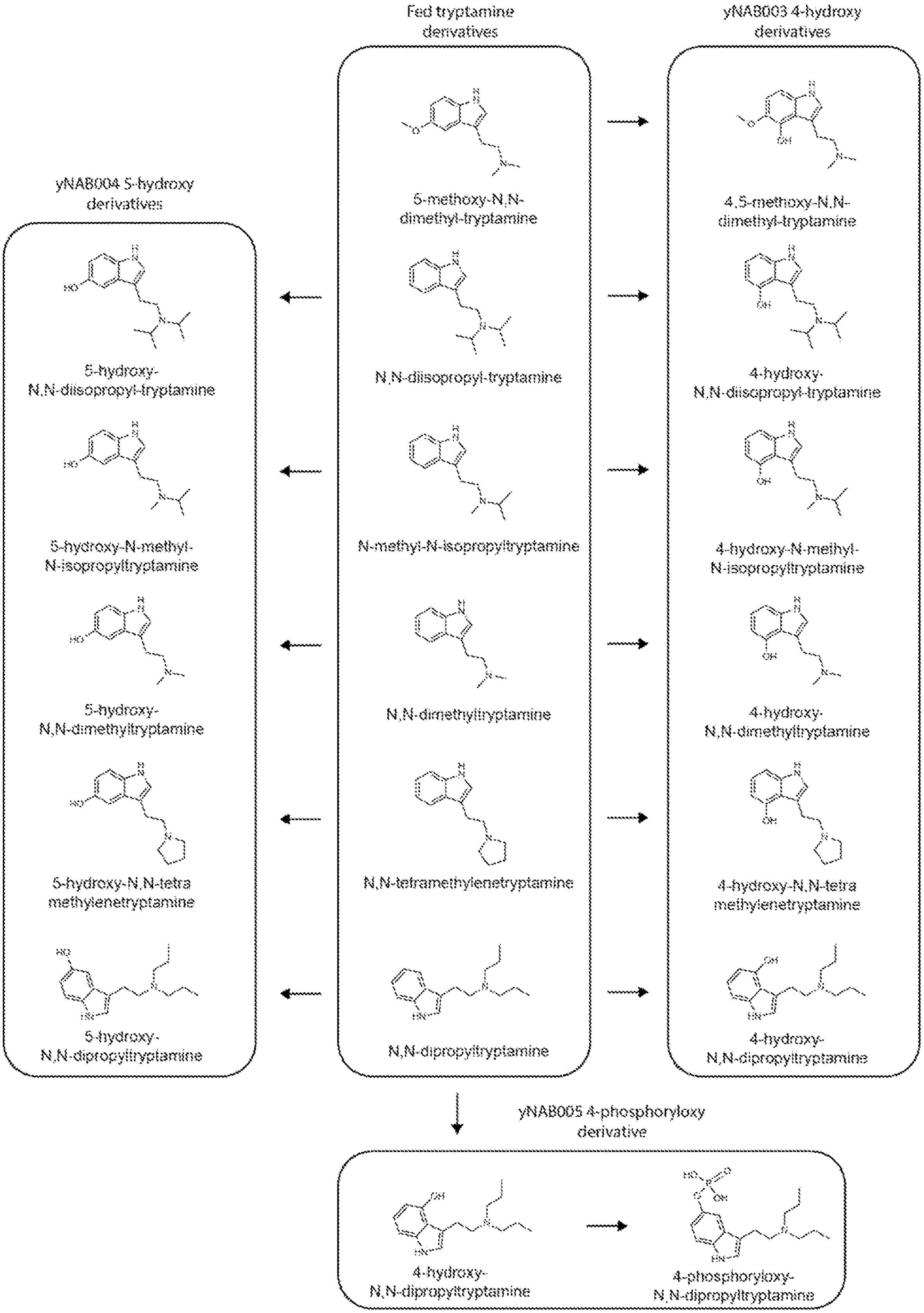

5-methoxy-N,N-dimethyl-tryptamine 4,5-methoxy-N,N-dimethyl-tryptamine 5-hydroxy-N,N-diisopropyl-tryptamine N,N-diisopropyl-tryptamine 4-hydroxy-N,N-diisopropyl-tryptamine 5-hydroxy-N-methyl-N-isopropyltryptamine N-methyl-N-isopropyltryptamine 4-hydroxy-N-methyl-N-isopropyltryptamine 5-hydroxy-N,N-dimethyltryptamine N,N-dimethyltryptamine 4-hydroxy-N,N-dimethyltryptamine 5-hydroxy-N,N-tetra methylenetryptamine N,N-tetramethylenetryptamine 4-hydroxy-N,N-tetra methylenetryptamine 5-hydroxy-N,N-dipropyltryptamine N,N-dipropyltryptamine 4-hydroxy-N,N-dipropyltryptamine 4-hydroxy-N,N-dipropyltryptamine 4-phosphoryloxy-N,N-dipropyltryptamine

FIG. 16 tryptamine 4-hydroxytryptamine

L-tryptophan 4-hydroxy-L-tryptophan

A.

B.

ibogamine 5-hydroxyibogamine 5-methoxyibogamine 5-phosphoryloxyibogamine 4-hydroxyibogamine 4-methoxyibogamine 4-phosphoryloxyibogamine

SEQUENCE LISTING

```
Sequence total quantity: 49
SEQ ID NO: 1            moltype = DNA  length = 4969
FEATURE                 Location/Qualifiers
source                  1..4969
                        mol_type = genomic DNA
                        organism = Escherichia coli
SEQUENCE: 1
atggctgaca ttctgctgct cgataatatc gactctttta cgtacaacct ggcagatcag  60
ttgcgcagca atgggcataa cgtggtgatt taccgcaacc atattccggc gcaaacctta  120
attgaacgcc tggcgaccat gagcaatccg gtgctgatgc tttctcctgg ccccggtgtg  180
ccgagcgaag ccggttgtat gccggaactc ctcacccgct tgcgtggcaa gctgcccatt  240
attggcattt gcctcggaca tcaggcgatt gtcgaagctt acgggggcta tgtcggtcag  300
gcgggcgaaa ttctccacgg taaagcctcc agcattgaac atgacggtca ggcgatgttt  360
gccggattaa caaacccgct gccggtggcg cgttatcact cgctggttgg cagtaacatt  420
ccggccggtt taaccatcaa cgcccatttt aatggcatgg tgatggcagt acgtcacgat  480
gcggatcgcg tttgtggatt ccagttccat ccggaatcca ttctcaccac ccagggcgct  540
cgcctgctgg aacaaacgct ggcctgggcg cagcagaaac tagagccagc caacacgctg  600
caaccgattc tggaaaaact gtatcaggcg cagacgctta gccaacaaga aagccaccag  660
ctgttttcag cggtggtgcg tggcgagctg aagccggaac aactggcggc ggcgctggtg  720
agcatgaaaa ttcgcggtga gcacccgaac gagatcgccg gggcagcaac cgcgctactg  780
gaaaacgcag cgccgttccc gcgcccggat tatctgtttg ctgatatcgt cggtactggc  840
ggtgacggca gcaacagtat caatatttct accgccagtg cgtttgtcgc cgcggcctgt  900
gggctgaaag tggcgaaaca cggcaaccgt agcgtctcca gtaaatctgg ttcgtccgat  960
ctgctggcgg cgttcggtat taatcttgat atgaacgccg ataaatcgcg ccaggcgctg  1020
gatgagttag gtgtatgttt cctctttgcg ccgaagtatc acaccggatt ccgccacgcg  1080
atgccggttc gccagcaact gaaaacccgc accctgttca atgtgctggg gccattgatt  1140
aacccggcgc atccgccgct ggcgttaatt ggtgtttata gtccggaact ggtgctgccg  1200
attgccgaaa ccttgcgcgt gctggggtat caacgcgcgg cggtggtgca cagcggcggg  1260
atggatgaag tttcattaca cgcgccgaca atcgttgccg aactgcatga cggcgaaatt  1320
aaaagctatc agctcaccgc agaagacttt ggcctgacac cctaccacca ggagcaactg  1380
gcaggcggaa caccggaaga aaaccgtgac attttaacac gtttgttaca aggtaaaggc  1440
gacgccgccc atgaagcagc cgtcgctgcg aacgtcgcca tgttaatgcg cctgcatggc  1500
catgaagatc tgcaagccaa tgcgcaaacc gttcttgagg tactgcgcag tggttccgct  1560
tacgacagag tcaccgcact ggcggcacga gggtaaatga tgcaaaccgt tttagcgaaa  1620
atcgtcgcag acaaggcgat ttgggtagaa gcccgcaaac agcagcaacc gctggccagt  1680
tttcagaatg aggttcagcc gagcacgcga catttttatg atgcgctaca gggtgcgcgc  1740
acggcgttta ttctggagtg caagaaagcg tcgccgtcaa aaggcgtgat ccgtgatgat  1800
ttcgatccag cacgcattgc cgccatttat aaacattacg cttcggcaat ttcggtgctg  1860
actgatgaga aatattttca ggggagcttt aatttcctcc ccatcgtcag ccaaatcgcc  1920
ccgcagccga ttttatgtaa agacttcatt atcgaccctt accagatcta tctggcgcgc  1980
tattaccagg ccgatgcctg cttattaatg ctttcagtac tggatgacga ccaatatcgc  2040
cagcttgccg ccgtcgctca cagtctggag atgggggtgc tgaccgaagt cagtaatgaa  2100
gaggaacagg agcgcgccat tgcattggga gcaaaggtcg ttggcatcaa caaccgcgat  2160
ctgcgtgatt tgtcgattga tctcaaccgt acccgcgagc ttgcgccgaa actggggcac  2220
aacgtgacgg taatcagcga atccggcatc aatacttacg ctcaggtgcg cgagttaagc  2280
cacttcgcta acggttttct gattggttcg gcgttgatgg cccatgacga tttgcacgcc  2340
gccgtgcgcc gggtgttgct gggtgagaat aaagtatgtg gcctgacgcg tgggcaagat  2400
gctaaagcag cttatgacgc gggcgcgatt tacggtgggt tgatttttgt tgcgacatca  2460
ccgcgttgcg tcaacgttga acaggcgcag gaagtgatgg ctgcggcacc gttgcagtat  2520
gttggcgtgt tccgcaatca cgatattgcc gatgtggtgg acaaagctaa ggtgttatcg  2580
```

-continued

```
ctggcggcag tgcaactgca tggtaatgaa gaacagctgt atatcgatac gctgcgtgaa  2640
gctctgccag cacatgttgc catctggaaa gcattaagcg tcggtgaaac cctgcccgcc  2700
cgcgagtttc agcacgttga taaatatgtt ttagacaacg gccagggtgg aagcgggcaa  2760
cgttttgact ggtcactatt aaatggtcaa tcgcttggca acgttctgct ggcgggggc  2820
ttaggcgcag ataactgcgt ggaagcggca caaaccggct gcgccggact tgattttaat  2880
tctgctgtag agtcgcaacc gggcatcaaa gacgcacgtc ttttggcctc ggttttccag  2940
acgctgcgcg catattaagg aaaggaacaa tgacaacatt acttaacccc tattttggtg  3000
agtttggcgg catgtacgtg ccacaaatcc tgatgcctgc tctgcgccag ctggaagaag  3060
cttttgtcag tgcgcaaaaa gatcctgaat ttcaggctca gttcaacgac ctgctgaaaa  3120
actatgccgg gcgtccaacc gcgctgacca aatgccagaa cattacagcc gggacgaaca  3180
ccacgctgta tctcaagcgt gaagatttgc tgcacggcgg cgcgcataaa actaaccagg  3240
tgctggggca ggcgttgctg gcgaagcgga tgggtaaaac cgaaatcatc gccgaaaccg  3300
gtgccggtca gcatggcgtg gcgtcggccc ttgccagcgc cctgctcggc ctgaaatgcc  3360
gtatttatat gggtgccaaa gacgttgaac gccagtcgcc taacgttttt cgtatgcgct  3420
taatgggtgc ggaagtgatc ccggtgcata gcggttccgc gacgctgaaa gatgcctgta  3480
acgaggcgct gcgcgactgg tccggtagtt acgaaaccgc gcactatatg ctgggcaccg  3540
cagctggccc gcatccttat ccgaccattg tgcgtgagtt tcagcggatg attggcgaag  3600
aaaccaaagc gcagattctg gaaagagaag gtcgcctgcc ggatgccgtt atcgcctgtg  3660
ttggcggcgg ttcgaatgcc atcggcatgt ttgctgattt catcaatgaa accaacgtcg  3720
gcctgattgg tgtggagcca ggtggtcacg gtatcgaaac tggcgagcac ggcgcaccgc  3780
taaaacatgg tcgcgtgggt atctatttcg gtatgaaagc gccgatgatg caaaccgaag  3840
acgggcagat tgaagaatct tactccatct ccgccggact ggatttcccg tctgtcggcc  3900
cacaacacgc gtatcttaac agcactggac gcgctgatta cgtgtctatt accgatgatg  3960
aagcccttga agccttcaaa acgctgtgcc tgcacgaagg gatcatcccg gcgctggaat  4020
cctcccacgc cctggcccat gcgttgaaaa tgatgcgcga aaacccggat aaagagcagc  4080
tactggtggt taacctttcc ggtcgcggcg ataaagacat cttcaccgtt cacgatattt  4140
tgaaagcacg aggggaaatc tgatggaacg ctacgaatct ctgtttgccc agttgaagga  4200
gcgcaaagaa ggcgcattcg ttcctttcgt cacgctcggt gatccgggca ttgagcagtc  4260
attgaaaatt atcgatacgc taattgaagc cggtgctgac gcgctggagt taggtatccc  4320
cttctccgac ccactggcgg atggcccgac gattcaaaac gccactctgc gcgcctttgc  4380
ggcaggtgtg actccggcac aatgttttga aatgctggca ctgattcgcc agaaacaccc  4440
gaccattccc attggcctgt tgatgtatgc caatctggtg tttaacaaag gcattgatga  4500
gttttatgcc cagtgcgaaa aagtcggcgt cgattcggtg ctggttgccg atgtgccagt  4560
tgaagagtcc gcgcccttcc gccaggccgc gttgcgtcat aatgtcgcac ctatcttcat  4620
ctgcccgcca aatgccgatg acgacctgct gcgccagata gcctcttacg gtcgtggtta  4680
cacctatttg ctgtcacgag caggcgtgac cggcgcagaa aaccgcgccg cgttacccct  4740
caatcatctg gttgcgaagc tgaaagagta caacgctgca cctccattgc agggatttgg  4800
tatttccgcc ccggatcagg taaaagcagc gattgatgca ggagctgcgg gcgcgatttc  4860
tggttcggcc attgttaaaa tcatcgagca acatattaat gagccagaga aaatgctggc  4920
ggcactgaaa gtttttgtac aaccgatgaa agcggcgacg cgcagttaa              4969

SEQ ID NO: 2           moltype = DNA  length = 4390
FEATURE                Location/Qualifiers
source                 1..4390
                       mol_type = genomic DNA
                       organism = Bacillus subtilis
SEQUENCE: 2
atgaacagat ttctacaatt gtgcgttgac ggaaaaaccc ttactgccgg tgaggctgaa  60
acgctgatga atatgatgat ggcagcggaa atgactcctt ctgaaatggg ggggatattg  120
tcaattcttg ctcatcgggg ggagacgcca gaagagcttg cgggttttgt gaaggcaatg  180
cgggcacacg ctcttacagt cgatggactt cctgatattg ttgatacatg cggaacaggg  240
ggagacggta tttccacttt taatatctca acggcctcgg caattgttgc ctcggcagct  300
ggtgcgaaaa tcgctaagca tggcaatcgc tctgtctctt ctaaaagcgg aagcgctgat  360
gttttagagg agctagaggt ttctattcaa accactcccg aaaaggtcaa aagcagcatt  420
gaaacaaaca acatgggatt tctttttgcg ccgctttacc attcgtctat gaaacatgta  480
gcaggtacta gaaaagagct aggtttcaga acggtattta atctgcttgg gccgctcagc  540
aatcctttac aggcgaagcg tcaggtgatt ggggtctatt ctgttgaaaa agctggactg  600
atggcaagcg cactggagac gtttcagccg aagcacgtta tgtttgtatc aagccgtgac  660
ggtttagatg agctttcaat tacagcaccg accgacgtga ttgaattaaa ggacggagag  720
cgccgggagt ataccgtttc acccgaagat ttcggtttca caaatggcag acttgaagat  780
ttacaggtgc agtctccgaa agagagcgct tatctcattc agaatatttt tgaaaataaa  840
agcagcagtt ccgctttatc tattacggct tttaatgcgg gtgctgcgat ttacacggcg  900
ggaattaccg cctcactgaa ggaaggaacg gagctggcgt tagagacgat tacaagcgga  960
ggcgctgccg cgcagcttga acgactaaag cagaaagagg aagagatcta tgcttgaaaa  1020
aatcatcaaa caaaagaaag aagaagtgaa aacactggtt ctgccggtag agcagccttt  1080
cgagaaacgt tcatttaagg aggcgctggc aagcccgaat cggtttatcg ggttgattgc  1140
cgaagtgaag aaagcatcgc cgtcaaaagg gcttattaaa gaggattttg tacctgtgca  1200
gattgcaaaa gactatgagg ctgcgaaggc agatgcgatt tccgttttaa cagacacccc  1260
gtttttttcaa ggggaaaaca gctatttatc agacgtaaag cgtgctgttt cgattcctgt  1320
acttagaaaa gattttattg attctcttca agtagaggaa tcaagaagaa tcggagcgga  1380
tgccatattg ttaatcggcg aggtgcttga tcccttacac cttcatgaat tatatcttga  1440
agcaggtgaa aaggggatgg acgtgttagt ggaggttcat gatgcatcaa cgctagaaca  1500
aatattgaaa gtgttcacac ccgacattct cggcgtaaat aatcgaaacc taaaaacgtt  1560
tgaaacatct gtaaagcaga cagaacaaat cgcatctctc gttccgaaag aatccttgct  1620
tgtcagcgaa agcggaatcg gttctttaga acatttaaca tttgtcaatg aacatggggc  1680
gcgagctgta cttatcggtg aatcattgat gagacaaact tctcagcgta aagcaatcca  1740
tgctttgttt agggagtgag gttgtgaaga aaccggcatt aaaatattgc ggtattcggt  1800
cactaaagga tttgcagctt gcggcggaat cacaggctga ttacctagga tttatttttg  1860
ctgaaagcaa acgaaaagta tctccggaag atgtgaaaaa atggctgaac caagttcgtg  1920
```

-continued

```
tcgaaaaaca ggttgcaggt gtttttgtta atgaatcaat agagacgatg tcacgtattg  1980
ccaagagctt gaagctcgac gtcattcagc ttcacggtga tgaaaaaccg gcggatgctg  2040
ctgctcttcg caagctgaca ggctgtgaaa tatggaaggc gcttcaccat caagataaca  2100
caactcaaga aatagcccgc tttaaagata atgttgacgg ctttgtgatt gattcatctg  2160
taaaagggtc tagaggcgga actggtgttg cattttcttg ggaatgtgtg ccggaatatc  2220
agcaggcggc tattggtaaa cgctgcttta tcgctggcgg cgtgaatccg gatagcatca  2280
cacgcctatt gaaatggcag ccagaaggaa ttgaccttgc cagcggaatt gaaaaaaacg  2340
gacaaaaaga tcagaatctg atgaggcttt tagaagaaag gatgaaccga tatgtatcca  2400
tatccgaatg aaataggcag atacggtgat tttggcggaa agtttgttcc ggaaacactc  2460
atgcagccgt tagatgaaat acaaacagca tttaaacaaa tcaaggatga tcccgctttt  2520
cgtgaagagt attataagct gttaaaggac tattccggac gcccgactgc attaacatac  2580
gctgatcgag tcactgaata cttaggcggc gcgaaaatct atttgaaacg agaagattta  2640
aaccatacag gttctcataa aatcaataat gcgctaggtc aagcgctgct tgctaaaaaa  2700
atgggcaaaa cgaaaatcat tgctgaaacc ggtgccggcc agcatggtgt tgccgctgca  2760
acagttgcag ccaaattcgg ctttcctgt actgtgttta tgggtgaaga ggatgttgcc  2820
cgccagtctc tgaacgtttt ccgcatgaag cttcttggag cggaggtagt gcctgtaaca  2880
agcggaaacg gaacattgaa ggatgccaca aatgaggcga tccggtactg ggttcagcat  2940
tgtgaggatc acttttatat gattggatca gttgtcggcc cgcatcctta tccgcaagtg  3000
gtccgtgaat ttcaaaaaat gatcggagag gaagcgaagg atcagttgaa acgtattgaa  3060
ggcactatgc ctgataaagt agtggcatgt gtaggcggag gaagcaatgc gatgggtatg  3120
tttcaggcat ttttaaatga agatgttgaa ctgatcggcg ctgaagcagc aggaaaagga  3180
attgatacac ctcttcatgc cgccactatt tcgaaaggaa ccgtaggggt tattcacggt  3240
tcattgactt atctcattca ggatgagttc gggcaaatta ttgagcccta ctctatttca  3300
gccggtctcg actatcctgg aatcggtccg gagcatgcat atttgcataa aagcggccgt  3360
gtcacttatg acagtataac cgatgaagaa gcggtggatg cattaaagct tttgtcagaa  3420
aaagagggga ttttgccggc aatcgaatct gcccatgcgt tagcgaaagc attcaaactc  3480
gccaaaggaa tggatcgcgg tcaactcatt ctcgtctgtt tatcaggccg gggagacaag  3540
gatgtcaaca cattaatgaa tgtattggaa gaagaggtga aagcccatgt ttaaattgga  3600
tcttcaacca tcagaaaaat tgtttatccc gtttattacg gcgggcgatc cagttcctga  3660
ggtttcgatt gaactggcga agtcactcca aaaagcaggc gccacagcat tggagcttgg  3720
tgttgcatac tctgacccgc ttgcagacgg tccggtgatc cagcgggctt caaagcgggc  3780
gcttgatcaa ggaatgaata tcgtaaaggc aatcgaatta ggcggagaaa tgaaaaaaaa  3840
cggagtgaat attccgatta tcctctttac gtattataat cctgtgttac aattgaacaa  3900
agaatacttt ttcgctttac tgcgggaaaa tcatattgac ggtctgcttg ttccggatct  3960
gccattagaa gaaagcaaca gccttcaaga ggaatgtaaa agccatgagg tgacgtatat  4020
ttctttagtt gcgccgacaa gcgaaagccg tttgaaaacc attattgaac aagccgaggg  4080
gttcgtctac tgtgtatctt ctctgggtgt gaccggtgtc cgcaatgagt tcaattcatc  4140
cgtgtacccg ttcattcgta ctgtgaagaa tctcagcact gttccggttg ctgtagggtt  4200
cggtatatca aaccgtgaac aggtcataaa gatgaatgaa attagtgacg gtgtcgtagt  4260
gggaagtgcg ctcgtcagaa aaatagaaga attaaaggac cggctcatca gcgctgaaac  4320
gagaaatcag gcgctgcagg agtttgagga ttatgcaatg gcgtttagcg gcttgtacag  4380
tttaaaatga                                                         4390

SEQ ID NO: 3            moltype = DNA  length = 5467
FEATURE                 Location/Qualifiers
source                  1..5467
                        mol_type = genomic DNA
                        organism = Lactococcus lactis
SEQUENCE: 3
atgaaaacaa ggagtcatca aatgaaaaat gaacttgaaa aagtgatgtc aggtcgtgac  60
atgaccgaaa atgaaatgaa tatgcttgct aattcaatta tccaaggtga attaagcgag  120
gtccaaattg ccagcttttt agtagcatta aaaatgaaag gtgaagcagc aagcgaattg  180
actggtttgg ctcgagcttt acaaaaagca gcgattccca ttccaacaaa tttgacaaat  240
gcgatggaca attgtggaac aggaggcgac cgctcattca gttttaatat ttcaaccaca  300
gccgcttttg ttttagcagc tggtggagtc aatatggcaa aacacggaaa tcgctccatt  360
accagtaaat ctggctcggc agacgttctt gaggccttag gaatcaatct ttatttacca  420
gcagaaaagt tagctcaagt tttgacaaa gttggtttag ttttcctttt tgctcaaaat  480
ctccacccag cgatgaaata cttcacgcca gtccgcagac aactcgaaat tccaacaatt  540
atgaacttga ctgggccact aatcaatcca attccacttg atacgcaact tcttggtacc  600
tcacgtccag atttacttga attaacagca aatgttttga aaggcttggg ccgtaagcga  660
gcattagtca tcacaggtga aggcggaatg gacgaagcaa ctccctttgg acttaatcat  720
tacgcacttt tagaaaatga caaagtgact ttgcatgaat ttagagcctc agaagttggt  780
atttcagaag ttcaactcaa tgatattcgt ggaggtgaag ccccagaaaa tgctgaaatt  840
ttaaaaaatg tccttgaaaa tcaaccgtca gcctttttag aaacgaccgt tttaaatgcc  900
ggacttggat tttatgccaa tggaaaagtt gattccatca aatccggagt tgaccttgca  960
agagaagtaa ttagtacagg agcagctctt accaagttgc atgaattaca agcagaacaa  1020
attggttaaa aatcttgatg gcaaattttg aaatagcaga aaatgagaga aaaatatgaa  1080
cataaaaaaa ggaaaatttc tagaaacaat cctagcagaa aaacgacttg aaattgctaa  1140
aatgccagaa gaacaagtag gaaaagttcg tcaaacatac aatttttatg attacttaaa  1200
agaacattcc gaccagcttc aagtgattgc cgaagtcaaa aaagcttcgc ccagtctagg  1260
tgatattaac ttagaagtgg atatcgttga ccaagccaaa aattacgaac aagccggtgc  1320
cgctatgatt tccgtcttaa ctgaccctgt atttttaaa ggaaatattg aatatctctg  1380
tgaaatttca gaaaatgtcc aaatccccac cttgaacaag gattttatca tcgataaaaa  1440
acaaatcaat cgggcagtta atgcgggagc aacagttatt ttactcattg tcgcagtttt  1500
tgaaaatcaa taccccaaac tccaaaacct ctacaactac gcactttcac taggacttga  1560
agttcttgtt gaaacacata ataaagcaga acttgagatt gctcatcagc ttggagctaa  1620
aattattgga gttaataatc gtaatttaaa aacctttgaa gtgatcttac aaaattcagt  1680
agatttgaca ccctacttta aagaagacag tatctacatt tccgaatcag gcatttttag  1740
cgcaaacgaa gcccaaaaag tttccgatac tttcaatgga atattggttg gaacagcact  1800
```

-continued

```
catgcaatca gaaaatctag aaaaatcttt gaaagattta aaagtcaaga ggaaaacgaa  1860
tgaaaattaa aatctgtggc ttatctacaa aagaagctgt tgatacagct gtagaatctg  1920
gtgtcacaca tctcggtttt attcttagtc cctcaaaacg ccaagttgca ccagaaaaaa  1980
ttcttcaaat cacaaacgat gtcccaaaaa cagtcaaaaa agtaggagtt tttgttgatg  2040
aacctattga ttttgtaaaa aaagccattc aagttgctca actcgatctg gttcagcttc  2100
acggaaatga agatatgaat tacattaatc aactagatat ttcggttatt aaagcaataa  2160
gaccagacca agaatttaaa gaatacgaag atgtaatttt attatttgat agtccacaag  2220
ctggaagtgg tcaagcattt gattgggact ctttggtgac cagcggtctg aaaaataaat  2280
ttttcatcgc tggtggactt aatccagaaa atgtagcagc tgctattcaa cattttccaa  2340
atgcctacgg tgtggatgtt tcttctggag tagaaactga cggaattaaa aaccttacaa  2400
aaataaaaaa ctttgttcaa aatgcaagcc ttgcctcatc aaagcaatta tttatagaat  2460
ttttaagaat cacaaaaaag ctaaatgaaa ataagatatt cccttattta atgggaagtt  2520
tagcagttga gcaaataatc aattttccaa caaatcctga tgacattgat attcaactca  2580
aaacgtctga ttttgaaaat tttgagcaat taacaagttt aatggaaaaa ttaggttatc  2640
agcttattga cttacatgag cataaatttg aaaaagctag tattcatgtt ggctttgcaa  2700
gtgtggagac ccttaaaaac tatgccgggg ttgactattt gaccattcaa caagaaagaa  2760
tggaaaatgg cgaaaaatat catcttccaa atgttgaaca atcccttaaa atctatgagg  2820
cagcaaaacg agatgagtgg cgaggaggga agcaaaaaga ttcctttatt ttcgatgagt  2880
taataaagga acagaagagg aatgacaatg aatgataatc ttattgaaga gggtgtagag  2940
attcgaaatg gtctcattat taagtcaatt caaaaagaag atatattaga gctttggcaa  3000
attagttatg gacctaaatc tgatttacat tggatgtctt tcaacgctcc ctattttgag  3060
gagccaatcc tgagttggga agaattttca agaaaaatat ctcttaaaat aaattaacca  3120
aatgttgcac ttattatctt tcaaaatcga atcattggaa tgctgtcagc ttattgggaa  3180
gacggtaaat tacaaaaatg gcttgagttt ggtatagtga tttatgatag taaattgtgg  3240
ggacgtggaa ttggacagga tgccttatct ttttggttga agcacctttt tgaaacttat  3300
ccgaagattc agcacatagg atttacaact tggtcaggaa atcaaggaat gatgagacta  3360
ggagaaaaaa gtggtctaaa acttgaaggg caaatcagaa aagttagata ttggcaagaa  3420
acttggtatg attcaataaa atatggaatt ttaagagaag aactaaaaaa ataaataaaa  3480
aaaatcaaag gagcaacaac atgacctaca accaacctaa caacaaagga ttttacggcc  3540
aattcggggg ccaattcgta cctgagacac taatgacagc agtaaaacaa ttagaagaag  3600
cctacgtaga tagtaaaaaa gaccctctct ttcaagcaga acttaaagaa ttacttaaag  3660
actatgttgg acgagaaaac ccactctatt atgcaaaacg cttaacagaa tatgcgggcg  3720
gagcaaaaat ttatcttaaa agagaagacc taaaccatac aggagcacac aaaattaaca  3780
atgccctcgg acaagtcctc cttgccaaaa aaatgggaaa aaataaagtc attgctgaaa  3840
caggtgcagg ccaacacggt gtcgcaagcg caaccgcggc tgccctcttt ggcatggaat  3900
gtacgattta tatgggtgaa gaagacgtta aaagacaatc tctcaatgtc tttcgcatgg  3960
aattactcgg ggcaaaagtt cattcagtaa ctgatggttc acgcgtactt aaagatgcgg  4020
ttaatgcagc acttagagca tggttgctc aagttgaaga tacgcattat gtaatgggct  4080
cagttcttgg accacatcca tttccacaaa ttgtgcgtga ttatcaagct gttattggac  4140
aggaagcgcg tgcccaattt ttagaaaaag aaaataaact tccagatgct ttagtagctt  4200
gtgtcggtgg aggttcaaat tctatgggac ttttttatcc cttcgttaat gatgaatcag  4260
ttgccatgta tggtgttgaa gccgctggcc ttgggattga tacaccacat catgcggcaa  4320
caattactaa aggccgcccc ggtgttcttc acggaacact catggatgtc cttcaagatg  4380
aaaatggtca aatgttagaa gcctttagta tttcagccgg tttagactat ccaggaatcg  4440
gaccagaaca ctcttatttc aatgctgttg gacgagcaaa atatgttgat attacagatg  4500
aagaagcact tgaaggtttt aaaatcttat ctagaactga aggaattatc ccagcactag  4560
aaagttctca tgctatcgcc tatgcagtca aattagcaaa agaattagga gcagataaat  4620
caatgattgt ttgtctttca ggacgtggag ataaggatgt ggttcaagtt aaagaacgac  4680
ttgaagcaga aaaagaggtg aaaaaatgaa aactttacaa atgactttaa gcaataaaaa  4740
aaataatttt attccttata tcatggctgg cgaccatgaa aaaggcttag aaggtcttaa  4800
agaaaccatt caactgcttg agcaagctgg gagttccgct attgaaattg gcgttccatt  4860
ttcagatccg gttgctgatg gtccagtcat cgaacaagca ggtttgcgtg cgttagcaag  4920
aaatgtatca ctttcaagta ttcttgaaac cttaaaaaca attgatacaa aagttcctct  4980
agtaattatg acctatttca atcccgttta tcagtttgga attgaaaagt ttgttgcagc  5040
tcttgaaaaa acaccagtta aaggccttat cattcctgat ttgcctaaag aacatgagga  5100
ctatatcaaa ccatttatca atgataaaga tatctgttta gttcctctgg tctcattaac  5160
cacgccactt tctcggcaaa aagaacttgt agccgatgct gaaggattta tctatgccgt  5220
tgcaataaat ggagtaactg ggaaagaaaa tgcttatagt aaccagcttg accaacattt  5280
aaaagcgtta tcttcattaa cggatgttcc tgttttgaca ggatttggaa tttctacatt  5340
atctgatgtg gaccgtttta ataaagtgtc ctcaggagtt attgttggtt caaaaattgt  5400
tcgtgattta catgaaggta aagaaaacga agttattaaa tttattgaaa acgcaatcaa  5460
tttttaa                                                            5467
```

```
SEQ ID NO: 4           moltype = DNA  length = 4573
FEATURE                Location/Qualifiers
source                 1..4573
                       mol_type = genomic DNA
                       organism = Corynebacterium glutamicum
SEQUENCE: 4
atgacttctc cagcaacact gaaagttctc aacgcctact tggataaccc cactccaacc  60
ctggaggagg caattgaggt gttcaccccg ctgaccgtgg gtgaatacga tgacgtgcac  120
atcgcagcgc tgcttgccac catccgtact cgcggtgagc agttcgctga tattgccggc  180
gctgccaagg cgttcctcgc ggcggctcgt ccgttcccga ttactggcgc aggtttgcta  240
gattccgctg gtactggtgg cgacggtgcc aacaccatca acatcaccac cggcgcatcc  300
ctgatcgcag catccggtgg agtgaagctg gttaagcacg gcaaccgttc ggtgagctcc  360
aagtccggct ccgccgatgt gctggaagcg ctgaatattc ctttgggcct tgatgtggat  420
cgtgctgtga agtggttcga agcgtccaac ttcaccttcc tgttcgcacc tgcgtacaac  480
cctgcgattg cgcatgtgca gccggttcgc caggcgctga aattccccac catcttcaac  540
acgcttggac cattgctgtc cccggcgcgc ccggagcgtc agatcatggg cgtggccaat  600
```

-continued

```
gccaatcatg gacagctcat cgccgaggtc ttccgcgagt tgggccgtac acgcgcgctt  660
gttgtgcatg gcgcaggcac cgatgagatc gcagtccacg gcaccacctt ggtgtgggag  720
cttaaagaag acggcaccat cgagcattac accatcgagc ctgaggacct tggccttggc  780
cgctacaccc ttgaggatct cgtaggtggc ctcggcactg agaacgccga agctatgcgc  840
gctactttcg cgggcaccgg ccctgatgca caccgtgatg cgttggctgc gtccgcaggt  900
gcgatgttct acctcaacgg cgatgtcgac tccttgaaag atggtgcaca aaaggcgctt  960
tccttgcttg ccgacggcac cacccaggca tggttggcca agcacgaaga gatcgattac  1020
tcagaaaagg agtcttccaa tgactagtaa taatctgccc acagtgttgg aaagcatcgt  1080
cgagggtcgt cgcggacacc tggaggaaat tcgcgctcgc atcgctcacg tggatgtgga  1140
tgcgcttcca aaatccaccc gttctctgtt tgattccctc aaccagggta ggggaggggc  1200
gcgtttcatc atggagtgca agtccgcatc gccttctttg ggaatgattc gtgagcacta  1260
ccagccgggt gaaatcgctc gcgtgtactc tcgctacgcc agcggcattt ccgtgctgtg  1320
cgagccggat cgttttggtg gcgattacga tcacctcgct accgttgccg ctacctctca  1380
tcttccggtg ctgtgcaaag acttcatcat tgatcctgtc caggtacacg cggcgcgtta  1440
ctttggtgct gatgccatcc tgctcatgct ctctgtgctt gatgatgaag agtacgcagc  1500
actcgctgcc gaggctgcgc gttttgatct ggatatcctc accgaggtta ttgatgagga  1560
ggaagtcgcc cgcgccatca agctgggtgc gaagatcttt ggcgtcaacc accgcaacct  1620
gcatgatctg tccattgatt tggatcgttc acgtcgcctg tccaagctca ttccagcaga  1680
tgccgtgctc gtgtctgagt ctggcgtgcg cgataccgaa accgtccgcc agctaggtgg  1740
gcactccaat gcattcctcg ttggctccca gctgaccagc caggaaaacg tcgatctggc  1800
agcccgcgaa ttagtctacg gccccaacaa agtctgcgga ctcacctcac caagtgcagc  1860
acaaaccgct cgcgcagcgg gtgcggtcta cggcgggctc atcttcgaag aggcatcgcc  1920
acgcaatgtt tcacgtgaaa cattgcaaaa aatcatcgcc gcagagccca acctgcgcta  1980
cgtcgcggtc agccgtcgca cctccgggta caaggatttg cttgtcgacg gcatcttcgc  2040
cgtacaaatc cacgccccac tgcaggacag cgtcgaagca gaaaaggcat tgatcgccgc  2100
cgttcgtgaa gaggttggac cgcaggtcca ggtctggcgc gcgatctcga tgtccagccc  2160
cttgggggct gaagtggcag ctgcggtgga gggtgacgtc gataagctaa ttcttgatgc  2220
ccatgaaggt ggcagcgggg aagtattcga ctgggctacg gtgccggccg ctgtgaaggc  2280
aaagtctttg ctcgcgggag gcatctctcc ggacaacgct gcgcaggcac tcgctgtggg  2340
ctgcgcaggt ttggacatca actctggcgt ggaatacccc gccggtgcag gcacgtgggc  2400
tggggcgaaa gacgccggcg cgctgctgaa aattttcgcg accatctcca cattccatta  2460
ctaaaggttt aaataggatc atgactgaaa aagaaaactt gggcggctcc acgctgctgc  2520
ctgcatactt cggtgaattc ggcggccagt tcgtcgcgga atccctcctg cctgctctcg  2580
accagctgga gaaggccttc gttgacgcga ccaacagccc agagttccgc gaagaactcg  2640
gcggctacct ccgcgattac ctcggccgcc caaccccgct gaccgaatgc tccaacctgc  2700
cactcgcagg cgaaggcaaa ggctttgcgc ggatcttcct caagcgcgaa gacctcgtcc  2760
acggcggtgc acacaaaact aaccaggtga tcggccaggt gctgcttgcc aagcgcatgg  2820
gcaaaacccg catcatcgca gagaccggcg caggccagca cggcaccgcc accgctctcg  2880
catgtgcgct catgggcctc gagtgcgttg tctacatggg cgccaaggac gttgcccgcc  2940
agcagcccaa cgtctaccgc atgcagctgc acggcgcgaa ggtcatcccc gtggaatctg  3000
gttccggcac cctgaaggac gccgtgaatg aagcgctgcg cgattggacc gcaaccttcc  3060
acgagtccca ctaccttctc ggcaccgccg ccggcccgca cccattccca accatcgtgc  3120
gtgaattcca caaggtgatc tctgaggaag ccaaggcaca gatgctagag cgcaccggca  3180
agcttcccga cgttgtggtc gcctgtgtcg gtggtggctc caacgccatc ggcatgttcg  3240
cagacttcat tgacgatgaa ggtgtagagc tcgtcggcgc tgagccagcc ggtgaaggcc  3300
tcgactccgg caagcacggc gcaaccatca ccaacggtca gatcggcatc ctgcacggca  3360
cccgttccta cctgatgcgc aactccgacg gccaagtgga agagtcctac tccatctccg  3420
ccggacttga ttacccaggc gtcggcccac agcacgcaca cctgcacgcc accggccgcg  3480
ccacctacgt tggtatcacc gacgccgaag ccctccaagc attccagtac ctcgcccgct  3540
acgaaggcat catccccgca ctggaatcct cacacgcgtt cgcctacgca ctcaagcgcg  3600
ccaagaccgc cgaagaggaa ggccagaact taaccatcct cgtctcccta tccggccgtg  3660
gcgacaagga cgttgaccac gtgcgccgca ccctcgaaga aaatccagaa ctgatcctga  3720
aggacaaccg atgagccgtt acgacgatct tttgcacgc ctcgacacgg caggggaggg  3780
cgcctttgtt cccttcatca tgctgagcga cccttcacca gaggaggctt tccagatcat  3840
ctccacagca atcgaagctg gcgcagatgc actggaactt ggcgtacctt tctccgaccc  3900
agttgccgat ggccccaccg tcgcggaatc ccacctccgc gcactcgacg gcggcgccac  3960
cgtagacagc gcactcgagc agatcaagcg cgtgcgcgca gcctacccag aggttcccat  4020
cggaatgctc atctacggca acgttccttt cacccgtggc ttggatcgct tctaccaaga  4080
gttcgctgaa gctggcgcag actccatcct cctgccagac gtcccagtcc gcgaaggcgc  4140
accgttttct gcagcagctg cagcagccgg aattgatccc atttacatcg ctccggccaa  4200
cgccagcgag aaaaccctcg agggtgtctc cgccgcatca aagggctaca tctacgccat  4260
ctcccgcgac ggcgtcaccg gcaccgaacg tgaatcatcc accgacggcc tgtccgcagt  4320
ggtggacaac atcaagaaat ttgatggcgc acccatcctc ttgggcttcg gcatctcatc  4380
ccctcagcac gtggcagacg cgattgcagc gggtgcttcc ggtgcgatca cgggttccgc  4440
gatcaccaag atcattgctt cccactgcga aggtgagcac ccgaacccgt ccaccattcg  4500
agatatggac ggtttgaaga aggatctcac tgagttcatc tctgcgatga aggcagcgac  4560
caagaaggtt tag                                                    4573
```

```
SEQ ID NO: 5          moltype = AA  length = 531
FEATURE               Location/Qualifiers
source                1..531
                      mol_type = protein
                      organism = Escherichia coli
SEQUENCE: 5
MADILLLDNI DSFTYNLADQ LRSNGHNVVI YRNHIPAQTL IERLATMSNP VLMLSPGPGV  60
PSEAGCMPEL LTRLRGKLPI IGICLGHQAI VEAYGGYVGQ AGEILHGKAS SIEHDGQAMF  120
AGLTNPLPVA RYHSLVGSNI PAGLTINAHF NGMVMAVRHD ADRVCGFQFH PESILTTQGA  180
RLLEQTLAWA QQKLEPANTL QPILEKLYQA QTLSQQESHQ LFSAVVRGEL KPEQLAAALV  240
SMKIRGEHPN EIAGAATALL ENAAPFPRPD YLFADIVGTG GDGSNSINIS TASAFVAAAC  300
```

-continued

```
GLKVAKHGNR SVSSKSGSSD LLAAFGINLD MNADKSRQAL DELGVCFLFA PKYHTGFRHA  360
MPVRQQLKTR TLFNVLGPLI NPAHPPLALI GVYSPELVLP IAETLRVLGY QRAAVVHSGG  420
MDEVSLHAPT IVAELHDGEI KSYQLTAEDF GLTPYHQEQL AGGTPEENRD ILTRLLQGKG  480
DAAHEAAVAA NVAMLMRLHG HEDLQANAQT VLEVLRSGSA YDRVTALAAR G           531

SEQ ID NO: 6           moltype = AA  length = 348
FEATURE                Location/Qualifiers
source                 1..348
                       mol_type = protein
                       organism = Corynebacterium glutamicum
SEQUENCE: 6
MTSPATLKVL NAYLDNPTPT LEEAIEVFTP LTVGEYDDVH IAALLATIRT RGEQFADIAG  60
AAKAFLAAAR PFPITGAGLL DSAGTGGDGA NTINITTGAS LIAASGGVKL VKHGNRSVSS  120
KSGSADVLEA LNIPLGLDVD RAVKWFEASN FTFLFAPAYN PAIAHVQPVR QALKFPTIFN  180
TLGPLLSPAR PERQIMGVAN ANHGQLIAEV FRELGRTRAL VVHGAGTDEI AVHGTTLVWE  240
LKEDGTIEHY TIEPEDLGLG RYTLEDLVGG LGTENAEAMR ATFAGTGPDA HRDALAASAG  300
AMFYLNGDVD SLKDGAQKAL SLLADGTTQA WLAKHEEIDY SEKESSND            348

SEQ ID NO: 7           moltype = AA  length = 348
FEATURE                Location/Qualifiers
source                 1..348
                       mol_type = protein
                       organism = Corynebacterium glutamicum
SEQUENCE: 7
MTSPATLKVL NAYLDNPTPT LEEAIEVFTP LTVGEYDDVH IAALLATIRT RGEQFADIAG  60
AAKAFLAAAR PFPITGAGLL DSAGTGGDGA NTINITTGAS LIAASGGVKL VKHGNRSVSS  120
KSGSADVLEA LNIPLGLDVD RAVKWFEAFN FTFLFAPAYN PEIAHVQPVR QALKFPTIFN  180
TLGPLLSPAR PERQIMGVAN ANHGQLIAEV FRELGRTRAL VVHGAGTDEI AVHGTTLVWE  240
LKEDGTIEHY TIEPEDLGLG RYTLEDLVGG LGTENAEAMR ATFAGTGPDA HRDALAASAG  300
AMFYLNGDVD SLKDGAQKAL SLLADGTTQA WLAKHEEIDY SEKESSND            348

SEQ ID NO: 8           moltype = AA  length = 452
FEATURE                Location/Qualifiers
source                 1..452
                       mol_type = protein
                       organism = Escherichia coli
SEQUENCE: 8
MQTVLAKIVA DKAIWVETRK EQQPLASFQN EVQPSTRHFY DALQGARTAF ILECKKASPS  60
KGVIRDDFDP ARIAAIYKHY ASAISVLTDE KYFQGSFDFL PIVSQIAPQP ILCKDFIIDP  120
YQIYLARYYQ ADACLLMLSV LDDEQYRQLA AVAHSLEMGV LTEVSNEEEL ERAIALGAKV  180
VGINNRDLRD LSIDLNRTRE LAPKLGHNVT VISESGINTY AQVRELSHFA NGFLIGSALM  240
AHDDLNAAVR RVLLGENKVC GLTRGQDAKA AYDAGAIYGG LIFVATSPRC VNVEQAQEVM  300
AAAPLQYVGV FRNHDIADVA DKAKVLSLAA VQLHGNEDQL YIDNLREALP AHVAIWKALS  360
VGETLPARDF QHIDKYVFDN GQGGSGQRFD WSLLNGQTLG NVLLAGGLGA DNCVEAAQTG  420
CAGLDFNSAV ESQPGIKDAR LLASVFQTLR AY                              452

SEQ ID NO: 9           moltype = AA  length = 474
FEATURE                Location/Qualifiers
source                 1..474
                       mol_type = protein
                       organism = Corynebacterium glutamicum
SEQUENCE: 9
MTSNNLPTVL ESIVEGRRGH LEEIRARIAH VDVDALPKST RSLFDSLNQG RGGARFIMEC  60
KSASPSLGMI REHYQPGEIA RVYSRYASGI SVLCEPDRFG GDYDHLATVA ATSHLPVLCK  120
DFIIDPVQVH AARYFGADAI LLMLSVLDDE EYAALAAEAA RFDLDILTEV IDEEEVARAI  180
KLGAKIFGVN HRNLHDLSID LDRSRRLSKL IPADAVLVSE SGVRDTETVR QLGGHSNAFL  240
VGSQLTSQEN VDLAARELVY GPNKVCGLTS PSAAQTARAA GAVYGGLIFE EASPRNVSRE  300
TLQKIIAAEP NLRYVAVSRR TSGYKDLLVD GIFAVQIHAP LQDSVEAEKA LIAAVREEVG  360
PQVQVWRAIS MSSPLGAEVA AAVEGDVDKL ILDAHEGGSG EVFDWATVPA AVKAKSLLAG  420
GISPDNAAQA LAVGCAGLDI NSGVEYPAGA GTWAGAKDAG ALLKIFATIS TFHY        474

SEQ ID NO: 10          moltype = AA  length = 397
FEATURE                Location/Qualifiers
source                 1..397
                       mol_type = protein
                       organism = Escherichia coli
SEQUENCE: 10
MTTLLNPYFG EFGGMYVPQI LMPALRQLEE AFVSAQKDPE FQAQFNDLLK NYAGRPTALT  60
KCQNITAGTN TTLYLKREDL LHGGAHKTNQ VLGQALLAKR MGKTEIIAET GAGQHGVASA  120
LASALLGLKC RIYMGAKDVE RQSPNVFRMR LMGAEVIPVH SGSATLKDAC NEALRDWSGS  180
YETAHYMLGT AAGPHPYPTI VREFQRMIGE ETKAQILERE GRLPDAVIAC VGGGSNAIGM  240
FADFINETNV GLIGVEPGGH GIETGEHGAP LKHGRVGIYF GMKAPMMQTE DGQIEESYSI  300
SAGLDFPSVG PQHAYLNSTG RADYVSITDD EALEAFKTLC LHEGIIPALE SSHALAHALK  360
MMRENPDKEQ LLVVNLSGRG DKDIFTVHDI LKARGEI                         397

SEQ ID NO: 11          moltype = AA  length = 417
FEATURE                Location/Qualifiers
source                 1..417
                       mol_type = protein
```

```
                        organism = Corynebacterium glutamicum
SEQUENCE: 11
MTEKENLGGS TLLPAYFGEF GGQFVAESLL PALDQLEKAF VDATNSPEFR EELGGYLRDY  60
LGRPTPLTEC SNLPLAGEGK GFARIFLKRE DLVHGGAHKT NQVIGQVLLA KRMGKTRIIA  120
ETGAGQHGTA TALACALMGL ECVVYMGAKD VARQQPNVYR MQLHGAKVIP VESGSGTLKD  180
AVNEALRDWT ATFHESHYLL GTAAGPHPFP TIVREFHKVI SEEAKAQMLE RTGKLPDVVV  240
ACVGGGSNAI GMFADFIDDE GVELVGAEPA GEGLDSGKHG ATITNGQIGI LHGTRSYLMR  300
NSDGQVEESY SISAGLDYPG VGPQHAHLHA TGRATYVGIT DAEALQAFQY LARYEGIIPA  360
LESSHAFAYA LKRAKTAEEE GQNLTILVSL SGRGDKDVDH VRRTLEENPE LILKDNR     417

SEQ ID NO: 12           moltype = AA  length = 520
FEATURE                 Location/Qualifiers
source                  1..520
                        mol_type = protein
                        organism = Escherichia coli
SEQUENCE: 12
MQTQKPTLEL LTCEGAYRDN PTALFHQLCG DRPATLLLES ADIDSKDDLK SLLLVDSALR  60
ITALGDTVTI QALSGNGEAL LALLDNALPA GVESEQSPNC RVLRFPPVSP LLDEDARLCS  120
LSVFDAFRLL QNLLNVPKEE REAMFFGGLF SYDLVAGFED LPQLSAENNC PDFCFYLAET  180
LMVIDHQKKS TRIQASLFAP NEEEKQRLTA RLNELRQQLT EAAPPLPVVS VPHMRCECNQ  240
SDEEFGGVVR LLQKAIRAGE IFQVVPSRRF SLPCPSPLAA YYVLKKSNPS PYMFFMQDND  300
FTLFGASPES SLKYDATSRQ IEIYPIAGTR PRGRRADGSL DRDLDSRIEL EMRTDHKELS  360
EHLMLVDLAR NDLARICTPG SRYVADLTKV DRYSYVMHLV SRVVGELRHD LDALHAYRAC  420
MNMGTLSGAP KVRAMQLIAE AEGRRRGSYG GAVGYFTAHG DLDTCIVIRS ALVENGIATV  480
QAGAGVVLDS VPQSEADETR NKARAVLRAI ATAHHAQETF                        520

SEQ ID NO: 13           moltype = AA  length = 280
FEATURE                 Location/Qualifiers
source                  1..280
                        mol_type = protein
                        organism = Corynebacterium glutamicum
SEQUENCE: 13
MSRYDDLFAR LDTAGEGAFV PFIMLSDPSP EEAFQIISTA IEAGADALEL GVPFSDPVAD  60
GPTVAESHLR ALDGGATVDS ALEQIKRVRA AYPEVPIGML IYGNVPFTRG LDRFYQEFAE  120
AGADSILLPD VPVREGAPFS AAAAAAGIDP IYIAPANASE KTLEGVSAAS KGYIYAISRD  180
GVTGTERESS TDGLSAVVDN IKKFDGAPIL LGFGISSPQH VADAIAAGAS GAITGSAITK  240
IIASHCEGEH PNPSTIRDMD GLKKDLTEFI SAMKAATKKV                        280

SEQ ID NO: 14           moltype = AA  length = 439
FEATURE                 Location/Qualifiers
source                  1..439
                        mol_type = protein
                        organism = Psilocybe cubensis
SEQUENCE: 14
MQVIPACNSA AIRSLCPTPE SFRNMGWLSV SDAVYSEFIG ELATRASNRN YSNEFGLMQP  60
IQEFKAFIES DPVVHQEFID MFEGIQDSPR NYQELCNMFN DIFRKAPVYG DLGPPVYMIM  120
AKLMNTRAGF SAFTRQRLNL HFKKLFDTWG LFLSSKDSRN VLVADQFDDR HCGWLNERAL  180
SAMVKHYNGR AFDEVFLCDK NAPYYGFNSY DDFFNRRFRN RDIDRPVVGG VNNTTLISAA  240
CESLSYNVSY DVQSLDTLVF KGETYSLKHL LNNDPFTPQF EHGSILQGFL NVTAYHRWHA  300
PVNGTIVKII NVPGTYFAQA PSTIGDPIPD NDYDPPPYLK SLVYFSNIAA RQIMFIEADN  360
KEIGLIFLVF IGMTEISTCE ATVSEGQHVN RGDDLGMFHF GGSSFALGLR KDCRAEIVEK  420
FTEPGTVIRI NEVVAALKA                                               439

SEQ ID NO: 15           moltype = AA  length = 439
FEATURE                 Location/Qualifiers
source                  1..439
                        mol_type = protein
                        organism = Psilocybe cyanescens
SEQUENCE: 15
MQVLPACQSS ALKTLCPSPE AFRKLGWLPT SDEVYNEFID DLTGRTCNEK YSSQVTLLKP  60
IQDFKTFIEN DPIVYQEFIS MFEGIEQSPT NYHELCNMFN DIFRKAPLYG DLGPPVYMIM  120
ARIMNTQAGF SAFTKESLNF HFKKLFDTWG LFLSSKNSRN VLVADQFDDK HYGWFSERAK  180
TAMMINYPGR TFEKVFICDE HVPYHGFTSY DDFFNRRFRD KDTDRPVVGG VTDTTLIGAA  240
CESLSYNVSH NVQSLDTLVI KGEAYSLKHL LHNDPFTPQF EHGSIIQGFL NVTAYHRWHS  300
PVNGTIVKIV NVPGTYFAQA PYTIGSPIPD NDRDPPPYLK SLVYFSNIAA RQIMFIEADN  360
KDIGLIFLVF IGMTEISTCE ATVCEGQHVN RGDDLGMFHF GGSSFALGLR KDSKAKILEK  420
FAKPGTVIRI NELVASVRK                                               439

SEQ ID NO: 16           moltype = AA  length = 436
FEATURE                 Location/Qualifiers
source                  1..436
                        mol_type = protein
                        organism = Psilocybe cyanescens
SEQUENCE: 16
MQVLTACYTS TLKSLLPSFD AFRSMGWLPV SDKTYNEWIG DLRSRASDKN YTSQVGLIQP  60
IKDFKAFIES DPVVHQEFIT MFEGIEESPR NYEELCHMFN DIFRKAPVYG DLGPPVYMVM  120
ARIMNTQAGF SAFTKQSLNS HFKRLFDTWG VFLSSKESRY VLVTDQFDDN HYGWLSDRAK  180
SAMVKHYYGR TFEQVFICDE HAPYHGFQSY DDFFNRRFRD RDIDRPVVGG IENTTLISAA  240
CESLSYNVCH DLQSLDTLFV KGESYSLKHL LNDDPFARQF EHGSILQGFL NVTAYHRWHA  300
```

-continued

```
PVNGTILKII NVPGTYFAQA PHTIGDSLDS DHPPYLKSLA YFSNIAARQI MFIEADNKDI  360
GLIFLVFIGM TEISTCEATV SEGQHVNRGD DLGMFHFGGS SFALGLRKDC KAEIFERFAE  420
QGTVIKINEV VAAVKD                                                 436

SEQ ID NO: 17          moltype = AA  length = 430
FEATURE                Location/Qualifiers
source                 1..430
                       mol_type = protein
                       organism = Gymnopilus dilepis
SEQUENCE: 17
MAKTLRPTAQ AFRELGWLPA SDGVYNKFMK DLTNRASNEN HLCHVALLQP IQDFKTFIEN  60
DPVVYQEFVC MFEGIEESPR NYHELCNMFN EIFRRAPYYG DLGPPVYMAM AKIMNTRAGF  120
SAFTRESLNF HFKRLFDTWG LFLSSPASRD VLVADKFDSK HYGWFSEPAK AAMMAQYDGR  180
TFEQVFICDE TAPYHGFKSY DDFFNRKFRA MDIDRPVVGG IANTTLIGSP CEALSYNVSD  240
DVHSLETLYF KGEGYSLRHL LHDDPSTEQF EHGSIIQGFL NITGYHRWHA PVSGTIMKIV  300
DVPGTYFAQA PSTIGDPFPV NDYDPQAPYL RSLAYFSNIA ARQIIFIQAD NEDIGLIYLI  360
LIGMTEVSTC EALVCPGQHV ERGDDLGMFH FGGSSFALGL RKNSKAAILE ELKTQGTVIK  420
VNDVIAAVQA                                                        430

SEQ ID NO: 18          moltype = AA  length = 480
FEATURE                Location/Qualifiers
source                 1..480
                       mol_type = protein
                       organism = Homo sapiens
SEQUENCE: 18
MNASEFRRRG KEMVDYMANY MEGIEGRQVY PDVEPGYLRP LIPAAAPQEP DTFEDIINDV  60
EKIIMPGVTH WHSPYFFAYF PTASSYPAML ADMLCGAIGC IGFSWAASPA CTELETVMMD  120
WLGKMLELPK AFLNEKAGEG GGVIQGSASE ATLVALLAAR TKVIHRLQAA SPELTQAAIM  180
EKLVAYSSDQ AHSSVERAGL IGGVKLKAIP SDGNFAMRAS ALQEALERDK AAGLIPFFMV  240
ATLGTTTCCS FDNLLEVGPI CNKEDIWLHV DAAYAGSAFI CPEFRHLLNG VEFADSFNFN  300
PHKWLLVNFD CSAMWVKKRT DLTGAFRLDP TYLKHSHQDS GLITDYRHWQ IPLGRRFRSL  360
KMWFVFRMYG VKGLQAYIRK HVQLSHEFES LVRQDPRFEI CVEVILGLVC FRLKGSNKVN  420
EALLQRINSA KKIHLVPCHL RDKFVLRFAI CSRTVESAHV QRAWEHIKEL AADVLRAERE  480

SEQ ID NO: 19          moltype = AA  length = 480
FEATURE                Location/Qualifiers
source                 1..480
                       mol_type = protein
                       organism = Bacillus atrophaeus
SEQUENCE: 19
MSENLQLSAE EMRQLGYQAV DLIIDHMNHL KSKPVSETID SDILRNKLTE SIPENGSDPK  60
ELLHFLNRNV FNQITHVDHP HFLAFVPGPN NYVGVVADFL ASGFNVFPTA WIAGAGAEQI  120
ELTTINWLKS MLGFPDSAEG LFVSGGSMAN LTALTVARQA KLNNDIENAV VYFSDQTHFS  180
VDRALKVLGF KHHQICRIET DEHLRISVSA LKKQIKEDRT KGKKPFCVIA NAGTTNCGAV  240
DSLNELADLC NDEDVWLHAD GSYGAPAILS EKGSAMLQGI HRADSLTLDP HKWLFQPYDV  300
GCVLIRNSQY LSKTFRMMPE YIKDSETNVE GEINFGECGI ELSRRFRALK VWLSFKVFGV  360
AAFRQAIDHG IMLAEQVEAF LGKAKDWEVV TPAQLGIVTF RYIPSELAST DTINEINKKL  420
VKEITHRGFA MLSTTELKEK VVIRLCSINP RTTTEEMLQI MMKIKALAEE VSISYPCVAE  480

SEQ ID NO: 20          moltype = AA  length = 500
FEATURE                Location/Qualifiers
source                 1..500
                       mol_type = protein
                       organism = Catharanthus roseus
SEQUENCE: 20
MGSIDSTNVA MSNSPVGEFK PLEAEEFRKQ AHRMVDFIAD YYKNVETYPV LSEVEPGYLR  60
KRIPETAPYL PEPLDDIMKD IQKDIIPGMT NWMSPNFYAF FPATVSSAAF LGEMLSTALN  120
SVGFTWVSSP AATELEMIVM DWLAQILKLP KSFMFSGTGG GVIQNTTSES ILCTIIAARE  180
RALEKLGPDS IGKLVCYGSD QTHTMFPKTC KLAGIYPNNI RLIPTTVETD FGISPQVLRK  240
MVEDDVAAGY VPLFLCATLG TTSTTATDPV DSLSEIANEF GIWIHVDAAY AGSACICPEF  300
RHYLDGIERV DSLSLSPHKW LLAYLDCTCL WVKQPHLLLR ALTTNPEYLK NKQSDLDKVV  360
DFKNWQIATG RKFRSLKLWL ILRSYGVVNL QSHIRSDVAM GKMFEEWVRS DSRFEIVVPR  420
NFSLVCFRLK PDVSSLHVEE VNKKLLDMLN STGRVYMTHT IVGGIYMLRL AVGSSLTEEH  480
HVRRVWDLIQ KLTDDLLKEA                                             500

SEQ ID NO: 21          moltype = AA  length = 309
FEATURE                Location/Qualifiers
source                 1..309
                       mol_type = protein
                       organism = Psilocybe cubensis
SEQUENCE: 21
MHIRNPYRTP IDYQALSEAF PPLKPFVSVN ADGTSSVDLT IPEAQRAFTA ALLHRDFGLT  60
MTIPEDRLCP TVPNRLNYVL WIEDIFNYTN KTLGLSDDRP IKGVDIGTGA SAIYPMLACA  120
RFKAWSMVGT EVERKCIDTA RLNVVANNLQ DRLSILETSI DGPILVPIFE ATEEYEYEFT  180
MCNPPFYDGA ADMQTSDAAK GFGFGVGAPH SGTVIEMSTE GGESAFVAQM VRESLKLRTR  240
CRWYTSNLGK LKSLKEIVGL LKELEISNYA INEYVQGSTR RYAVAWSFTD IQLPEELSRP  300
SNPELSSLF                                                         309

SEQ ID NO: 22          moltype = AA  length = 312
```

-continued

```
FEATURE                Location/Qualifiers
source                 1..312
                       mol_type = protein
                       organism = Psilocybe cyanescens
SEQUENCE: 22
MHIRNPYRSP IDYQALVEAF PPLRPYVTVN QDNTTSIDLT VPEVQRLYTA ALLHRDFGLV  60
IDLPEDRLCP TLLTRTPRLN YVLWVEDILK VTNTALGLSE DRPVKGIDIG TGAAAIYPML  120
ACARFKTWSM IGTEIDRKCI DTARVNVLTN NLQDRLSIIE TSIDGPILVP IFEATTDYEY  180
DFTMCNPPFY DGAADMQTSD AAKGFGFGVN APHSGTVIEM STEGGESAFV AQMVRESLDH  240
RTRCRWFTSN LGKLKSLHEI VGLLREHQIS NYAINEYVQG TTRRYAIAWS FTNIRLPEDL  300
TRPSNPELSS LF                                                    312

SEQ ID NO: 23          moltype = AA  length = 317
FEATURE                Location/Qualifiers
source                 1..317
                       mol_type = protein
                       organism = Psilocybe cyanescens
SEQUENCE: 23
MHNRNPYRDV IDYQALAEAY PPLKPHVTVN ADNTASIDLT IPEVQRQYTA ALLHRDFGLT  60
ITLPEDRLCP TVPNRLNYVL WIEDIFQCTN KALGLSDDRP VKGVDIGTGA SAIYPMLACA  120
RFKQWSMIAT EVERKCIDTA RLNVLANNLQ DRLSILEVSV DGPILVPIFD TFERATSDYE  180
FEFTMCNPPF YDGAADMQTS DAAKGFGFGV NAPHSGTVIE MATEGGEAAF VAQMVRESMK  240
LQTRCRWFTS NLGKLKSLHE IVALLRESQI TNYAINEYVQ GTTRRYALAW SFTDIKLTEE  300
LYRPSNPELG PLCSTFV                                               317

SEQ ID NO: 24          moltype = AA  length = 309
FEATURE                Location/Qualifiers
source                 1..309
                       mol_type = protein
                       organism = Gymnopilus dilepis
SEQUENCE: 24
MHIRNPYLTP PDYEALAEAF PALKPYVTVN PDKTTTIDFA IPEAQRLYTA ALLYRDFGLT  60
ITLPPDRLCP TVPNRLNYVL WIQDILQITS AALGLPEARQ VKGVDIGTGA AAIYPILGCS  120
LAKNWSMVGT EVEQKCIDIA RQNVISNGLQ DRITITANTI DAPILLPLFE GDSNFEWEFT  180
MCNPPFYDGA ADMETSQDAK GFGFGVNAPH TGTVVEMATD GGEAAFVSQM VRESLHLKTR  240
CRWFTSNLGK LKSLHEIVGL LREHQITNYA INEYVQGTTR RYAIAWSFTD LRLSDHLPRP  300
PNPDLSALF                                                        309

SEQ ID NO: 25          moltype = AA  length = 263
FEATURE                Location/Qualifiers
source                 1..263
                       mol_type = protein
                       organism = Homo sapiens
SEQUENCE: 25
MKGGFTGGDE YQKHFLPRDY LATYYSFDGS PSPEAEMLKF NLECLHKTFG PGGLQGDTLI  60
DIGSGPTIYQ VLAACDSFQD ITLSDFTDRN REELEKWLKK EPGAYDWTPA VKFACELEGN  120
SGRWEEKEEK LRAAVKRVLK CDVHLGNPLA PAVLPLADCV LTLLAMECAC CSLDAYRAAL  180
CNLASLLKPG GHLVTTVTLR LPSYMVGKRE FSCVALEKEE VEQAVLDAGF DIEQLLHSPQ  240
SYSVTNAANN GVCFIVARKK PGP                                        263

SEQ ID NO: 26          moltype = AA  length = 209
FEATURE                Location/Qualifiers
source                 1..209
                       mol_type = protein
                       organism = Acinetobacter sp.
SEQUENCE: 26
MIYKFYQQHI FPHLLNQVMQ TPSLMDQRRQ LLLPIAGDVL EIGFGTGVNL PFYQNVETLY  60
ALEPNADLYQ LAAKRIHEST IHVQHIQAYA EKLPFADASL DHIVSTWTLC SIENLAQALI  120
EMYRVLKPNG TLHLVEHVQY QDNAKLQHLQ NLLTPIQKRL ADGCHLNRNI EQALRDAHFD  180
FTEQHYFAAQ GIPKLAQRMF FARAQKQPE                                  209

SEQ ID NO: 27          moltype = AA  length = 445
FEATURE                Location/Qualifiers
source                 1..445
                       mol_type = protein
                       organism = Oryza sativa
SEQUENCE: 27
MEITSSAMLK TTTTPPHPLA GEKVPLSAFD RAAFDVFVPL VFAYRAPAPS SEAVKEGLRV  60
AVAAYPLVSG RIAVDGQGRR RRRRVLHVNN EGVLVLDATV EVDLDAVLAA NVATDLYPAL  120
PEHSFGAALL QVQLTRFGCG GLVVGLIGHH HVFDGHSMST FCATWARAVR DSEAFIVPSP  180
SLDRAITGVP RSPPAPVFDH RSIEFKVGNK SSDSSGAAAA AAVEKIANIG VRFTAKFVAE  240
LKARVGGRCS TFECVLAHAW KKITAARGLK PEEFTRVRVA VNCRRRANPP APADLFGNMV  300
LWAFPRLQVR RLLSSSYRDV VGAIRAAVAR VDAEYIQSFV DYVEVADARG EELAATAAEP  360
GETLCPDLEV DSWLGFRFHE MDLGTGPPAA VLSPDLPIEG LMILVPVGGD GGGVDLFVAL  420
ADDHAQAFEQ ICYSLEEHAM IHSHL                                      445

SEQ ID NO: 28          moltype = AA  length = 207
FEATURE                Location/Qualifiers
source                 1..207
```

```
                         mol_type = protein
                         organism = Homo sapiens
SEQUENCE: 28
MSTQSTHPLK PEAPRLPPGI PESPSCQRRH TLPASEFRCL TPEDAVSAFE IEREAFISVL  60
GVCPLYLDEI RHFLTLCPEL SLGWFEEGCL VAFIIGSLWD KERLMQESLT LHRSGGHIAH  120
LHVLAVHRAF RQQGRGPILL WRYLHHLGSQ PAVRRAALMC EDALVPFYER FSFHAVGPCA  180
ITVGSLTFME LHCSLRGHPF LRRNSGC                                      207

SEQ ID NO: 29            moltype = AA  length = 275
FEATURE                  Location/Qualifiers
source                   1..275
                         mol_type = protein
                         organism = Drosophila melanogaster
SEQUENCE: 29
MEVQKLPDQS LISSMMLDSR CGLNDLYPIA RLTQKMEDAL TVSGKPAACP VDQDCPYTIE  60
LIQPEDGEAV IAMLKTFFFK DEPLNTFLDL GECKELEKYS LKPLPDNCSY KAVNKKGEII  120
GVFLNGLMRR PSPDDVPEKA ADSCEHPKFK KILSLMDHVE EQFNIFDVYP DEELILDGKI  180
LSVDTNYRGL GIAGRLTERA YEYMRENGIN VYHVLCSSHY SARVMEKLGF HEVFRMQFAD  240
YKPQGEVVFK PAAPHVGIQV MAKEVGPAKA AQTKL                             275

SEQ ID NO: 30            moltype = AA  length = 209
FEATURE                  Location/Qualifiers
source                   1..209
                         mol_type = protein
                         organism = Danio rerio
SEQUENCE: 30
MMAPQVVSSP FLKPFFLKTP ISVSSPRRQR RHTLPASEFR NLTPQDAISV FEIEREAFIS  60
VSGECPLTLD EVLVFLGQCP ELSMGWFEEG QLVAFIIGSG WDKEKLEQEA MSTHVPDSPT  120
VHIHVLSVHR HCRQQGKGSI LLWRYLQYLR CLPGLRRALL VCEEFLVPFY QKAGFKEKGP  180
SAISVAALTF TEMEYQLGGL AYARRNSGC                                    209

SEQ ID NO: 31            moltype = AA  length = 436
FEATURE                  Location/Qualifiers
source                   1..436
                         mol_type = protein
                         organism = Oryza sativa
SEQUENCE: 31
MAAVTVEITR SEVLRPSPAS AGGGEMVPLT VFDRAATDGY IPTMFAWDAA AAAALSNDAI  60
KDGLAAVLSR FPHLAGRFAV DERGRKCFRL NNAGARVLEA SAAGDLADAL AHDVAAHVNQ  120
LYPQADKDRV DEPLLQVQLT RYTCGGLVIG AVSHHQVADG QSMSVFFTEW AAAVRTAGAA  180
LPTPFLDRSA VAAPRIPPAP AFDHRNVEFR GEGSRSHSYG ALPLERMRNL AVHFPPEFVA  240
GLKARVGGAR CSTFQCLLAH AWKKITAARD LSPKEYTQVR VAVNCRGRAG PAVPTDYFGN  300
MVLWAFPRMQ VRDLLSASYA AVVGVIRDAV ARVDERYIQS FVDFGEVAAG DELAPTAAEP  360
GTAFCPDLEV DSWIGFRFHD LDFGGGPPCA FLPPDVPIDG LLIFVPSCAA KGGVEMFMAL  420
DDQHVEALRQ ICYSMD                                                  436

SEQ ID NO: 32            moltype = AA  length = 508
FEATURE                  Location/Qualifiers
source                   1..508
                         mol_type = protein
                         organism = Psilocybe cubensis
SEQUENCE: 32
MIAVLFSFVI AGCIYYIVSR RVRRSRLPPG PPGIPIPFIG NMFDMPEESP WLTFLQWGRD  60
YNTDILYVDA GGTEMVILNT LETITDLLEK RGSIYSGRLE STMVNELMGW EFDLGFITYG  120
DRWREERRMF AKEFSEKGIK QFRHAQVKAA HQLVQQLTKT PDRWAQHIRH QIAAMSLDIG  180
YGIDLAEDDP WLEATHLANE GLAIASVPGK FWVDSFPSLK YLPAWFPGAV FKRKAKVWRE  240
AADHMVDMPY ETMRKLAPQG LTRPSYASAR LQAMDLNGDL EHQEHVIKNT AAEVNVGGGD  300
TTVSAMSAFI LAMVKYPEVQ RKVQAELDAL TNNGQIPDYD EEDDSLPYLT ACIKELFRWN  360
QIAPLAIPHK LMKDDVYRGY LIPKNTLVFA NTWAVLNDPE VYPDPSVFRP ERYLGPDGKP  420
DNTVRDPRKA AFGYGRRNCP GIHLAQSTVW IAGATLLSAF NIERPVDQNG KPIDIPADFT  480
TGFFRHPVPF QCRFVPRTEQ VSQSVSGP                                     508

SEQ ID NO: 33            moltype = AA  length = 507
FEATURE                  Location/Qualifiers
source                   1..507
                         mol_type = protein
                         organism = Psilocybe cyanescens
SEQUENCE: 33
MIVLLVSLVL AGCIYYANAR RVRRSRLPPG PPGIPLPFIG NMFDMPSESP WLRFLQWGRD  60
YHTDILYLNA GGTEIIILNT LDAITDLLEK RGSMYSGRLE STMVNELMGW EFDLGFITYG  120
ERWREERRMF AKEFSEKNIR QFRHAQIKAA NQLVRQLIKT PDRWSQHIRH QIAAMSLDIG  180
YGIDLAEDDP WIAATQLANE GLAEASVPGS FWVDSFPALK YLPSWLPGAG FKRKAKVWKE  240
GADHMVNMPY ETMKKLTVQG LARPSYASAR LQAMDPDGDL EHQEHVIRNT ATEVNVGGGD  300
TTVSAVSAFI LAMVKYPEVQ RQVQAELDAL TSKGVVPNYD EEDDSLPYLT ACVKEIFRWN  360
QIAPLAIPHR LIKDDVYRGY LIPKNALVYA NSWAVLNDPE EYPNPSEFRP ERYLSSDGKP  420
DPTVRDPRKA AFGYGRRNCP GIHLAQSTVW IAGATLLSVF NIERPVDGNG KPIDIPATFT  480
TGFFRHPEPF QCRFVPRTQE ILKSVSG                                      507

SEQ ID NO: 34            moltype = AA  length = 483
```

-continued

```
FEATURE               Location/Qualifiers
source                1..483
                      mol_type = protein
                      organism = Psilocybe cyanescens
SEQUENCE: 34
MINLPLSLVL VGCVYYIVSR RIRRSRLPPG PPGIPIPFVG NMYDMPSESP WLTFLQWGRE  60
YNDRGLTTIF RVESTMVNKL MGWEFDLGFI TYGDRWREER RMFSKEFSEK AIKQFRHSQV  120
KAAHRFVQQL AANGEPSRLP HYIRHQIAAM SLDIGYGVDL AQDDPWLEAA HLANEGLATA  180
SVPGTFWIDS FPALKYLPSW FPGAGFKRQA KIWKEAADHM VNMPYERMKK LAPQGLARPS  240
YASARLQAMD PNGDLEYQEQ VIKNTASQVN VGGGDTTVSA VSAFILAMVI YPEVQRKVQA  300
ELDAVLSNGR IPDYDEENDS MPYLTACVKE LFRWNQIAPL AIPHKLVKDD IYRGYLIPKN  360
TLVFANSWAV LNDPEVYPDP SVFRPERYLG PDGKPNDTVR DPRKAAFGYG RRNCPGIHLA  420
LSTVWITAAT LLSVFDIERP VDHKGNPIDI PAAFTKGFFR HPEPFQCRFV PRNEDSLKSL  480
SGL                                                                483

SEQ ID NO: 35         moltype = AA  length = 563
FEATURE               Location/Qualifiers
source                1..563
                      mol_type = protein
                      organism = Gymnopilus dilepis
SEQUENCE: 35
MQGNPAVLLL LLTLTLCVYY AHSRRARRAR LPPGPPGIPL PFVGNLFDMP SNSPWLTYLQ  60
WGETYQTDII YLNAGGTEMV ILNTLEAITD LLEKRGSIYS GRFESTMVNE LMGWDFDLGF  120
ITYGERWREE RRMFSKEFNE KNIKQFRHAQ IRAANLLVGQ LTKTPERWHQ LIRHQIAAMS  180
LDIGYGIDLL EGDPWLEATQ LANEGLAIAS VPGSFWVDSL PILKYMPSWF PGAEFKRKAK  240
VWRESTDHMI NMPYEKMKKL MVQDLVRPSY ASARLQEMDP NGDLQHQEHV IRNTAMEVNV  300
GGADTTVSAV AAFILAMVKY PDVQRKVQAE LDAVGCRDEL PEFDEDNDAL PYLTACVKEI  360
FRWNQVAPLA IPHRLDKDDH YRGYIIPKNA LVFANTWAVL NDPSVYPDPS EFRPERYLGP  420
DGKPDPRIRD PRKAAFGYGR RACPGIHLAQ STVWIVGATL LSVFDIERPM DANGKPIDIP  480
AAFTTGFFRY SIHDCLVVET MHPANTVCVD IPNPSDADSF LVPKRLSNPH PIIDLPSRNP  540
ACQEDGVVAL SNAWRSTLPV QDV                                          563

SEQ ID NO: 36         moltype = AA  length = 691
FEATURE               Location/Qualifiers
source                1..691
                      mol_type = protein
                      organism = Saccharomyces cerevisiae
SEQUENCE: 36
MPFGIDNTDF TVLAGLVLAV LLYVKRNSIK ELLMSDDGDI TAVSSGNRDI AQVVTENNKN  60
YLVLYASQTG TAEDYAKKFS KELVAKFNLN VMCADVENYD FESLNDVPVI VSIFISTYGE  120
GDFPDGAVNF EDFICNAEAG ALSNLRYNMF GLGNSTYEFF NGAAKKAEKH LSAAGAIRLG  180
KLGEADDGAG TTDEDYMAWK DSILEVLKDE LHLDEQEAKF TSQFQYTVLN EITDSMSLGE  240
PSAHYLPSHQ LNRNADGIQL GPFDLSQPYI APIVKSRELF SSNDRNCIHS EFDLSGSNIK  300
YSTGDHLAVW PSNPLEKVEQ FLSIFNLDPE TIFDLKPLDP TVKVPFPTPT TIGAAIKHYL  360
EITGPVSRQL FSSLIQFAPN ADVKEKLTLL SKDKDQFAVE ITSKYFNIAD ALKYLSDGAK  420
WDTVPMQFLV ESVPQMTPRY YSISSSSLSE KQTVHVTSIV ENFPNPELPD APPVVGVTTN  480
LLRNIQLAQN NVNIAETNLP VHYDLNGPRK LFANYKLPVH VRRSNFRLPS NPSTPVIMIG  540
PGTGVAPFRG FIRERVAFLE SQKKGGNNVS LGKHILFYGS RNTDDFLYQD EWPEYAKKLD  600
GSFEMVVAHS RLPNTKKVYV QDKLKDYEDQ VFEMINNGAF IYVCGDAKGM AKGVSTALVG  660
ILSRGKSITT DEATELIKML KTSGRYQEDV W                                 691

SEQ ID NO: 37         moltype = AA  length = 695
FEATURE               Location/Qualifiers
source                1..695
                      mol_type = protein
                      organism = Aspergillus niger
SEQUENCE: 37
MAQLDTLDLV VLAVLLVGSV AYFTKGTYWA VAKDPYASTG PAMNGAAKAG KTRNIIEKME  60
ETGKNCVIFY GSQTGTAEDY ASRLAKEGSQ RFGLKTMVAD LEEYDYENLD QFPEDKVAVF  120
VLATYGEGEP TDNAVEFYQF FTGDDVAFES GASADEKPLS KLKYVAFGLG NNTYEHYNAM  180
VRQVDAAFQK LGAQRIGSAG EGDDGAGTME EDFLAWKEPM WAALSESMDL QEREAVYEPV  240
FCVTENESLS PEDESVYLGE PTQSHLQGTP KGPYSAHNPF IAPIAESREL FTVKDRNCLH  300
MEISIAGSNL SYQTGDHIAV WPTNAGAEVD RFLQVFGLEG KRDSVINIKG IDVTAKVPIP  360
TPTTYDAAVR YYMEVCAPVS RQFVATLAAF APDEESKAEI VRLGSDKDYF HEKVTNQCFN  420
IAQALQSITS KPFSAVPFSL LIEGITKLQP RYYSISSSSL VQKDKISITA VVESVRLPGA  480
SHMVKGVTTN YLLALKQKQN GDPSPDPHGL TYSITGPRNK YDGIHVPVHV RHSNFKLPSD  540
PSRPIIMVGP GTGVAPFRGF IQERAALAAK GEKVGPTVLF FGCRKSDEDF LYKDEWKTYQ  600
DQLGDNLKII TAFSREGPQK VYVQHRLREH SELVSDLLKQ KATFYVCGDA ANMAREVNLV  660
LGQIIAAQRG LPAEKGEEMV KHMRSSGSYQ EDVWS                             695

SEQ ID NO: 38         moltype = AA  length = 1351
FEATURE               Location/Qualifiers
source                1..1351
                      mol_type = protein
                      organism = Psilocybe cyanescens
SEQUENCE: 38
MTDPNRTTFS SALHPLAVVS MASSSSDVFV LGLGVVLAAL YIFRDQLFAA SKPKVAPVST  60
TKPANGSANP RDFIAKMKQG KKRIVIFYGS QTGTAEEYAI RLAKEAKQKF GLASLVCDPE  120
EYDFEKLDQL PEDSIAFFVV ATYGEGEPTD NAVQLLQNLQ DDSFEFSNGE RKLSGLKYVV  180
```

-continued

```
FGLGNKTYEH YNLIGRTVDA QLAKMGAVRV GERGEGDDDK SMEEDYLEWK DGMWDAFAAA  240
MGVEEGQGGD SADFVVSELE SHPPEKVYLG EYSARALTKT KGIHDAKNPL AAPITVAREL  300
FQSVVDRNCV HVEFNIEGSG ITYQHGDHVG LWPLNPDVEV ERLLCVLGLT EKRDAVISIE  360
SLDPALAKVP FPVPTTYAAV LRHYIDVSAV AGRQILGTLS KFAPTPEAEA FLKNLNTNKE  420
EYHNVVANGC LKLGEILQVA TGNDITVAPT PGNTTKWPIP FDIIVSAIPR LQPRYYSISS  480
SPKVHPNTIH ATVVVLKYEN VPTDPIPRKW VYGVGSNFLL NLKHAINKEP VPFITQNGEQ  540
RVGVPEYLIA GPRGSYKTES HFKAPIHVRR STFRLPTNPK SPVIMIGPGT GVAPFRGFVQ  600
ERVALARRSV EKNGPESLND WGRISLFYGC RRSDEDFLYK DEWPQYQEEL KGKFKLHCAF  660
SRENYKPDGS KIYVQDLIWE DREHIADAIL NGKGYVYICG EAKSMSKQVE EVLARILGEA  720
KGGSGAVEGV AEIKLLKERS RLMLDYELAF RKFSQLQFAR VATFAMLRSS FSLQRLFSTS  780
SALRNVQRPI RDHLQKQDAP WEPRVAESAQ SVSEEILKAQ TPLQVPTNAK ATTSDSRTDS  840
REPLTAYDLQ LVKKRVREWS EQAMIALRNR ADDFTAHTKT TFSQLGLQLN RVTGYEEIEA  900
LKRGVVEQEE RINVARQAAR KAKVAYEEAV VQRSNSQREV NDLLQRKSSW MDSDVGRFTT  960
LVRQDHLYEQ EEARAKAAVE ETEEAVDREF SKLLRTILAR YHEEQVWSDK IRSASTYGSL  1020
AALGLNMLVF IMAIVVVEPW KRRRLAQTFE RKIEELSEEN GIKLDATMLS IAQQIEQQVN  1080
LIGSLKDDIS RNAPVIPEPA QEVRAETEIE EETSPFVSLE FLPLSRRQLE VAAVGAGAFA  1140
SNLWFGFGDD ALELLMLSTR ANKVPPRNLS RIHMTSFIIK AHEDRPTNST WKQDLECAFC  1200
RIIRGELPAS KVYENDKVIA ILDIMPLRKG HTLVIPKAHI SRLSELPSEL ASSVGEAVCK  1260
VAHALTQALD NTGLNVVCNQ EYAQAVPHVH YHVIPAPKFG YPGHGVESTN GVVGGKAPLT  1320
HREMHQKEFE AREELDDDDA KVLLKSIRAR L                                1351

SEQ ID NO: 39           moltype = AA  length = 592
FEATURE                 Location/Qualifiers
source                  1..592
                        mol_type = protein
                        organism = Psilocybe cyanescens
SEQUENCE: 39
MSVSEDDHRG LLIVYATETG NAQDAADYIA RQCRRIAFQC RVVNIDSFLL PDLLSETIVI  60
FVVSTTGSGV EPRSMTPLWT SLLRGDLPTD TFEDLYFSVF GLGDTAYEKF CWAAKKLSRR  120
LESIGGIEFY MRGEGDEQHP LGIDGALQPW TDGLINKLLE VAPLPPGEEI KPINDVPLPR  180
VLLKDTSKTA LNHSADPLKS DLQYHKAIVK KNDRITAADW YQDVRHLVFD FQDNIQYSPG  240
DVAVIHPVAL EHDVDAFLVT MSWQNIADEP FEIEQAMYDQ SLPDHLPPIT TLRTLFTRFL  300
DFNAVPRRSF FQYLRYFTSD EREQEKLDEF LSAAGADELY EYCYRVRRTI HEVLSEFRHV  360
KIPKGYIFDV FPPLRPREFS IASSIKTHLH QIHLCVAIVK YRTKLKIPRK GVCTYYLSIL  420
KPGDTLLVGI RRGLLRLPGK NDTPVIFIGP GTGIAPMRSA IEQRIANGCH ENTLYFGCRS  480
ASKDQHYGSE WQAYAANQEL KYRSAFSRDG VEGEARVYVQ DLIRQDSERI WDLVGHHKAW  540
VLVSGSSNKM PAAVKDAVAY AVEKYGGLSA EEAKEYVHLM VKEGRLIEEC WS          592

SEQ ID NO: 40           moltype = AA  length = 1063
FEATURE                 Location/Qualifiers
source                  1..1063
                        mol_type = protein
                        organism = Psilocybe cyanescens
SEQUENCE: 40
MSLNGSGLLT PSSEVTLSSP STPVLIYTFP QSNGTRPKSP VYIHIDDPGV QVSTLVEYIS  60
SQPENSSSVY IYDVAEQVGF GTSTKQWAKQ GLDISPVVDL QTRAGAGLSL VGRLSQGTSI  120
DAVKGTVLTA YTTPSGLALM APSFAYLPVP SSTTRLIIQV PTVTPVGETL TLSPTLSPLA  180
SVWSILPENV AVLLSSSPQQ TVDFATLAYK VIDSHIVHLF DHHSSAREIG RTFTPLTTIG  240
KSGLTLQEAV KQAGYEPLEY HGDPEAKTIV VLLNSSLALS LKAAVSVGTS GLGVVVVNVL  300
RPWDEAAIQT IIPSSATIVH VLDDVPNAVT QGSLYVDVFS ALWSTTPKRS VHSHRITPSQ  360
TQKFIAAGGE FLRFVEEVTH IAVSEPSVAS IKKTLFFSVP DSPLALLSRF VQELFLTKRT  420
ISSRHLTDYD VYSKPGGISA QRLLISRDKS TDNVPVQAIL PLDPNSVGHS DFLGVLDHNL  480
LKTHSLLKHA KKGSIVVVAS PWTPDEFSAN ITYEVAEVIT SRQLSVYTID VKSIANDLEL  540
FIQEQKIEKG EAQVLLFEFV FLRFYLGAAA TEQAIIQLMS VLFDDIDLTK FSAAAWLGLK  600
PVVVALPEVT PSDSPTLKEF EANAIAVETS EGQTVVNGAR LSTWHDAAKH LLFPSAFSPP  660
TDPDSLSNPA LRPEVPDTTF LVTCTVNKRL TPLEYDRNVF HLEFDTSGTG LKYAIGEALG  720
VHGWNDEQEV LDFCEWYGVD PDRLITIPVI GSDDGKMHTR TVLQALQQQI DLFGRPPKSF  780
YTDLAEYATV DVDRYALRFI GSPEGVSTFK KMSEKDTVSF GDVLKKYKSA RPGIERLCEL  840
IGDIKPRHYS IASAQSVVGD RVDLLVVTVD WLTPEGSPRY GQCTRYLAGL KIGQKVTVSI  900
KPSVMKLPPN LKQPLIMAGL GTGAAPFRAF LQHLAWLASK GEEIGPVFYY FGSRYQAAEY  960
LYGEEIEAFI LGGVITRAGL AFSRDGPKKV YIQHKMLEDS ETLAKMLHDD DGVFYLCGPT  1020
WPVPDVYEAL VNALVKYKGS DPVKAGEYLE SLKEEERYVL EVY                   1063

SEQ ID NO: 41           moltype = AA  length = 362
FEATURE                 Location/Qualifiers
source                  1..362
                        mol_type = protein
                        organism = Psilocybe cubensis
SEQUENCE: 41
MAFDLKTEDG LITYLTKHLS LDVDTSGVKR LSGGFVNVTW RIKLNAPYQG HTSIILKHAQ  60
PHMSTDEDFK IGVERSVYEY QAIKLMMANR EVLGGVDGIV SVPEGLNYDL ENNALIMQDV  120
GKMKTLLDYV TAKPPLATDI ARLVGTEIGG FVARLHNIGR ERRDDPEFKF FSGNIVGRTT  180
SDQLYQTIIP NAAKYGVDDP LLPTVVKDLV DDVMHSEETL VMADLWSGNI LLQLEEGNPS  240
KLQKIYILDW ELCKYGPASL DLGYFLGDCY LISRFQDEQV GTTMRQAYLQ SYARTSKHSI  300
NYAKVTAGIA AHIVMWTDFM QWGSEEERIN FVKKGVAAFH DARGNNDNGE ITSTLLKESS  360
TA                                                                362

SEQ ID NO: 42           moltype = AA  length = 362
FEATURE                 Location/Qualifiers
```

-continued

```
source                1..362
                      mol_type = protein
                      organism = Psilocybe cyanescens
SEQUENCE: 42
MAFDLKTPEG LLLYLTRHLS LDVDPSGVKR LSGGFVNVTW RIRLNAPYQG HTSIILKHAQ  60
PHLSSDEDFK IGVERSAYEY QALKVMSANQ EVLGGDDSRV SVPEGLHYDV ENNALIMQDV  120
GTMKTLLDYA TAKPPLSTEI ASLVGTEIGA FIARLHNLGR KRRDQPAFKF FSGNIVGRTT  180
ADQLYQTIIP NAAKYGINDP LLPTVVKDLV GEVMNSEETL IMADLWSGNI LLEFVEGNPS  240
ELKKIWLVDW ELCKYGPASL DMGYFLGDCY LIARFQDELV GTTMRKAYLK GYARTAKGTI  300
NYSKVTASIG AHLVMWTDFM KWGNYEEREE FVKKGVEALH DAWEDNNDGE ITSVLVNEAS  360
ST                                                                 362

SEQ ID NO: 43         moltype = AA  length = 362
FEATURE               Location/Qualifiers
source                1..362
                      mol_type = protein
                      organism = Psilocybe cyanescens
SEQUENCE: 43
MAFDLKTVEG LIVYLTKCLS LEVDSSGVKR LSGGFVNVTW RIRLNAPYQG HTSIILKHAQ  60
PHMSTDKDFK IGVERSVYEY QALKVISANR EALGGIDSRV SAPEGLHYDV ENNALIMQDV  120
GTLKTLMDYV IEKPAISTEM ARLIGTEIGD FVARLHSIGR QKRDQPDFKF FSGNIVGRTT  180
ADQLYQTILP NTAKYGIDDP LLPTVVKDLV DEAMQSEETL IMADLWTGNI LVEFEEGNLS  240
VLKKIWLVDW ELCKYGPVRL DMGYFLGDCF LISRFKNEQV AKAMRQAFLQ RYNRVSDTPI  300
NYSVATTGIA AHIVMWTDFM NWGTEEERKE YVKKGVAGIH DGRNHNVDGE ITSILMQEAS  360
TA                                                                 362

SEQ ID NO: 44         moltype = AA  length = 360
FEATURE               Location/Qualifiers
source                1..360
                      mol_type = protein
                      organism = Gymnopilus dilepis
SEQUENCE: 44
MTFDLKTEEG LLVYLTQHLS LDVDLDGLKR LSGGFVNITW RIRLNAPFKG YTNIILKHAQ  60
PHLSSDENFK IGVERSAYEY RALKIVSESP ILSGDDNLVF VPQSLHYDVV HNALIVQDVG  120
SLKTLMDYVT ARPSLSSEMA KLVGGQIGAF IARLHNIGRE NKDHPEFNFF SGNIVGRTTA  180
VQLYETIVPN ATKYDIDDPI IPVVVQELIE EVKGSDETLI MADLWGGNIL LEFGKDSSDL  240
GKIWVVDWEL CKYGPPSLDM GYFLGDCFLL AQFQDEKVAT AMRRAYLENY AKIAKVPMDY  300
DRSTTGIGAH LVMWTDFMNW GSDEERKTSV EKGVRAFHDA KRDNKEGEIP SILLRESSRT  360

SEQ ID NO: 45         moltype = AA  length = 622
FEATURE               Location/Qualifiers
source                1..622
                      mol_type = protein
                      organism = Saccharomyces cerevisiae
SEQUENCE: 45
MLFYSFVWSV LAASVALAKT HKLNYTASWV TANPDGLHEK RMIGFNGEWP LPDIHVEKGD  60
RVELYLTNGF QDNTATSLHF HGLFQNTSLG NQLQMDGPSM VTQCPIVPGQ TYLYNFTVPE  120
QVGTFWYHAH MGAQYGDGMR GAFIIHDPEE PFEYDHERVI TLSDHYHENY KTVTKEFLSR  180
YNPTGAEPIP QNILFNNTMN VTLDFTPGET YLFRFLNVGL FVSQYIILED HEMSIVEVDG  240
VYVKPNFTDS IYLSAGQRMS VLIKAKDKMP TRNYAMMQIM DETMLDVVPP ELQLNQTIQM  300
RYGHSLPEAR ALNIEDCDLD RATNDFYLEP LIERDLLAHY DHQIVMDVRM VNLGDGVKYA  360
FFNNITYVTP KVPTLTTLLT SGKLASDPRI YGDNINAQLL KHNDIIEVVL NNYDSGRHPF  420
HLHGHNFQIV QKSPGFHVDE AYDESEQDEM TVPYNESAPL QPFPERPMVR DTVVLEPSGH  480
VVLRFRADNP GVWYFHCHVD WHLQQGLASV FIEAPVLLQE REKLNENYLD ICKAADIPVV  540
GNAAGHSNDW FDLKGLPRQP EPLPKGFTTE GYLALIISTI IGVWGLYSIA QYGIGEVIPN  600
DEKVYHTLRE ILAENEIEVS RG                                           622

SEQ ID NO: 46         moltype = AA  length = 207
FEATURE               Location/Qualifiers
source                1..207
                      mol_type = protein
                      organism = Bos taurus
SEQUENCE: 46
MSTPSIHCLK PSPLHLPSGI PGSPGRQRRH TLPANEFRCL TPKDAAGVFE IEREAFISVS  60
GNCPLNLDEV RHFLTLCPEL SLGWFVEGRL VAFIIGSLWD EERLTQESLT LHRPGGRTAH  120
LHALAVHHSF RQQGKGSVLL WRYLQHAGGQ PAVRRAVLMC EDALVPFYQR FGFHPAGPCA  180
VVVGSLTFTE MHCSLRGHAA LRRNSDR                                      207

SEQ ID NO: 47         moltype = AA  length = 499
FEATURE               Location/Qualifiers
source                1..499
                      mol_type = protein
                      organism = Schistosoma mansoni
SEQUENCE: 47
MISTESDLRR QLDENVRSEA DESTKEECPY INAVQSHHQN VQEMSIIISL VKNMNDMKSI  60
ISIFTDRNIN ILHIESRLGR LNMKKHTEKS EFEPLELLVH VEVPCIEVER LLEELKSFSS  120
YRIVQNPLMN LPEAKNPTLD DKVPWFPRHI SDLDKVSNSV LMYGKELDAD HPGFKDKEYR  180
KRRMMFADIA LNYKWGQQIP IVEYTEIEKT TWGRIYRELT RLYKTSACHE FQKNLGLLQD  240
KAGYNEFDLP QLQVVSDFLK ARTGFCLRPV AGYLSARDFL SGLAFRVFYC TQYIRHQADP  300
```

-continued

```
FYTPEPDCCH ELLGHVPMLA DPKFARFSQE IGLASLGTSD EEIKKLATCY FFTIEFGLCR  360
QDNQLKAYGA GLLSSVAELQ HALSDKAVIK PFIPMKVINE ECLVTTFQNG YFETSSFEDA  420
TRQMREFVRT IKRPFDVHYN PYTQSIEIIK TPKSVAKLVQ DLQFELTAIN ESLLKMNKEI  480
RSQQFTTNKI VTENRSSGS                                               499

SEQ ID NO: 48           moltype = AA  length = 345
FEATURE                 Location/Qualifiers
source                  1..345
                        mol_type = protein
                        organism = Homo sapiens
SEQUENCE: 48
MGSSEDQAYR LLNDYANGFM VSQVLFAACE LGVFDLLAEA PGPLDVAAVA AGVRASAHGT  60
ELLLDICVSL KLLKVETRGG KAFYRNTELS SDYLTTVSPT SQCSMLKYMG RTSYRCWGHL  120
ADAVREGRNQ YLETFGVPAE ELFTAIYRSE GERLQFMQAL QEVWSVNGRS VLTAFDLSVF  180
PLMCDLGGGA GALAKECMSL YPGCKITVFD IPEVVWTAKQ HFSFQEEEQI DFQEGDFFKD  240
PLPEADLYIL ARVLHDWADG KCSHLLERIY HTCKPGGGIL VIESLLDEDR RGPLLTQLYS  300
LNMLVQTEGQ ERTPTHYHML LSSAGFRDFQ FKKTGAIYDA ILARK                  345

SEQ ID NO: 49           moltype = AA  length = 356
FEATURE                 Location/Qualifiers
source                  1..356
                        mol_type = protein
                        organism = Tabernanthe iboga
SEQUENCE: 49
DAMKSAELFK AQAHIFKQVF CFTNGASLKC AVQLGIPDAI DNHGKAMTLS ELTDALPINP  60
SKAPHIHRLM RILVTAGFFV EERLGNGKEE KANGYALTPS SRLLLKNKPL SLRASALTML  120
DPVTVKTWNA LSEWFQNEDQ TAFETAHGKN MWDFFAEDPG LSKKFNESMA SDSQLVTEVL  180
VTKCKFVFEG LTSMVDVGGG TGTVAGAIAK TFPSLRCTVF DLPHVVANLE PTENLDFVAG  240
DMFGKIPPAN AIFLKWVLHD WNDEDCVKIL KNCKRAIPGK EKGGKVIIVD IIMETEKHDI  300
DEFDYAKMCM DMEMLVLCNS KERTEKELAM LVSEAGFSGY KIFPVLGIRS LIEVYP      356
```

PROCESSES FOR THE PRODUCTION OF TRYPTAMINES

CROSS-REFERENCE

This application is a continuation application of U.S. application Ser. No. 17/012,737, filed Sep. 4, 2020, now U.S. Pat. No. 11,661,617, which is a continuation application of International Application No. PCT/US2019/021489, filed Mar. 8, 2019, which claims the benefit of U.S. Provisional Application No. 62/640,443, filed Mar. 8, 2018, the entireties of each of which are hereby expressly incorporated by reference for all purposes.

SEQUENCE LISTING

The instant application contains a Sequence Listing which has been submitted electronically in XML format and is hereby incorporated by reference in its entirety. Said XML file, created on Apr. 17, 2023, is named COPA_044_03US_SeqList_ST26.xml and is 82,706 bytes in size.

BACKGROUND

Tryptamine is a monoamine alkaloid. It contains an indole ring structure, and is structurally similar to the amino acid tryptophan, from which the name derives. Tryptamine is found in trace amounts in the brains of mammals and is hypothesized to play a role as a neuromodulator or a neurotransmitter. Tryptamine is the common functional group in a set of compounds, termed collectively, substituted tryptamines. This set includes many biologically active compounds, including neurotransmitters and psychotropic drugs.

SUMMARY

In one aspect, a microbial cell that produces a tryptamine is provided, the microbial cell containing therein one or more heterologous nucleic acid sequences encoding one or more enzymes involved in a biosynthesis pathway that converts an anthranilate to a tryptamine.

In another aspect, a microbial cell that produces a tryptamine is provided, the microbial cell containing therein one or more heterologous nucleic acid sequences encoding one or more enzymes involved in a biosynthesis pathway that converts an indole to a tryptamine.

In another aspect, a microbial cell that produces a tryptamine is provided, the microbial cell containing therein one or more heterologous nucleic acid sequences encoding one or more enzymes involved in a biosynthesis pathway that converts tryptophan to a tryptamine.

In some cases, the anthranilate is a substituted anthranilate. In some cases, the anthranilate is:

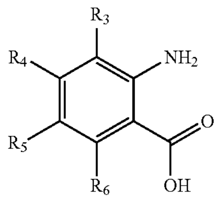

where:

each R is independently a hydrogen, a halogen, —OH, $C_1$-$C_5$ alkyl, $C_1$-$C_5$ alkoxy, $NO_2$, NH, COOH, CN, sulfur, $SO_3$, $SO_4$, or $PO_4$.

In some cases, the indole is a substituted indole. In some cases, the indole is:

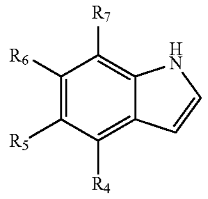

where:

each R is independently a halogen, —OH, $C_1$-$C_5$ alkyl, $C_1$-$C_5$ alkoxy, $NO_2$, NH, COOH, CN, sulfur, $SO_3$, $SO_4$, or $PO_4$.

In some cases, the tryptamine is a substituted tryptamine. In some cases, the tryptamine is:

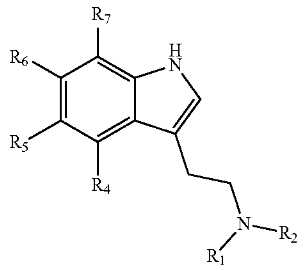

where:

each R is independently a hydrogen, a halogen, —OH, $C_1$-$C_5$ alkyl, $C_1$-$C_5$ alkoxy, $NO_2$, NH, COOH, CN, sulfur, $SO_3$, $SO_4$, or $PO_4$.

In some cases, the one or more enzymes comprise one or more of: trpD, trpB, trpC, and trpA. In some cases, the one or more heterologous nucleic acid sequences comprises a multicistronic operon encoding at least two of trpD, trpB, trpC, and trpA. In some cases, the multicistronic operon has a nucleic acid sequence having at least 80% sequence identity to any one of SEQ ID NOs: 1-4. In some cases, the trpD comprises an amino acid sequence having at least 80% sequence identity to any one of SEQ ID NOs: 5-7. In some cases, the trpC comprises an amino acid sequence having at least 80% sequence identity to any one of SEQ ID NOs: 8 and 9. In some cases, the trpB comprises an amino acid sequence having at least 80% sequence identity to any one of SEQ ID NOs: 10 and 11. In some cases, the trpA comprises an amino acid sequence having at least 80% sequence identity to any one of SEQ ID NOs: 12 and 13. In some cases, the one or more enzymes comprise a decarboxylase. In some cases, the decarboxylase is a tryptophan decarboxylase. In some cases, the tryptophan decarboxylase comprises an amino acid sequence having at least 50%, at least 60%, at least 70%, at least 80%, at least 90%, or at least 95% sequence identity to any one of SEQ ID NOs: 14-20. In some cases, the one or more enzymes comprise a transferase. In some cases, the transferase is selected from the group consisting of: tryptamine N-methyltransferase, tryptamine benzoyl transferase, serotonin N-acetyltransferase, dopamine N-acetyltransferase, arylalkylamine N-acetyltransferase, and tryptamine hydroxycinnamoyltransferase. In some cases, the transferase comprises an amino acid sequence having at least 50% sequence identity to any one of SEQ ID NOs: 21-31 or 46. In some cases, the one or more enzymes comprise tryptamine 4-hydroxylase. In some cases, the tryptamine 4-hydroxylase comprises an amino acid sequence having at least 50%, at least 60%, at least 70%, at least 80%, at least 90%, or at least 95% sequence identity to any one of SEQ ID NOs: 32-35. In some cases, the one or more enzymes comprises a P450 reductase. In some cases, the P450 reductase comprises an amino acid sequence having at least 50%, at least 60%, at least 70%, at least 80, at least 90%, or at least 95% sequence identity to any one of SEQ ID NOs: 36-40. In some cases, the one or more enzymes comprises a kinase. In some cases, the kinase comprises an amino acid sequence having at least 50%, at least 60%, at least 70%, at least 80%, at least 90%, or at least 95% sequence identity to any one of SEQ ID NOs: 41-44. In some cases, the anthranilate is biosynthetically produced by the microbial cell. In some cases, the anthranilate is fed to the engineered microbial cell. In some cases, the anthranilate is 5-bromoanthranilate, 6-hydroxyanthranilate, 5-hydroxyanthranilate, 6-chloroanthranilate, or 5-chloroanthranilate. In some cases, the indole is biosynthetically produced by the microbial cell. In some cases, the indole is fed to the engineered microbial cell. In some cases, the indole is selected from the group consisting of: 5-hydroxyindole, 4-hydroxyindole, 7-hydroxyindole, and 4-chloroindole, 5-bromoindole, or 4-fluoroindole. In some cases, the microbial cell secretes the tryptamine in culture broth. In some cases, the tryptamine is selected from any tryptamine described in FIG. 4, FIG. 6, or FIG. 8. In some cases, the tryptamine is selected from the group consisting of: tryptamine, 5-hydroxytryptamine, 5-hydroxymethyltryptamine, 5-hydroxy-N,N-dimethyltryptamine, 5-phosphoryloxymethyltryptamine, 5-phosphoryloxy-N,N-dimethyltryptamine, 4-hydroxytryptamine, 4-hydroxy-N,N-dimethyltryptamine, 4-phosphoryloxytryptamine, 4-phosphoryloxy-N,N-tryptamine, 7-hydroxytryptamine, 7-phosphoryloxymethyltryptamine, 7-phosphoryloxy-N,N-dimethyltryptamine, 4-chloro-tryptamine, 4-chloro-N,N-dimethyltryptamine, 5-bromotryptamine, 5-bromo-methyltryptamine, 5-bromo-N-methyltryptamine, 5-bromo-N,N-dimethyltryptamine, N-acetyl-tryptamine, 4-hydroxy-N-acetyl-tryptamine. In some cases, the microbial cell is a eukaryotic cell. In some cases, the microbial cell is a yeast cell. In some cases, the yeast cell is of the species *Saccharomyces cerevisiae*. In some cases, the yeast cell does not express one or more of aromatic aminotransferase I (aro8) and phenylpyruvate decarboxylase (aro10). In some cases, the yeast cell overexpresses one or more of phosphoribosylanthranilate isomerase (TRP1), anthranilate synthase (TRP2), indole-3-glycerolphosphate synthase (TRP3), anthranilate phosphoribosyl transferase (TRP4), and tryptophan synthase (TRP5). In some cases, the yeast cell overexpresses a mutant of one or more of phosphoribosylanthranilate isomerase (TRP1), anthranilate synthase (TRP2), indole-3-glycerolphosphate synthase (TRP3), anthranilate phosphoribosyl transferase (TRP4), and tryptophan synthase (TRP5). In some cases, the yeast cell has two or more copies of the one or more heterologous nucleic acid sequences and they act synergistically. In some cases, the microbial cell is a prokaryote. In some cases, the microbial cell is a bacterial cell. In some cases, the bacterial cell is of the species *Escherichia coli* or *Corynebacterium glutamicum*. In some cases, the bacterial cell does not express one or more of tryptophanase (tna), tryptophan repressor element (trpR), or anthranilate synthase (trpE) genes. In some cases, at least one copy of the one or more heterologous nucleic acid sequences is stably integrated into the genome of the microbial cell. In some cases, two or more copies of the one or more heterologous nucleic acid sequences are stably integrated into the genome of the microbial cell. In some cases, the two or more copies of the one or more heterologous nucleic acid sequences are from a same sequence. In some cases, the two or more copies of the one or more heterologous nucleic acid sequences are from a distinct sequence.

In another aspect, a method for synthesizing a tryptamine is provided, the method comprising: culturing a microbial cell according to any of the preceding in a presence of anthranilate, thereby synthesizing the tryptamine. In some cases, the method further comprises feeding the anthranilate to the microbial cell. In some cases, the anthranilate is produced biosynthetically by the microbial cell. In some cases, the anthranilate is a substituted anthranilate.

In another aspect, a method for synthesizing a tryptamine is provided, the method comprising: culturing a microbial cell according to any of the preceding in a presence of indole, thereby synthesizing the tryptamine. In some cases, the method further comprises feeding the indole to the microbial cell. In some cases, the indole is produced biosynthetically by the microbial cell. In some cases, the indole is a substituted indole.

In another aspect, a method for synthesizing a tryptamine is provided, the method comprising: culturing a microbial cell of any of the preceding in a presence of tryptophan, thereby synthesizing the tryptamine. In some cases, the method further comprises feeding the tryptophan to the microbial cell. In some cases, the tryptophan is produced biosynthetically by the microbial cell.

In some cases, any method of the preceding further comprises purifying the tryptamine from the culture.

In another aspect, a microbial cell is provided containing therein one or more heterologous nucleic acid sequences encoding one or more enzymes involved in a biosynthesis pathway to convert a tryptamine to a tryptamine derivative. In some cases, the one or more enzymes comprise a tryptamine 4-hydroxylase. In some cases, tryptamine 4-hydroxylase comprises an amino acid sequence having at least 50%, at least 60%, at least 70%, at least 80%, at least 90%, or at least 95% sequence identity to any one of SEQ ID NOs:32-35. In some cases, the one or more enzymes comprise a tryptamine 5-hydroxylase. In some cases, the tryptamine 5-hydroxylase comprises an amino acid sequence having at least 50%, at least 60%, at least 70%, at least 80%, at least 90%, or at least 95% sequence identity to SEQ ID NO:47. In some cases, the one or more enzymes comprise a 4-hydroxytryptamine kinase. In some cases, the 4-hydroxytryptamine kinase comprises has an amino acid sequence having at least 50%, at least 60%, at least 70%, at least 80%, at least 90%, or at least 95% sequence identity according to any one of SEQ ID NOs:41-44. In some cases, the tryptamine is a substituted tryptamine. In some cases, the tryptamine is selected from the group consisting of: 5-methoxy-N,N-dimethyl-tryptamine, N,N-diisopropyl-tryptamine, N-methyl-N-isopropyltryptamine, N,N-dimethyltryptamine, N,N-tetramethylenetryptamine, N,N-dipropyltryptamine, 4-hydroxy-N,N-dimethyltryptamine, tryptamine, 4-hydroxytryptamine, 5-hydroxytryptamine, ibogamine, 4-hydroxyibogamine, and 5-hydroxyibogamine. In some cases, the tryptamine derivative is any tryptamine derivative described in FIG. 16. In some cases, the tryptamine derivative is selected from the group consisting of: 5-hydroxy-N,N-diisopropyl-tryptamine, 5-hydroxy-N-methyl-N-isopropyltryptamine, 5-hydroxy-N,N-dimethyltryptamine, 5-hydroxy-N,N-tetramethylenetryptamine, 5-hydroxy-N,N-dipropyltryptamine, 4,5-methoxy-N,N-dimethyl-tryptamine, 4-hydroxy-N,N-diisopropyl-tryptamine, 4-hydroxy-N-methyl-N-isopropyltryptamine, 4-hydroxy-N,N-dimethyltryptamine, 4-hydroxy-N,N-tetramethylenetryptamine, 4-hydroxy-N,N-dipropyltryptamine, 4-phosphoryloxy-N,N-dipropyltryptamine, 4-hydroxytryptamine, 5-hydroxytryptamine, 4-methoxytryptamine, 5-methoxytryptamine, 4-phosphoryloxytryptamine, 5-phosphoryloxytryptamine, 4-hydroxyibogamine, 5-hydroxyibogamine, 4-phosphoryloxyibogamine, and 5-phosphoryloxyibogamine.

In another aspect, a method of synthesizing a tryptamine derivate from a tryptamine is provided, the method comprising: culturing a microbial cell according to any of the preceding in a presence of a tryptamine, thereby synthesizing the tryptamine derivative. In some cases, the method further comprises purifying the tryptamine derivative from the culture.

In yet another aspect, a vector is provided comprising one or more heterologous nucleic acid sequences encoding one or more enzymes comprising an amino acid sequence having at least 50%, at least 60%, at least 70%, at least 80%, at least 90%, or at least 95% sequence identity to any one of SEQ ID NOs: 5-49.

In yet another aspect, a microbial cell is provided containing therein one or more heterologous nucleic acid sequences encoding an enzyme from a tryptamine synthesis pathway or a functional fragment thereof comprising an amino acid sequence having at least 50%, at least 60%, at least 70%, at least 80%, at least 90%, or at least 95% sequence identity to any one of SEQ ID NOs: 5-49.

In another aspect, a method is provided for screening for the levels of 4-hydroxytryptamine within any microbial cell of the preceding, the method comprising: detecting a color or a fluorescence product of the 4-hydroxytryptamine within the microbial cell. In some cases, the 4-hydroxytryptamine is oxidized within the microbial cell, thereby producing an oxidized 4-hydroxytryptamine. In some cases, the oxidized 4-hydroxytryptamine is directly proportional to a level of 4-hydroxytryptamine synthesized within the microbial cell. In some cases, an oxidation of the oxidized 4-hydroxytryptamine is catalyzed by iron sulphate. In some cases, an oxidation of the oxidized 4-hydroxytryptamine is catalyzed by an enzyme expressed by the microbial cell. In some cases, the enzyme comprises an amino acid sequence having at least 50%, at least 60%, at least 70%, at least 80%, at least 90%, or at least 95% sequence identity to SEQ ID NO: 45.

In another aspect, a method of converting an anthranilate to a tryptamine is provided, the method comprising incubating the anthranilate in a presence of one or more enzymes involved in a biosynthesis pathway that converts an anthranilate to a tryptamine.

In yet another aspect, a method of converting an indole to a tryptamine is provided, the method comprising incubating the indole in a presence of one or more enzymes involved in a biosynthesis pathway that converts an indole to a tryptamine.

In yet another aspect, a method of converting tryptophan to a tryptamine is provided, the method comprising incubating the tryptophan in a presence of one or more enzymes involved in a biosynthesis pathway that converts tryptophan to a tryptamine.

In yet another aspect, a method of converting a tryptamine to a derivatized tryptamine is provided, the method comprising incubating the tryptamine in a presence of one or more enzymes involved in a biosynthetic pathway that converts tryptamine to a derivatized tryptamine.

In some cases, a method of the preceding is performed in the absence of a biological cell. In some cases, a method of the preceding is performed under in vitro conditions. In some cases, a method of the preceding is performed under cell-free conditions. In some cases, a method of the preceding is performed in a cell lysate.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Some novel features of the invention are set forth in the appended claims. A better understanding of the features and advantages of the present invention will be obtained by reference to the following detailed description that sets forth illustrative embodiments, in which the principles of the invention are utilized, and the accompanying drawings of which:

FIG. 4 depicts non-limiting examples of substituted tryptamines produced by engineered bacterial cells fed with substituted anthranilate or indole compounds in accordance with embodiments of the disclosure.

FIG. 11 depicts a non-limiting example of tandem mass spectrometry (MS/MS) of N-acetyltryptamine derived from engineered yeast cells in accordance with embodiments of the disclosure.

FIG. 16 depicts a non-limiting example of the production of substituted tryptamines from fed tryptamines using engineered yeast in accordance with embodiments of the disclosure.

DETAILED DESCRIPTION

Figure 1:
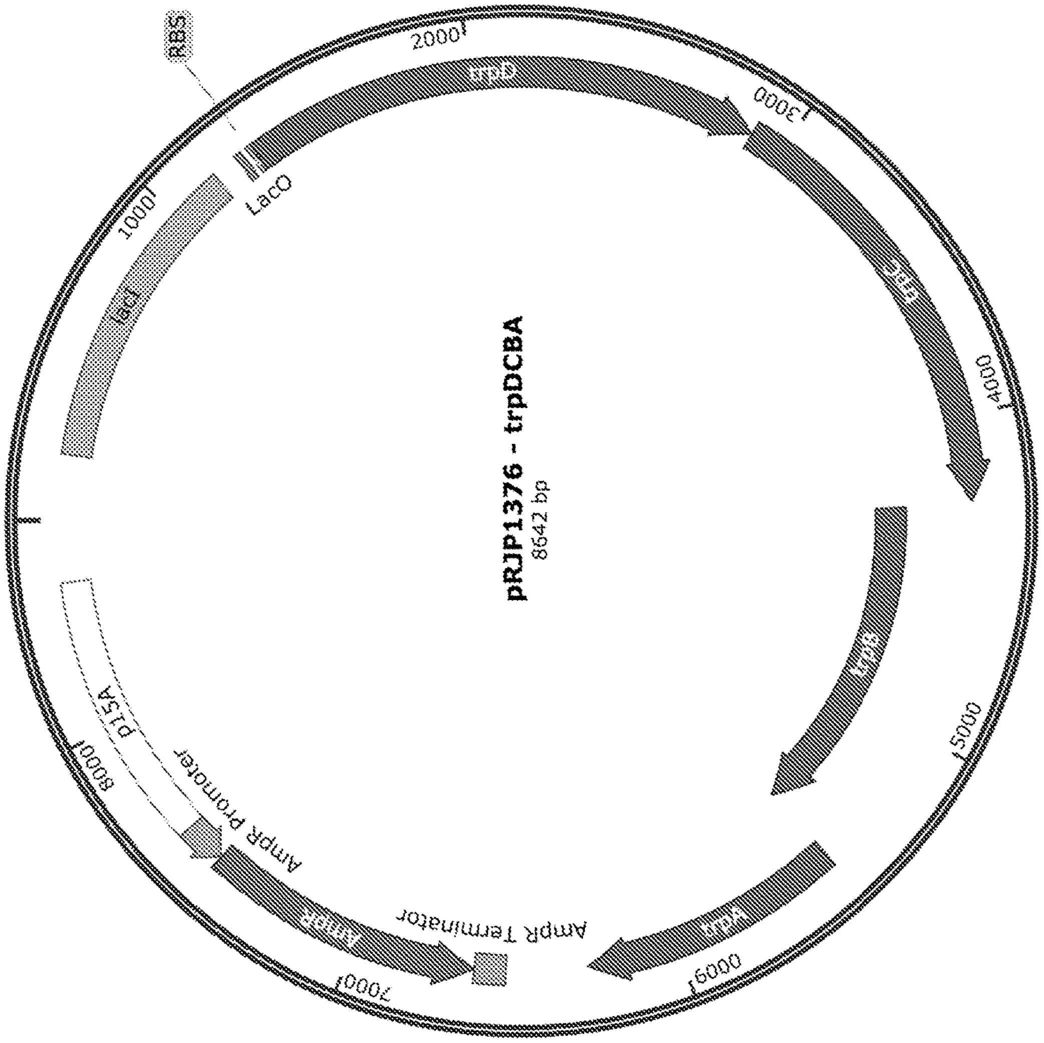
FIG. 1 depicts a non-limiting example of a plasmid map suitable for overexpression of the bacterial tryptophan operon in bacteria in accordance with embodiments of the disclosure. Plasmid is medium copy (p15a) and contains ampicillin resistance. TrpD, trpC, trpB and trpA are expressed in a multicistronic operon (e.g., SEQ ID NO: 1).

The present disclosure relates to microorganisms containing heterologous DNA useful in the production of tryptamines with 4-, 5-, 6-, or 7-indole substitutions, and/or R1 or R2 amine substitutions. Furthermore, this disclosure relates to processes for optimizing production, executing production, and recovering such substituted tryptamines. The disclosure provided herein provides processes for the production of various compounds, such as tryptamines. The disclosure further provides prokaryotic and eukaryotic microbes, including bacteria (e.g., *Escherichia coli*) and yeast (e.g., *Saccharomyces cerevisiae*), that may be genetically altered to contain heterologous sequences that encode biological molecules that can provide a biosynthetic pathway for the synthesis of tryptamine and/or substituted tryptamines in vivo. In some aspects, the disclosure provides microbes that may be engineered to contain plasmids and stable gene integrations containing sufficient genetic information for conversion of anthranilate or substituted anthranilates, and/or indole or substituted indoles, to a respective tryptamine or substituted tryptamine. The fermentative production of substituted tryptamines in a whole-cell biocatalyst may be useful for cost effective production of these compounds for therapeutic use.

Tryptamines are naturally occurring monoamine alkaloids derived from tryptophan, from which the name is derived. Analogs within the tryptamine family contain substitutions at the indole ring structure and the amine group. This family of compounds contains psychotropically active members, including N,N-dimethyltryptophan (DMT), 5-methoxy-N,N-dimethyltryptamine (5-MeO-DMT), 4-hydroxy dimethyltryptophan (psilocin) and its 4-O-phosphate ester, psilocybin (Hofmann et al. 1959). Psilocin may act as a partial agonist on 5HT1a, 5HT2a, and 5HT2c receptors (Hasler et al. 2004). Several basidiomycete fungi of the genus Psilocybe and other genera produce substituted tryptamines biosynthetically, including psilocybin, psilocin, norpsilocin, baeocystin, norbaeocystin and aeruginascin (Lenz, Wick, and Hoffmeister 2017). The compound N,N-dimethyltryptamine is ubiquitous in nature and is produced by many plants and animals (Carbonaro and Gatch 2016). Substituted tryptamines can also be synthetically derived, including the tryptans (e.g., Zolmitriptan and Sumatriptan), which are chemically synthesized and used as medications used to treat migraines and cluster headaches (Derry, Derry, and Moore 2014).

Tryptamines, such as psilocin, can cause profound changes in perception and mood in human subjects. Administration of high-dose psilocybin has been found to reliably induce mystical experiences leading to significant and enduring improvements in quality of life (Griffiths et al. 2006). Psilocybin administration has been concluded to be safe and well tolerated on 9 patients with severe, refractory obsessive-compulsive disorder and may be associated with "robust acute reductions" in core symptoms (Moreno et al. 2006).

Due to their complex structure, tryptamines and their respective substituted analogs are difficult to obtain commercially at economically feasible prices, if at all in large scale. Several organic chemistry methods exist for production of substituted tryptamines, including psilocybin. Dr. Albert Hoffmann originally published on the organics synthesis of psilocybin in 1958 (Hofmann et al. 1958). However, a dangerous reagent was used to phosphorylate the phosphate at the −4 position of the indole ring and later improvements were made for the synthesis (Hofmann, A. & Troxler, F. 1963. Esters of Indoles (U.S. Pat. No. 3,075,992), Basel, Switzerland: Sandoz Ltd.). This production method was adopted by Dr. David E Nichols for early clinical trials, but at a high cost for production (Nichols 2014).

Extraction of tryptamines from basidiomycete fungal tissue naturally producing the compounds is not suitable for large scale up production. The reported concentrations of psilocybin in mushrooms Psilocybe cubensis are less than 1% of the dry cell weight (J. Gartz 1994), causing a challenge for extraction and purification. Furthermore, the cultivation of such fungal tissue requires month-long time scales and would cause supply challenges (Jochen Gartz, Allen, and Merlin 1994). Furthermore, use of natural tissue precludes the ability to produce novel and unnatural tryptamine compounds with therapeutic properties.

The instant disclosure provides methods and materials to produce substituted tryptamines in high yield from inexpensive media components. The methods of the disclosure provide for production of tryptamine derivatives not naturally found in nature or tryptamine derivatives that are not accessible by synthetic chemistry. In some instances, the disclosed tryptamine derivatives may have favorable pharmacological effects (e.g., half-life, indications, etc). Additional advantages of the methods described herein include the use of a single biocatalyst for production of several substituted tryptamine analogues and a whole cell catalyst that is robust in fermentation and can regenerate itself for ease of use during production runs.

Accordingly, the objective of the present invention is to provide novel processes for the biosynthetic production of 4-, 5-, 6- or 7-indole substituted and/or R1 or R2 amine substituted tryptamines.

In some cases of the present disclosure, 4-, 5-, 6- or 7-indole substituted and/or R1 or R2 amine substituted tryptamines may be biosynthetically produced from corresponding substituted anthranilates and indoles by engineered microbial cells. Substituted anthranilates and indoles are widely available, vast in variety, and inexpensive compared to their respective substituted tryptamines.

In other aspects of the disclosure, a method of converting an anthranilate to a tryptamine is provided, the method comprising incubating the anthranilate in the presence of one or more enzymes involved in a biosynthesis pathway that converts an anthranilate to a tryptamine. In other aspects of the disclosure, a method of converting an indole to a tryptamine is provided, the method comprising incubating the indole in the presence of one or more enzymes involved in a biosynthesis pathway that converts an indole to a tryptamine. In other aspects of the disclosure, a method of converting tryptophan to a tryptamine is provided, the method comprising incubating the tryptophan in the presence of one or more enzymes involved in a biosynthesis pathway that converts tryptophan to a tryptamine. In other aspects of the disclosure, a method of converting a tryptamine to a derivatized tryptamine is provided, the method comprising incubating the tryptamine in the presence of one or more enzymes involved in a biosynthetic pathway that converts tryptamine to a derivatized tryptamine. In some cases, the methods may be performed within a biological cell (e.g., by an engineered microbial cell as described herein). In other cases, the methods may be performed in the absence of a biological cell. In some cases, the methods may be performed under in vitro conditions. In some cases, the methods may be performed under cell-free conditions. In some cases, the methods may be performed in a cell lysate.

Synthesis of a Substituted Tryptamine from a Substituted Anthranilate in Engineered Microbial Cells In an aspect of the disclosure, the processes described herein provide for the production of 4-, 5-, 6- or 7-indole substituted tryptamines with R1 or R2 substitutions at the amine. In some cases, anthranilate or an anthranilate substituted at 3- 4-, 5-, or 6- can be used to make 4-, 5-, 6- or 7-indole substituted tryptamines with R1 or R2 substitutions. In some cases, the process may be carried out in a whole-cell microbial fermentation. In some cases, an engineered microbial cell may be cultured in the presence of anthranilate or a substituted anthranilate (e.g., anthranilate or substituted anthranilate may be fed to or otherwise incubated with the microbial cell). In other cases, the anthranilate or substituted anthranilate may be produced biosynthetically by the microbial cell. For example, a microbial cell may produce anthranilate or a substituted anthranilate naturally (e.g., as part of central carbon metabolism). In other cases, the microbial cell may be engineered to produce anthranilate or a substituted anthranilate (e.g., by overexpressing enzymes for the production of substituted anthranilates).

Scheme 1 below depicts a non-limiting example of synthesis of a substituted tryptamine from anthranilate or a substituted anthranilate in an engineered microbial cell.

Scheme 1

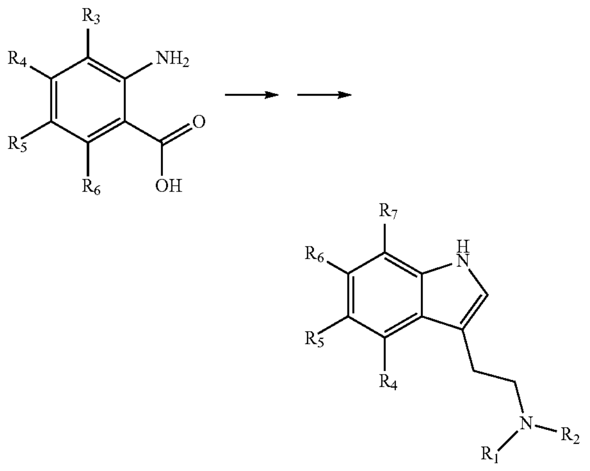

In some aspects, the disclosure provides a method for the production of substituted tryptamines by cultivating engineered microbes in the presence of anthranilate or a substituted anthranilate,

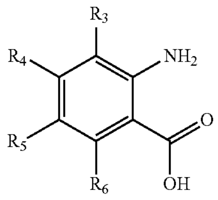

where —R is, but is not limited to, a halogen (—Br, —F, —Cl, —I, etc), —OH, C1-C5 alkyl, C1-C5 alkoxy, $NO_2$, NH, COOH, CN, sulfur, $SO_3$, $SO_4$, or $PO_4$. The resulting substituted tryptamine,

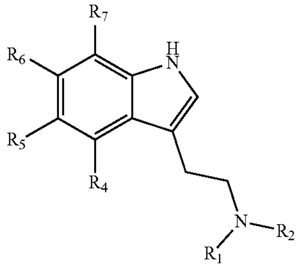

may be recovered from the culture broth. In some cases, the resulting tryptamine may be used in further downstream chemistry, taking advantage of chemical leaving groups or protecting groups incorporated into the tryptamine scaffold during the fermentative biosynthetic process.

In another aspect of the disclosure, indole or indole substituted at 4-, 5-, 6-, or 7- can be used to make 4-, 5-, 6-, or 7-indole substituted tryptamines with R1 or R2 substitutions. In some cases, the process may be carried out in a whole-cell microbial fermentation. In some cases, an engineered microbial cell may be cultured in the presence of indole or a substituted indole (e.g., indole or substituted indole may be fed to or otherwise incubated with the microbial cell). In other cases, the indole or substituted indole may be produced biosynthetically by the microbial cell. For example, a microbial cell may produce indole or a substituted indole naturally. In other cases, the microbial cell may be engineered to produce indole or a substituted indole (e.g., by overexpressing enzymes for the production of substituted indoles).

Synthesis of a Substituted Tryptamine From Indole or a Substituted Indole in Engineered Microbial Cells Scheme 2 depicts a non-limiting example of synthesis of a substituted tryptamine from indole or a substituted indole in an engineered microbial cell.

Scheme 2

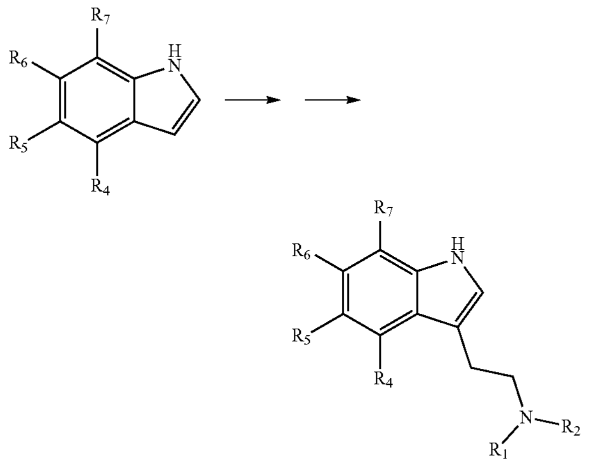

In some aspects, the disclosure provides a method for the production of substituted tryptamines by cultivating engineered microbes in the presence of indole or a substituted indole,

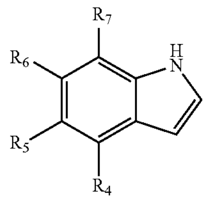

where —R is, but is not limited to, a halogen (—Br, —F, —Cl, —I, etc), —OH, C1-C5 alkyl, C1-C5 alkoxy, $NO_2$, NH, COOH, CN, sulfur, $SO_3$, $SO_4$, or $PO_4$. The resulting substituted tryptamine,

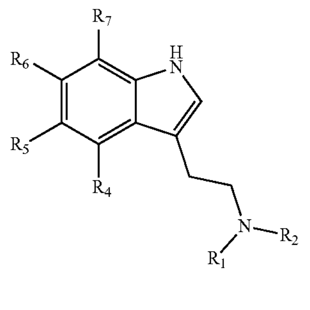

may be recovered from the culture broth. In some cases, the resulting tryptamine may be used in further downstream chemistry, taking advantage of chemical leaving groups or protecting groups incorporated into the tryptamine scaffold during the fermentative biosynthetic process.

Synthesis of a Substituted Tryptamine From Anthranilate or a Substituted Anthranilate in Engineered Microbial Cells Scheme 3

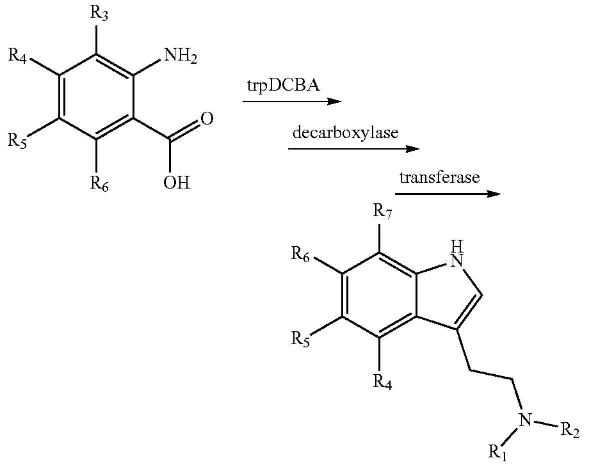

In some aspects, the processes described herein may involve the use of engineered microbes for the production of substituted tryptamines from anthranilate or substituted anthranilate. Scheme 3 depicts a non-limiting example of production of a substituted tryptamine from a substituted anthranilate in an engineered microbial cell. In some cases, the engineered microbial cell may be a bacterial cell. In some cases, the bacteria may be *Escherichia coli* or *Corynebacterium glutamicum*. In some cases, the bacteria may comprise modified host genetics, including knockout of tna (tryptophanase), trpR (tryptophan repressor element), and trpE (anthranilate synthase). In some cases, the engineered microbial cell may be a yeast cell. In some cases, the yeast cell may be of the species *Saccharomyces cerevisiae*. In some cases, the microbial cell may be further modified to express or overexpress one or more genes. In some cases, the microbial cell may be engineered to contain extra DNA copies by plasmid or genomic integration of an endogenous or heterologous trpDCBA operon. In some cases, the trpDCBA operon may comprise any one of SEQ ID NOs: 1-4. In some cases, the trpDCBA operon may comprise a nucleic acid sequence having at least 40%, at least 50%, at least 60%, at least 70%, at least 80%, at least 90%, or at least 95% sequence identity to any one of SEQ ID NOs: 1-4. In some cases, the engineered microbial cell may produce one or more enzymes having an amino acid sequence according to any one of SEQ ID NOs: 5-13, or an amino acid sequence having at least 40%, at least 50%, at least 60%, at least 70%, at least 80%, at least 90%, or at least 95% sequence identity to any one of SEQ ID NOs: 5-13. In some cases, the engineered microbial cell may produce one or more of trpD, trpB, trpC, or trpA, wherein the enzyme has been modified or mutated to exhibit higher levels of activity.

In some cases, the microbial cell may be further engineered to express or overexpress one or more additional genes. In some aspects, such microbial cell may further express a tryptamine decarboxylase (see Scheme 3, "decarboxylase"). In some cases, the tryptamine decarboxylase may be expressed by genomic integration of DNA or expression of a plasmid in the microbial cell. Tryptamine decarboxylases may be pyridoxal phosphate (PLP)-independent or may be PLP-dependent. In some cases, a tryptamine decarboxylase may comprise any one of the amino acid sequences according to SEQ ID NOs: 14-20 (see Table 2), or an amino acid sequence having at least 40%, at least 50%, at least 60%, at least 70%, at least 80%, at least 90%, or at least 95% sequence identity to an amino acid sequence of any one of SEQ ID NOs: 14-20. In some cases, an engineered microbial cell may express a tryptamine decarboxylase that has been modified or mutated to exhibit higher activity levels.

In some cases, the R1 and R2 amino positions of the tryptamine or substituted tryptamines derived from fermentation can be modified by a transferase to yield, by non-limiting example, N-methyl, N,N-dimethyl, N-acetyl, or N-hydroxycinnamoyl functional groups. Thus, in some cases, an engineered microbial cell may further express or overexpress a transferase (see Scheme 3). In some cases, a transferase may comprise any one of the amino acid sequences shown in SEQ ID NOs: 21-31 (see Table 2), or an amino acid sequence having at least 40%, at least 50%, at least 60%, at least 70%, at least 80%, at least 90%, or at least 95% sequence identity to an amino acid sequence of any one of SEQ ID NOs: 21-31. In some cases, an engineered microbial cell may express a transferase that has been modified or mutated to exhibit higher activity levels.

In some cases, an additional transferase can be expressed, such as, but not limited to, a phosphotransferase (kinase), acetyl transferase, glucosyl transferase, or sulfotransferase, to further modify hydroxyls on the indole ring of the tryptamine. For example, such as when engineered cells are cultivated in the presence of 6-hydroxyanthranilate or 4-hydroxy indole to yield 4-hydroxy-N,N-dimethyltryptamine, a kinase can be expressed yielding the phosphate ester of 4-hydroxy-N,N-dimethyltryptamine, psilocybin. Suitable kinases may include, but are not limited to, an amino acid sequence shown in any one of SEQ ID NOs: 41-44 (see Table 2), or an amino acid sequence having at least 40%, at least 50%, at least 60%, at least 70%, at least 80%, at least 90%, or at least 95% sequence identity to an amino acid sequence of any one of SEQ ID NOs: 41-44.

In some cases, the substituted anthranilate may be any one of 5-bromoanthranilate, 6-hydroxyanthranilate, 5-hydroxyanthranilate, 6-chloroanthranilate, and 5-chloroanthranilate. In some cases, the tryptamine may be any one of tryptamine, 5-hydroxytryptamine, 5-hydroxymethyltryptamine, 5-hydroxy-N,N-dimethyltryptamine, 5-phosphoryloxymethyltryptamine, 5-phosphoryloxy-N,N-dimethyltryptamine, 4-hydroxytryptamine, 4-hydroxy-N,N-dimethyltryptamine, 4-phosphoryloxytryptamine, 4-phosphoryloxy-N,N-tryptamine, 7-hydroxytryptamine, 7-phosphoryloxymethyltryptamine, 7-phosphoryloxy-N,N-dimethyltryptamine, 4-chloro-tryptamine, 4-chloro-N,N-dimethyltryptamine, 5-bromotryptamine, 5-bromo-methyltryptamine, 5-bromo-N-methyltryptamine, 5-bromo-N,N-dimethyltryptamine, N-acetyl-tryptamine, and 4-hydroxy-N-acetyl-tryptamine.

Synthesis of a Substituted Tryptamine From Indole or a Substituted Indole in Engineered Microbial Cells Scheme 4

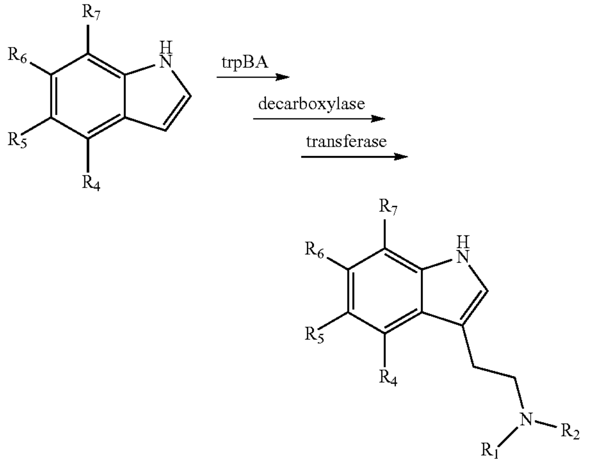

In some aspects, the processes described herein may involve the use of engineered microbes for the production of substituted tryptamines from indole or substituted indole. Scheme 4 depicts a non-limiting example of production of a substituted tryptamine from a substituted indole in an engineered microbial cell. In some cases, the engineered microbial may be a bacterial cell. In some cases, the bacterial cell may be of the species *Escherichia coli* or *Corynebacterium glutamicum*. In some cases, the bacterial cell may comprise modified host genetics, including knockout of tna (tryptophanase), trpR (tryptophan repressor element), and trpE (anthranilate synthase). In some cases, the microbial cell may be a yeast cell. In some cases, the yeast cell may be of the species *Saccharomyces cerevisiae*.

In some cases, the microbial cell may be further modified to express or overexpress one or more genes. In some cases, the microbial cell may be engineered to contain extra DNA copies by plasmid or genomic integration of endogenous or heterologous trpB and trpA (see, e.g., Scheme 4). In some cases, trpB and trpA may comprise amino acid sequences according to any one of SEQ ID NOs; 5-13 (see Table 2), or an amino acid sequence having at least 40%, at least 50%, at least 60%, at least 70%, at least 80%, at least 90%, or at least 95% sequence identity to any amino acid sequence shown in SEQ ID NOs: 5-13. In some cases, an engineered microbial cell may express trpB and/or trpA that has been modified or mutated to exhibit higher activity levels.

In some cases, the microbial cell may be further engineered to express or overexpress one or more additional genes. In some aspects, such microbial cell may further express a tryptamine decarboxylase (see, e.g., Scheme 4, "decarboxylase"). In some cases, the tryptamine decarboxylase may be expressed by genomic integration of DNA or expression of a plasmid in the microbial cell. Tryptamine decarboxylases may be pyridoxal phosphate (PLP)-independent or may be PLP-dependent. In some cases, a tryptamine decarboxylase may comprise any one of the amino acid sequences according to SEQ ID NOs: 14-20 (see Table 2), or an amino acid sequence having at least 40%, at least 50%, at least 60%, at least 70%, at least 80%, at least 90%, or at least 95% sequence identity to an amino acid sequence of any one of SEQ ID NOs: 14-20. In some cases, an engineered microbial cell may express a tryptamine decarboxylase that has been modified or mutated to exhibit higher activity levels.

In some cases, the R1 and R2 amino positions of the tryptamine or substituted tryptamines derived from fermentation can be modified by a transferase to yield, by non-limiting example, N-methyl, N,N-dimethyl, N-acetyl, or N-hydroxycinnamoyl functional groups. Thus, in some cases, an engineered microbial cell may further express or overexpress a transferase (see, e.g., Scheme 4). In some cases, a transferase may comprise any one of the amino acid sequences shown in SEQ ID NOs: 21-31 (see Table 2), or an amino acid sequence having at least 40%, at least 50%, at least 60%, at least 70%, at least 80%, at least 90%, or at least 95% sequence identity to an amino acid sequence of any one of SEQ ID NOs: 21-31. In some cases, an engineered microbial cell may express a transferase that has been modified or mutated to exhibit higher activity levels. In some cases, an additional transferase can be expressed, such as, but not limited to, a phosphotransferase (kinase), acetyl transferase, glucosyl transferase, or sulfotransferase, to further modify hydroxyls on the indole ring of the tryptamine. For example, such as when engineered cells are cultivated in the presence of 6-hydroxyanthranilate or 4-hydroxy indole to yield 4-hydroxy-N,N-dimethyltryptamine, a kinase can be expressed yielding the phosphate ester of 4-hydroxy-N,N-dimethyltryptamine, psilocybin. Suitable kinases may include, but are not limited to, an amino acid sequence shown in any one of SEQ ID NOs: 41-44 (see Table 2), or an amino acid sequence having at least 40%, at least 50%, at least 60%, at least 70%, at least 80%, at least 90%, or at least 95% sequence identity to an amino acid sequence of any one of SEQ ID NOs: 41-44.

In some cases, the substituted indole may be any one of 5-hydroxyindole, 4-hydroxyindole, 7-hydroxyindole, and 4-chloroindole, 5-bromoindole, and 4-fluoroindole. In some cases, the tryptamine may be any one of tryptamine, 5-hydroxytryptamine, 5-hydroxymethyltryptamine, 5-hydroxy-N,N-dimethyltryptamine, 5-phosphoryloxymethyltryptamine, 5-phosphoryloxy-N,N-dimethyltryptamine, 4-hydroxytryptamine, 4-hydroxy-N,N-dimethyltryptamine, 4-phosphoryloxytryptamine, 4-phosphoryloxy-N,N-tryptamine, 7-hydroxytryptamine, 7-phosphoryloxymethyltryptamine, 7-phosphoryloxy-N,N-dimethyltryptamine, 4-chloro-tryptamine, 4-chloro-N,N-dimethyltryptamine, 5-bromotryptamine, 5-bromo-methyltryptamine, 5-bromo-N-methyltryptamine, 5-bromo-N,N-dimethyltryptamine, N-acetyl-tryptamine, and 4-hydroxy-N-acetyl-tryptamine.

Synthesis of 4-hydroxyl Substituted and/or R1 or R2 Amine Substituted Tryptamines From Tryptophan by Engineered Microbial Cells Scheme 5

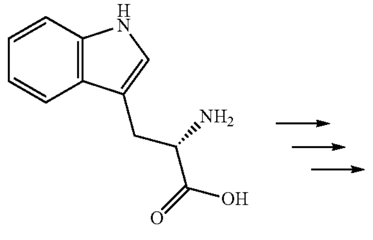

L-tryptophan

-continued

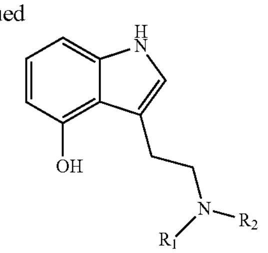

4-hydroxytryptamine

In another aspect, 4-hydroxyl substituted and/or R1 or R2 amine substituted tryptamines may be biosynthetically produced from tryptophan by engineered microbial cells, in accordance with Scheme 5.

In some cases, a microbial cell, may contain heterologous DNA on a plasmid or by integration into the genome that expresses enzymes that convert L-tryptophan to tryptamine (e.g., a decarboxylase) and/or that convert tryptamine to 4-hydroxytryptamine (e.g., a tryptophan 4-hydroxylase). Decarboxylases may be pyridoxal phosphate (PLP)-independent or PLP-dependent.

In some cases, the microbial cell may be engineered to express or overexpress a decarboxylase. In some cases, the decarboxylase may have an amino acid sequence of any one of SEQ ID NOs: 14-20 (see Table 2), or an amino acid sequence having at least 40%, at least 50%, at least 60%, at least 70%, at least 80%, at least 90%, or at least 95% sequence identity to an amino acid sequence of any one of SEQ ID NOs: 14-20. In some cases, an engineered microbial cell may express a decarboxylase that has been modified or mutated to exhibit higher activity levels.

In some cases, the microbial cell may be engineered to express or overexpress a tryptamine 4-hydroxylase. Tryptamine 4-hydroxylases are P450 enzymes that require a P450 reductase pair to provide reducing power via transfer of electrons from NADPH. In some cases, the tryptamine 4-hydroxylase may have an amino acid sequence according to any one of SEQ ID NOs: 32-35 (see Table 2), or an amino acid sequence having at least 40%, at least 50%, at least 60%, at least 70%, at least 80%, at least 90%, or at least 95% sequence identity to an amino acid sequence of any one of SEQ ID NOs: 32-35. In some cases, an engineered microbial cell may express a tryptamine 4-hydroxylase that has been modified or mutated to exhibit higher activity levels.

In some cases, the microbial cell may be engineered to express or overexpress a P450 reductase. In some cases, the P450 reductase may have an amino acid sequence according to any one of SEQ ID NOs: 36-40 (see Table 2), or an amino acid sequence having at least 40%, at least 50%, at least 60%, at least 70%, at least 80%, at least 90%, or at least 95% sequence identity to any one of SEQ ID NOs: 36-40. In some cases, an engineered microbial cell may express a P450 reductase that has been modified or mutated to exhibit higher activity levels.

In some cases, an additional transferase can be expressed, such as, but not limited to, a phosphotransferase (kinase), acetyl transferase, glucosyl transferase, or sulfotransferase to further modify hydroxyls on the indole ring of the tryptamine. When the production compound of interest is 4-hydroxy-N,N-dimethyltryptamine, a kinase can be expressed yielding the phosphate ester of 4-hydroxy-N,N-dimethyltryptamine, psilocybin. In some cases, the microbial cell may be further engineered to express or overexpress a kinase. In some cases, the kinase may have an amino acid sequence according to any one of SEQ ID NOs: 41-44 (see Table 2), or an amino acid sequence having at least 40%, at least 50%, at least 60%, at least 70%, at least 80%, at least 90%, or at least 95% sequence identity to any one of SEQ ID NOs: 41-44. In some cases, an engineered microbial cell may express a kinase that has been modified or mutated to exhibit higher activity levels.

Synthesis of Tryptamine Derivatives from Substitute Tryptamines in Engineered Microbial Cells In another aspect, derivatives of tryptamine may be biosynthetically produced from substituted tryptamines by engineered microbial cells.

In some cases, a microbial cell, may contain heterologous DNA on a plasmid or by integration into the genome that expresses enzymes that convert a substitute tryptamine to a tryptamine derivative. In some cases, the microbial cell may be engineered to express or overexpress a tryptamine 4-hydroxylase. In some cases, the tryptamine 4-hydroxylase may have an amino acid sequence of any one of SEQ ID NOs: 32-35 (see Table 2), or an amino acid sequence having at least 40%, at least 50%, at least 60%, at least 70%, at least 80%, at least 90%, or at least 95% sequence identity to an amino acid sequence of any one of SEQ ID NOs: 32-35. In some cases, an engineered microbial cell may express a tryptamine 4-hydroxylase that has been modified or mutated to exhibit higher activity levels. In some cases, the microbial cell may be engineered to express or overexpress a tryptamine 5-hydroxylase. In some cases, the tryptamine 5-hydroxylase may have an amino acid sequence according to SEQ ID NO: 47 (see Table 2), or an amino acid sequence having at least 40%, at least 50%, at least 60%, at least 70%, at least 80%, at least 90%, or at least 95% sequence identity to an amino acid sequence according to SEQ ID NO: 47. In some cases, an engineered microbial cell may express a tryptamine 5-hydroxylase that has been modified or mutated to exhibit higher activity levels. In some cases, the microbial cell may be engineered to express or overexpress a 4-hydroxytryptamine kinase. In some cases, the 4-hydroxytryptamine kinase may have an amino acid sequence according to any one of SEQ ID NOs: 41-44 (see Table 2), or an amino acid sequence having at least 40%, at least 50%, at least 60%, at least 70%, at least 80%, at least 90%, or at least 95% sequence identity to an amino acid sequence according to any one of SEQ ID NOs: 41-44. In some cases, an engineered microbial cell may express a 4-hydroxytryptamine kinase that has been modified or mutated to exhibit higher activity levels.

Figure 18A:
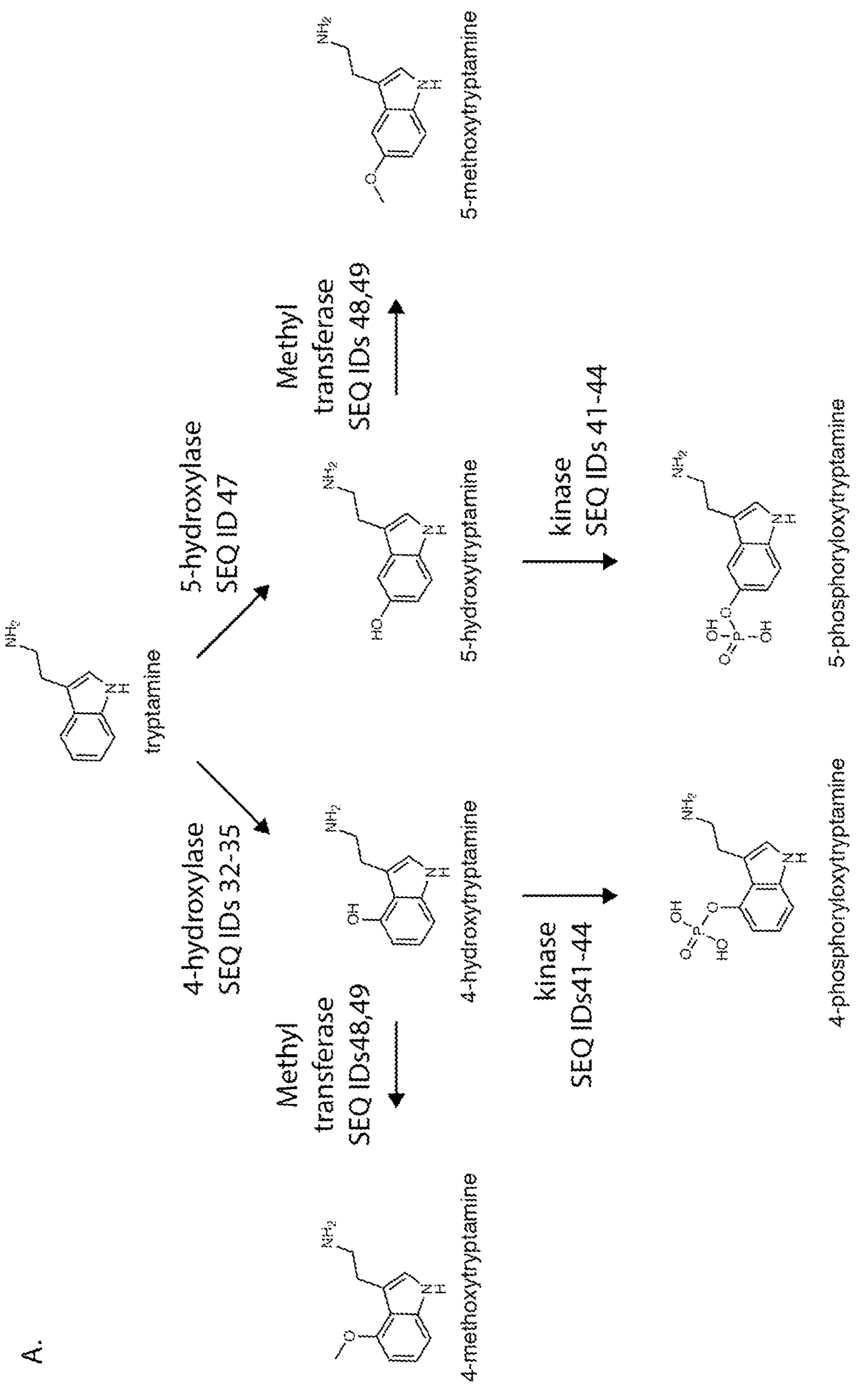
FIG. 18A depicts a non-limiting example of a biosynthetic pathway converting tryptamine to tryptamine derivatives.

FIG. 18A depicts a non-limiting example of a biosynthetic pathway for converting tryptamine to tryptamine derivatives. For example, tryptamine may be converted to 4-hydroxytryptamine by 4-hydroxylase (e.g., SEQ ID NOs:32-35). 4-hydroxytryptamine may be converted to 4-methoxytryptamine by a methyl transferase (e.g., SEQ ID NOs:48 or 49), or 4-phosphoryloxytryptamine by a kinase (e.g., SEQ ID NOs:41-44). In another example, tryptamine may be converted to 5-hydroxytryptamine by 5-hydroxylase (e.g., SEQ ID NO:47). 5-hydroxytryptamine may be converted to 5-methoxytryptamine by a methyl transferase (e.g., SEQ ID NOs:48 or 49), or to 5-phosphoryloxytryptamine by a kinase (e.g., SEQ ID NOs:41-44).

Figure 18B:
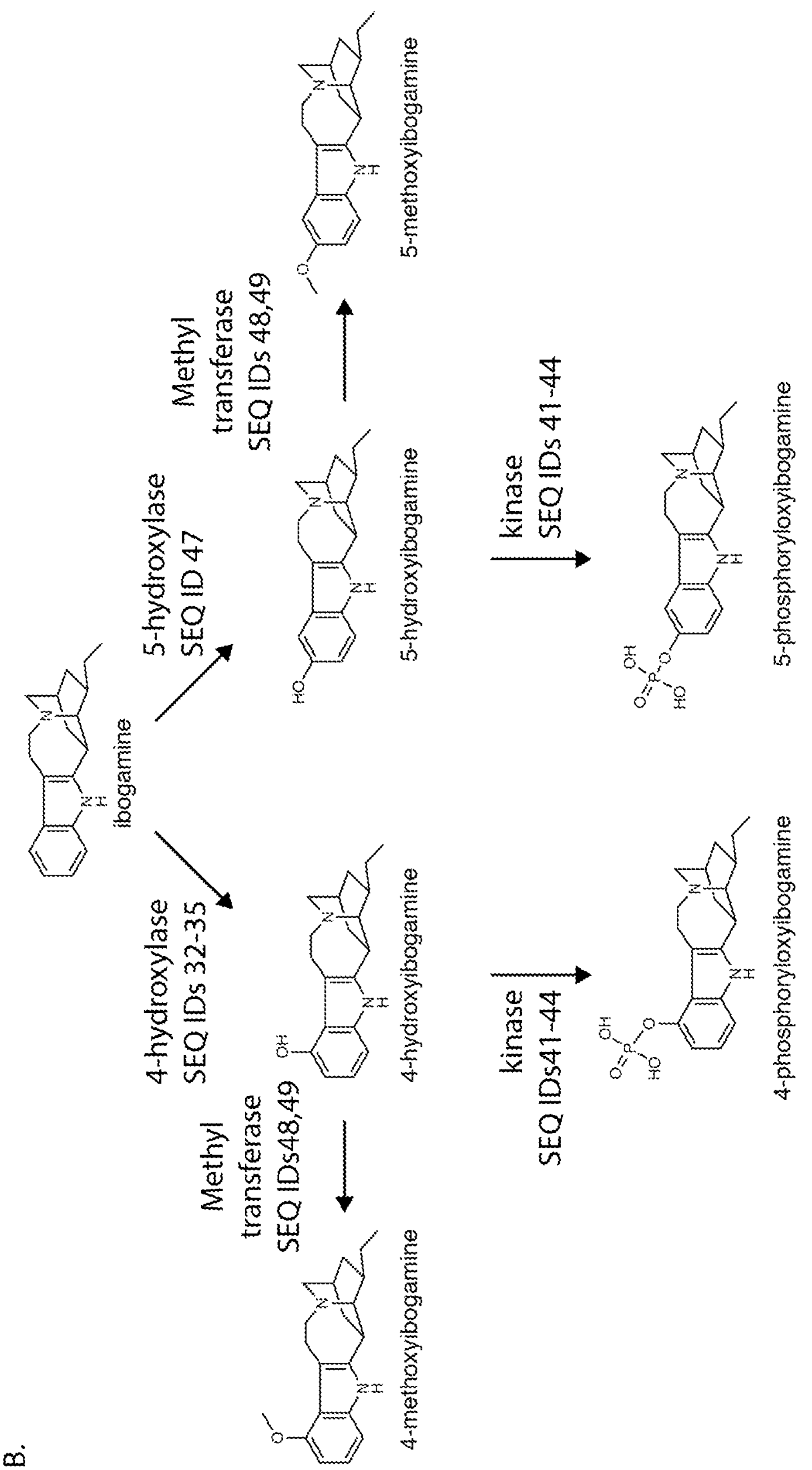
FIG. 18B depicts a non-limiting example of a biosynthetic pathway converting ibogamine to derivatives of ibogamine.

FIG. 18B depicts a non-limiting example of a biosynthetic pathway converting ibogamine to derivatives of ibogamine. For example, ibogamine may be converted to 4-hydroxyibogamine by 4-hydroxylase (e.g., SEQ ID NOs:32-35). 4-hydroxyibogamine may be converted to 4-methoxyibogamine by a methyl transferase (e.g., SEQ ID NOs:48 or 49), or to 4-phosphoryloxyibogamine by a kinase (e.g., SEQ ID NOs:41-44). In another example, ibogamine may be converted to 5-hydroxyibogamine by 5-hydroxylase (e.g., SEQ ID NO:47). 5-hydroxyibogamine may be converted to 5-methoxyibogamine by a methyl transferase (e.g., SEQ ID NO:48 or 49), or to 5-phosphoryloxyibogamine by a kinase (e.g., SEQ ID NOs:41-44).

In some cases, the engineered microbial cell may be cultured in the presence of one or more tryptamines. In some cases, the tryptamine is selected from the group consisting of: 5-methoxy-N,N-dimethyl-tryptamine, N,N-diisopropyl-tryptamine, N-methyl-N-isopropyltryptamine, N,N-dimethyltryptamine, N,N-tetramethylenetryptamine, N,N-dipropyltryptamine, ibogamine, and 12-methoxyibogamine, tryptamine, 4-hydroxytryptamine, 5-hydroxytryptamine, ibogamine, 4-hydroxyibogamine, and 5-hydroxyibogamine.

In some cases, the engineered microbial cell may convert a tryptamine to a tryptamine derivative. In some cases, the tryptamine derivative is any tryptamine derivative described in FIG. 16. In some cases, the tryptamine derivative is selected from the group consisting of: 5-hydroxy-N,N-diisopropyl-tryptamine, 5-hydroxy-N-methyl-N-isopropyl-tryptamine, 5-hydroxy-N,N-dimethyltryptamine, 5-hydroxy-N,N-tetramethylenetryptamine, 5-hydroxy-N,N-dipropyltryptamine, 4,5-methoxy-N,N-dimethyl-tryptamine, 4-hydroxy-N,N-diisopropyl-tryptamine, 4-hydroxy-N-methyl-N-isopropyltryptamine, 4-hydroxy-N,N-dimethyltryptamine, 4-hydroxy-N,N-tetramethylenetryptamine, 4-hydroxy-N,N-dipropyltryptamine, 4-phosphoryloxy-N,N-dipropyltryptamine, ibogamine, 12-methoxyibogamine, 4-hydroxytryptamine, 5-hydroxytryptamine, 4-methoxytryptamine, 5-methoxytryptamine, 4-phosphoryloxytryptamine, 5-phosphoryloxytryptamine, 4-hydroxyibogamine, 5-hydroxyibogamine, 4-phosphoryloxyibogamine, and 5-phosphoryloxyibogamine.

Assay for Detecting Levels of 4-hydroxytryptamine in a Host Cell

Scheme 6

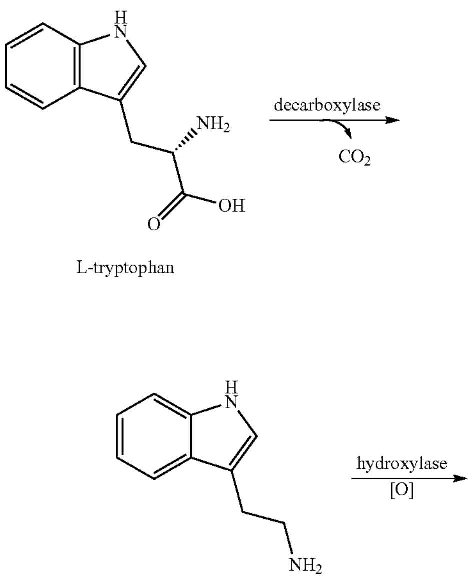

L-tryptophan tryptamine

-continued

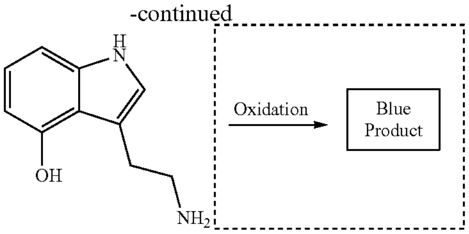

4-hydroxytryptamine

In another aspect, the disclosure provides a method for detecting levels of 4-hydroxytryptamine in a host cell. In some cases, the method comprises detecting, in a host cell genetically modified to produce a 4-hydroxytryptamine, a colored or fluorescent product of 4-hydroxytryptamine. In some cases, the colored or fluorescent product of 4-hydroxytryptamine may be produced by the action of an oxidizing mechanism produced in the cell. In some cases, the level of 4-hydroxytryptamine produced in the cell may be directly proportional to the level of 4-hydroxytryptamine or a colored product of 4-hydroxytryptamine produced in the cell (see, e.g., Scheme 6). Such in vivo screening methods may be used to rapidly screen for tryptamine 4-hydroxylase mutants having high activity in the engineered production host cell (DeLoache et al. 2015).

The oxidizing mechanism can be catalyzed by iron sulphate or by an enzyme expressed by a host cell, including, but not limited to, the enzyme multicopper oxidase (Blaschko and Levine 1960). A non-limiting example of a suitable oxidase is shown in SEQ ID NO: 45 (see Table 2). In some cases, a genetically modified cell comprising a nucleic acid sequence encoding a variant tryptophan 4-hydroxylase may produce a level of 4-hydroxytryptamine, or a colored or fluorescent product thereof, that is higher than a level of 4-hydroxytryptamine, or a colored or fluorescent product thereof, in a control cell not comprising a nucleic acid sequence encoding the variant tryptamine 4-hydroxylase. This may indicate that the variant enzyme increases flux through the biosynthetic pathway, thereby creating higher titers and rates of 4-hydroxytryptamine production. The genetically modified host cell containing higher 4-hydroxytryptamine production can contain enzymes, such as methyl-, sulphono-, glucosyl- and/or phospho transferases for the 4-hydroxyindole position or amino position, as described herein.

In some cases, the modified host cell may be modified to increase flux through tryptophan and to increase tryptophan production. This can be achieved by knockout of aro8 and aro10 and overexpression of TRP1, TRP2, TRP3, TRP4 and TRP5. Additionally, inclusion of TRP2 feedback resistant mutant allele can be employed.

In a non-limiting example (see Example 1), 1-tryptophan may be converted, in a modified microbial host cell expressing a decarboxylase, hydroxylase, P450 reductase, methyltransferase and kinase, to O-phosphoryl-4-hydroxy-N,N-dimethyltryptamine.

Culture Conditions and Product Production

In some cases, the genetically modified host cell may be cultured under aerobic conditions. In some cases, the genetically modified host cell may be cultured under anaerobic conditions.

In some cases, the culture media may be a minimal media, including, but not limited to, M9, MOPS, YNB, ammonia salts, or a complex media containing, for example, yeast extract, casamino acids, peptone, or tryptone. In some cases, the culture media may be buffered, for example, by phosphate salts, HEPES, or Tris. In some cases, the culture media may contain a reducing agent, for example, L-ascorbic acid, dithiothreitol, or mercaptoethanol. In some cases, the culture media may be supplemented with additional amino acids, such as L-methionine, Histidine, Arginine, Alanine, Isoleucine, Cysteine, Aspartic acid, Leucine, Glutamine, Asparagine, Lysine, Glycine, Glutamic acid, Proline, Serine, Phenylalanine, Tyrosine, Selenocysteine, Threonine, Pyrrolysine, Tryptophan, or Valine. In some cases, additional vitamins and cofactors may be added, for example, L-ascorbic acid, thiamine, pyridoxal phosphate, niacin, pyridoxine, biotin, folic acid, tetrahydrofolic acid, riboflavin, pantothenic acid, copper salts, magnesium salts, manganese salts, molybdenum salts, iron salts, zinc salts, nickel salts, glutathione, heme, or D-aminolevulinic acid.

In some cases, the genetically modified host cell may be fed a substituted anthranilate by single addition, batch feeding, or constant dilution in culture. In some cases, the genetically modified host cell may be fed a substituted indole by single addition, batch feeding, or constant dilution in culture.

In some cases, a downstream product may be produced. In some cases, the downstream product may be purified, e.g., isolated and purified from the culture medium, from a cell lysate, or both. In some cases, the downstream product may be at least, or about, 25%, 30%, 40%, 50%, 60%, 70%, 75%, 80%, 90%, 95%, or 99%, by weight, pure. Purification can be carried out by any known method or combination of methods, which methods include, e.g., column chromatography, phase separation, precipitation, crystallization, decantation, gas stripping, membrane enhanced separation, fractionation, adsorption/desorption, pervaporation, thermal or vacuum desorption from a solid phase, extraction of the product that is immobilized or absorbed to a solid phase with a solvent, etc. Purity can be assessed by any appropriate method, e.g., by column chromatography, high performance liquid chromatography (HPLC) analysis, or gas chromatography-mass spectrometry (GC-MS) analysis.

In some cases, the cells in culture may convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the fed precursor in the cell culture medium into the desired product. In some cases, the cells in culture may produce at least 2 g/L, at least 3 g/L, at least 4 g/L, at least 5 g/L, at least 7 g/L, at least 10 g/L, or more than 50 g/L of the desired product in liquid culture medium.

In some cases, the cells in culture may convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into the desired product. In some cases, the cells in culture may produce at least 2 g/L, at least 3 g/L, at least 4 g/L, at least 5 g/L, at least 7 g/L, at least 10 g/L, or more than 50 g/L of the desired product in liquid culture medium.

Host Cells

Suitable host cells include cells that can be cultured in media, e.g., as unicellular organisms. Suitable host cells include yeast cells, fungal cells, insect cells, mammalian cells, algal cells, and bacterial cells. Suitable host cells may further include filamentous fungal cells; suitable filamentous fungal cells include, e.g., *Aspergillus, Neurospora*, and the like.

The host cell can be a prokaryotic cell. Suitable prokaryotic cells include, but are not limited to, any of a variety of laboratory strains of *Escherichia coli, Corynebacterium glutamicum, Lactobacillus* sp., *Salmonella* sp., *Shigella* sp., *Citrobacter, Enterobacter, Clostridium, Klebsiella, Aerobacter*, and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some cases, the host cell is *Escherichia coli.*

Non-limiting examples of suitable yeast host cells are strains selected from a cell of a species of *Candida, Kluyveromyces, Saccharomyces, Schizosaccharomyces, Pichia, Hansenula*, and *Yarrowia*. In some cases, the yeast host cell may be selected from the group consisting of: *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Saccharomyces uvarum, Pichia kluyveri, Yarrowia hpolytica, Candida utilis, Candida cacaoi*, and *Geotrichum fermentans*. Other useful yeast host cells are *Kluyveromyces lactis, Kluyveromyces fragilis, Hansenula polymorpha, Pichia pastoris, Yarrowia lipolytica, Schizosaccharomyces pombe, Ustilgo maylis, Candida maltose, Pichia guillermondii* and *Pichia methanoliol*. Suitable yeast host cells may include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pljperi, Pichia stiptis, Pichia methanolica, Pichia* sp., *Saccharomyces cerevisiae, Saccharomyces* sp., *Hansenula polymorpha*, and the like. In some cases, a yeast host cell may be *Saccharomyces cerevisiae*; e.g., a genetically modified cell of the present disclosure may be a genetically modified *Saccharomyces cerevisiae* cell.

The filamentous fungi may be characterized by a mycelial wall composed of chitin, cellulose, glucan, chitosan, mannan, and other complex polysaccharides. Vegetative growth may be by hyphal elongation and carbon catabolism may be obligately aerobic. Suitable filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Phanerochaete, Pleurotus, Schizophyllum, Talaromyces, Thermoascus, Thielavia, Tolypocladium*, and *Trichoderma*. Non-limiting examples of suitable filamentous fungal cells include, e.g., *Aspergillus niger, Aspergillus awamori, Aspergillus foetidus, Aspergillus sojae, Aspergillus fumigatus*, and *Aspergillus oryzae*. Another example of a suitable fungal cell is a *Neurospora crassa* cell.

Heterologous Protein Expression in Modified Host Cells

In some cases, a nucleotide sequence encoding a heterologous polypeptide may be operably linked to a transcriptional control element.

Suitable promoters for expression in bacteria may include, but are not limited to, pT7, ptac, pLac, pLacUV5, pTet, pBAD, and the constitutive BBa series of promoters of the Anderson promoter library (Kelly et al, "Measuring the activity of BioBrick promoters using an in vivo reference standard" Journal of Biological Engineering 2009 3:4). Suitable promoters for expression in yeast may include, but are not limited to, TDH3, CCW12, CYC1, HIS3, GAL1, GAL10, ADH1, PGK, PHO5, GAPDH, ADC1, TRP1, URA3, LEU2, ENO, and TP1; and, AOX1 (e.g., for use in *Pichia*).

The expression vector may also contain a ribosome binding site for translation initiation and a transcription terminator. The expression vector may also include appropriate sequences for amplifying expression.

In some cases, the expression of the amino acid sequence may be codon optimized or biased to increase expression of protein in vivo. This may be achieved by several algorithms (Hanson and Coller, Nature Reviews Molecular Cell Biology volume 19, pages 20-30 (2018)), (Quax, et al Molecular Cell Review volume 59, Jul. 16, 2015). In some cases, the native amino acid sequence may be used for coding an amino acid sequence in vivo.

In some cases, a genetically modified microbial cell of the disclosure may comprise one or more nucleic acid sequences according to any one of SEQ ID NOs: 1-4 (see Table 1), or a nucleic acid sequence having at least 40%, at least 50%, at least 60%, at least 70%, at least 80%, at least 90%, or at least 95% sequence identity to any one of SEQ ID NOs: 1-4.

In some cases, a genetically modified microbial cell of the disclosure may express or overexpress one or more enzymes having an amino acid sequence according to any one of SEQ ID NOs: 5-49, or an amino acid sequence having at least 40%, at least 50%, at least 60%, at least 70%, at least 80%, at least 90%, or at least 95% sequence identity to any one of SEQ ID NOs: 5-49.

TABLE 1

DNA Sequences

| Operonic sequences | Host/ Sequence origin | Sequence |
|---|---|---|
| trpDCBA | Prokaryotic/ *E. coli* | atggctgacattctgctgctcgataatatcgactcttttacgtacaacctggcagatcagttgcg<br>cagcaatgggcataacgtggtgatttaccgcaaccatattccggcgcaaaccttaattgaacgcc<br>tggcgaccatgagcaatccggtgctgatgctttctcctggccccggtgtgccgagcgaagccggt<br>tgtatgccggaactcctcacccgcttgcgtggcaagctgcccattattggcatttgcctcggaca<br>tcaggcgattgtcgaagcttacgggggctatgtcggtcaggcgggcgaaattctccacggtaaag<br>cctccagcattgaacatgacggtcaggcgatgtttgccggattaacaaacccgctgccggtggcg<br>cgttatcactcgctggttggcagtaacattccggccggtttaaccatcaacgcccattttaatgg<br>catggtgatggcagtacgtcacgatgcggatcgcgtttgtggattccagttccatccggaatcca<br>ttctcaccacccagggcgctcgcctgctggaacaaacgctggcctgggcgcagcagaaactagag |

TABLE 1-continued

DNA Sequences

| Operonic sequences | Host/ Sequence origin | Sequence |
|---|---|---|
| | | ccagccaacacgctgcaaccgattctggaaaaactgtatcaggcgcagacgcttagccaacaag |
| | | aaagccaccagctgttttcagcggtggtgcgtggcgagctgaagccggaacaactggcggcg |
| | | gcgctggtgagcatgaaaattcgcggtgagcacccgaacgagatcgccggggcagcaaccgc |
| | | gctactggaaaacgcagcgccgttcccgcgcccggattatctgtttgctgatatcgtcggtactg |
| | | gcggtgacggcagcaacagtatcaatatttctaccgccagtgcgtttgtcgccgcggcctgtggg |
| | | ctgaaagtggcgaaacacggcaaccgtagcgtctccagtaaatctggttcgtccgatctgctggc |
| | | ggcgttcggtattaatcttgatatgaacgccgataaatcgcgccaggcgctggatgagttaggtg |
| | | tatgtttcctctttgcgccgaagtatcacaccggattccgccacgcgatgccggttcgccagcaa |
| | | ctgaaaacccgcaccctgttcaatgtgctggggccattgattaacccggcgcatccgccgctggc |
| | | gttaattggtgtttatagtccggaactggtgctgccgattgccgaaaccttgcgcgtgctggggt |
| | | atcaacgcgcggcggtggtgcacagcggcgggatggatgaagtttcattacacgcgccgacaatc |
| | | gttgccgaactgcatgacggcgaaattaaaagctatcagctcaccgcagaagactttggcctgac |
| | | accctaccaccaggagcaactggcaggcggaacaccggaagaaaaccgtgacattttaacacgt |
| | | ttgttacaaggtaaaggcgacgccgcccatgaagcagccgtcgctgcgaacgtcgccatgttaa |
| | | tgcgcctgcatggccatgaagatctgcaagccaatgcgcaaaccgttcttgaggtactgcgcagt |
| | | ggttccgcttacgacagagtcaccgcactggcggcacgagggtaaatgatgcaaaccgttttag |
| | | cgaaaatcgtcgcagacaaggcgatttgggtagaagcccgcaaacagcagcaaccgctggcc |
| | | agttttcagaatgaggttcagccgagcacgcgacatttttatgatgcgctacagggtgcgcgcac |
| | | ggcgtttattctggagtgcaagaaagcgtcgccgtcaaaaggcgtgatccgtgatgatttcgatc |
| | | cagcacgcattgccgccatttataaacattacgcttcggcaatttcggtgctgactgatgagaaa |
| | | tattttcaggggagctttaatttcctccccatcgtcagccaaatcgccccgcagccgattttatg |
| | | taaagacttcattatcgacccttaccagatctatctggcgcgctattaccaggccgatgcctgct |
| | | tattaatgctttcagtactggatgacgaccaatatcgccagcttgccgccgtcgctcacagtctg |
| | | gagatgggggtgctgaccgaagtcagtaatgaagaggaacaggagcgcgccattgcattgggagc |
| | | aaaggtcgttggcatcaacaaccgcgatctgcgtgatttgtcgattgatctcaaccgtacccgcg |
| | | agcttgcgccgaaactggggcacaacgtgacggtaatcagcgaatccggcatcaatacttacgct |
| | | caggtgcgcgagttaagccacttcgctaacggttttctgattggttcggcgttgatggcccatga |
| | | cgatttgcacgccgccgtgcgccgggtgttgctgggtgagaataaagtatgtggcctgacgcgtg |
| | | ggcaagatgctaaagcagcttatgacgcgggcgcgatttacggtgggttgatttttgttgcgaca |
| | | tcaccgcgttgcgtcaacgttgaacaggcgcaggaagtgatggctgcggcaccgttgcagtatgt |
| | | tggcgtgttccgcaatcacgatattgccgatgtggtggacaaagctaaggtgttatcgctggcgg |
| | | cagtgcaactgcatggtaatgaagaacagctgtatatcgatacgctgcgtgaagctctgccagca |
| | | catgttgccatctggaaagcattaagcgtcggtgaaaccctgcccgcccgcgagtttcagcacgt |
| | | tgataaatatgttttagacaacggccagggtggaagcgggcaacgttttgactggtcactattaa |
| | | atggtcaatcgcttggcaacgttctgctggcgggggcttaggcgcagataactgcgtggaagcg |
| | | gcacaaaccggctgcgccggacttgattttaattctgctgtagagtcgcaaccgggcatcaaaga |
| | | cgcacgtcttttggcctcggttttccagacgctgcgcgcatattaaggaaaggaacaatgacaac |
| | | attacttaacccctatttggtgagtttggcggcatgtacgtgccacaaatcctgatgcctgctc |
| | | tgcgccagctggaagaagcttttgtcagtgcgcaaaaagatcctgaatttcaggctcagttcaac |
| | | gacctgctgaaaaactatgccgggcgtccaaccgcgctgaccaaatgccagaacattacagccgg |
| | | gacgaacaccacgctgtatctcaagcgtgaagatttgctgcacggcggcgcgcataaaactaacc |
| | | aggtgctggggcaggcgttgctggcgaagcggatgggtaaaaccgaaatcatcgccgaaaccggt |
| | | gccggtcagcatggcgtggcgtcggcccttgccagcgccctgctcggcctgaaatgccgtattta |
| | | tatgggtgccaaagacgttgaacgccagtcgcctaacgtttttcgtatgcgcttaatgggtgcgg |
| | | aagtgatcccggtgcatagcggttccgcgacgctgaaagatgcctgtaacgaggcgctgcgcgac |
| | | tggtccggtagttacgaaaccgcgcactatatgctgggcaccgcagctggcccgcatccttatcc |
| | | gaccattgtgcgtgagtttcagcggatgattggcgaagaaaccaaagcgcagattctggaaagag |
| | | aaggtcgcctgccggatgccgttatcgcctgtgttggcggcggttcgaatgccatcggcatgttt |
| | | gctgatttcatcaatgaaaccaacgtcggcctgattggtgtggagccaggtggtcacggtatcga |
| | | aactggcgagcacggcgcaccgctaaaacatggtcgcgtgggtatctatttcggtatgaaagcgc |
| | | cgatgatgcaaaccgaagacgggcagattgaagaatcttactccatctccgccggactggatttc |
| | | ccgtctgtcggcccacaacacgcgtatcttaacagcactggacgcgctgattacgtgtctattac |
| | | cgatgatgaagcccttgaagccttcaaaacgctgtgcctgcacgaagggatcatcccggcgctgg |
| | | aatcctcccacgccctggcccatgcgttgaaaatgatgcgcgaaaacccggataaagagcagcta |
| | | ctggtggttaacctttccggtcgcggcgataaagacatcttcaccgttcacgatattttgaaagc |
| | | acgaggggaaatctgatggaacgctacgaatctctgtttgcccagttgaaggagcgcaaagaagg |
| | | cgcattcgttcctttcgtcacgctcggtgatccgggcattgagcagtcattgaaaattatcgata |
| | | cgctaattgaagccggtgctgacgcgctggagttaggtatccccttctccgacccactggcggat |
| | | ggcccgacgattcaaaacgccactctgcgcgcctttgcggcaggtgtgactccggcacaatgttt |
| | | tgaaatgctggcactgattcgccagaaacacccgaccattcccattggcctgttgatgtatgcca |
| | | atctggtgtttaacaaaggcattgatgagttttatgcccagtgcgaaaaagtcggcgtcgattcg |
| | | gtgctggttgccgatgtgccagttgaagagtccgcgcccttccgccaggccgcgttgcgtcataa |
| | | tgtcgcacctatcttcatctgcccgccaaatgccgatgacgacctgctgcgccagatagcctctt |
| | | acggtcgtggttacacctatttgctgtcacgagcaggcgtgaccggcgcagaaaaccgcgccgcg |
| | | ttacccctcaatcatctggttgcgaagctgaaagagtacaacgctgcacctccattgcagggatt |
| | | tggtatttccgccccggatcaggtaaaagcagcgattgatgcaggagctgcgggcgcgatttctg |
| | | gttcggccattgttaaaatcatcgagcaacatattaatgagccagagaaaatgctggcggcactg |
| | | aaagtttttgtacaaccgatgaaagcggcgacgcgcagttaa (SEQ ID NO: 1) |
| trpDCBA | Prokary- | atgaacagatttctacaattgtgcgttgacggaaaaacccttactgccggtgaggctgaaacgct |
| | otic/ | gatgaatatgatgatggcagcggaaatgactccttctgaaatgggggggatattgtcaattcttg |
| | *B.* | actctcgggggagacgccagaagagcttgcgggttttgtgaaggcaatgcgggcacacgctctt |
| | *subtilis* | acagtcgatggacttcctgatattgttgatacatgcggaacagggggagacggtatttccacttt |

TABLE 1-continued

| DNA Sequences | | |
|---|---|---|
| Operonic sequences | Host/ Sequence origin | Sequence |
| | | taatatctcaacggcctcggcaattgttgcctcggcagctggtgcgaaaatcgctaagcatggca<br>atcgctctgtctcttctaaaagcggaagcgctgatgttttagaggagctagaggtttctattcaa<br>accactcccgaaaaggtcaaaagcagcattgaaacaaacaacatgggatttctttttgcgccgct<br>ttaccattcgtctatgaaacatgtagcaggtactagaaaagagctaggtttcagaacggtattta<br>atctgcttgggccgctcagcaatcctttacaggcgaagcgtcaggtgattggggtctattctgtt<br>gaaaaagctggactgatggcaagcgcactggagacgtttcagccgaagcacgttatgtttgtatc<br>aagccgtgacggtttagatgagctttcaattacagcaccgaccgacgtgattgaattaaaggacg<br>gagagcgccgggagtataccgtttcacccgaagatttcggtttcacaaatggcagacttgaagat<br>ttacaggtgcagtctccgaaagagagcgcttatctcattcagaatattttgaaaataaaagcag<br>cagttccgctttatctattacggcttttaatgcgggtgctgcgatttacacggcgggaattaccg<br>cctcactgaaggaaggaacggagctggcgttagagacgattacaagcggaggcgctgccgcgcag<br>cttgaacgactaaagcagaaagaggaagagatctatgcttgaaaaaatcatcaaacaaaagaaag<br>aagaagtgaaaacactggttctgccggtagagcagcctttcgagaaacgttcatttaaggaggcg<br>ctggcaagcccgaatcggtttatcgggttgattgccgaagtgaagaaagcatcgccgtcaaaagg<br>gcttattaaagaggattttgtacctgtgcagattgcaaaagactatgaggctgcgaaggcagatg<br>cgatttccgttttaacagacaccccgtttttcaaggggaaaacagctatttatcagacgtaaag<br>cgtgctgtttcgattcctgtacttagaaaagattttattgattctcttcaagtagaggaatcaag<br>aagaatcggagcggatgccatattgttaatcggcgaggtgcttgatcccttacaccttcatgaat<br>tatatcttgaagcaggtgaaaaggggatggacgtgttagtggaggttcatgatgcatcaacgcta<br>gaacaaatattgaaagtgttcacacccgacattctcggcgtaaataatcgaaacctaaaaacgtt<br>tgaaacatctgtaaagcagacagaacaaatcgcatctctcgttccgaaagaatccttgcttgtca<br>gcgaaagcggaatcggttctttagaacatttaacatttgtcaatgaacatggggcgcgagctgta<br>cttatcggtgaatcattgatgagacaaacttctcagcgtaaagcaatccatgctttgtttaggga<br>gtgaggttgtgaagaaaccggcattaaaatattgcggtattcggtcactaaaggatttgcagctt<br>gcggcggaatcacaggctgattacctaggatttatttttgctgaaagcaaacgaaaagtatctcc<br>ggaagatgtgaaaaaatggctgaaccaagttcgtgtcgaaaaacaggttgcaggtgtttttgtta<br>atgaatcaatagagacgatgtcacgtattgccaagagcttgaagctcgacgtcattcagcttcac<br>ggtgatgaaaaaccggcggatgctgctgctcttcgcaagctgacaggctgtgaaatatggaaggc<br>gcttcaccatcaagataacacaactcaagaaatagcccgctttaaagataatgttgacggctttg<br>tgattgattcatctgtaaaagggtctagaggcggaactggtgttgcattttcttgggaatgtgtg<br>ccggaatatcagcaggcggctattggtaaacgctgctttatcgctggcggcgtgaatccggatag<br>catcacacgcctattgaaatggcagccagaaggaattgaccttgccagcggaattgaaaaaaacg<br>gacaaaaagatcagaatctgatgaggcttttagaagaaaggatgaaccgatatgtatccatatcc<br>gaatgaaataggcagatacggtgattttggcggaaagtttgttccggaaacactcatgcagccgt<br>tagatgaaatacaaacagcatttaaacaaatcaaggatgatcccgcttttcgtgaagagtattat<br>aagctgttaaaggactattccggacgcccgactgcattaacatacgctgatcgagtcactgaata<br>cttaggcggcgcgaaaatctatttgaaacgagaagatttaaaccatacaggttctcataaaatca<br>ataatgcgctaggtcaagcgctgcttgctaaaaaaatgggcaaaacgaaaatcattgctgaaacc<br>ggtgccggccagcatggtgttgccgctgcaacagttgcagccaaattcggcttttcctgtactgt<br>gtttatgggtgaagaggatgttgcccgccagtctctgaacgttttccgcatgaagcttcttggag<br>cggaggtagtgcctgtaacaagcggaaacggaacattgaaggatgccacaaatgaggcgatccgg<br>tactgggttcagcattgtgaggatcacttttatatgattggatcagttgtcggcccgcatcctta<br>tccgcaagtggtccgtgaatttcaaaaaatgatcggagaggaagcgaaggatcagttgaaacgta<br>ttgaaggcactatgcctgataaagtagtggcatgtgtaggcggaggaagcaatgcgatgggtatg<br>tttcaggcatttttaaatgaagatgttgaactgatcggcgctgaagcagcaggaaaaggaattga<br>tacacctcttcatgccgccactatttcgaaaggaaccgtaggggttattcacggttcattgactt<br>atctcattcaggatgagttcgggcaaattattgagccctactctatttcagccggtctcgactat<br>cctggaatcggtccggagcatgcatatttgcataaaagcggccgtgtcacttatgacagtataac<br>cgatgaagaagcggtggatgcattaaagcttttgtcagaaaaagaggggattttgccggcaatcg<br>aatctgcccatgcgttagcgaaagcattcaaactcgccaaaggaatggatcgcggtcaactcatt<br>ctcgtctgtttatcaggccggggagacaaggatgtcaacacattaatgaatgtattggaagaaga<br>ggtgaaagcccatgtttaaattggatcttcaaccatcagaaaaattgtttatcccgtttattacg<br>gcgggcgatccagttcctgaggtttcgattgaactggcgaagtcactccaaaaagcaggcgccac<br>agcattggagcttggtgttgcatactctgacccgcttgcagacggtccggtgatccagcgggctt<br>caaagcgggcgcttgatcaaggaatgaatatcgtaaaggcaatcgaattaggcggagaaatgaaa<br>aaaaacggagtgaatattccgattatcctctttacgtattataatcctgtgttacaattgaacaa<br>agaatacttttcgctttactgcgggaaaatcatattgacggtctgcttgttccggatctgccat<br>tagaagaaagcaacagccttcaagaggaatgtaaaagccatgaggtgacgtatatttctttagtt<br>gcgccgacaagcgaaagccgtttgaaaaccattattgaacaagccgaggggttcgtctactgtgt<br>atcttctctgggtgtgaccggtgtccgcaatgagttcaattcatccgtgtacccgttcattcgta<br>ctgtgaagaatctcagcactgttccggttgctgtagggttcggtatatcaaaccgtgaacaggtc<br>ataaagatgaatgaaattagtgacggtgtcgtagtgggaagtgcgctcgtcagaaaaatagaaga<br>attaaaggaccggctcatcagcgctgaaacgagaaatcaggcgctgcaggagtttgaggattatg<br>caatggcgtttagcggcttgtacagtttaaaatga (SEQ ID NO: 2) |
| trpDCBA | Prokaryotic/ *L. lactis* | atgaaaacaaggagtcatcaaatgaaaaatgaacttgaaaaagtgatgtcaggtcgtgacatgac<br>cgaaaatgaaatgaatatgcttgctaattcaattatccaaggtgaattaagcgaggtccaaattg<br>ccagctttttagtagcattaaaaatgaaaggtgaagcagcaagcgaattgactggtttggctcga<br>gctttacaaaaagcagcgattcccattccaacaaatttgacaaatgcgatggacaattgtggaac<br>aggaggcgaccgctcattcagttttaatatttcaaccacagccgcttttgttttagcagctggtg<br>gagtcaatatggcaaaacacggaaatcgctccattaccagtaaatctggctcggcagacgttctt<br>gaggccttaggaatcaatctttatttaccagcagaaaagttagctcaagtttttgacaaagttgg<br>tttagttttcctttttgctcaaaatctccacccagcgatgaaatacttcacgccagtccgcagac |

TABLE 1-continued

DNA Sequences

| Oper-onic se-quences | Host/ Sequence origin | Sequence |
|---|---|---|
| | | aactcgaaattccaacaattatgaacttgactgggccactaatcaatccaattccacttgatacg |
| | | caacttcttggtacctcacgtccagatttacttgaattaacagcaaatgttttgaaaggcttggg |
| | | ccgtaagcgagcattagtcatcacaggtgaaggcggaatggacgaagcaactccctttggactta |
| | | atcattacgcacttttagaaaatgacaaagtgactttgcatgaatttagagcctcagaagttggt |
| | | atttcagaagttcaactcaatgatattcgtggaggtgaagccccagaaaatgctgaaattttaaa |
| | | aaatgtccttgaaaatcaaccgtcagcctttttagaaacgaccgttttaaatgccggacttggat |
| | | tttatgccaatggaaaagttgattccatcaaatccggagttgaccttgcaagagaagtaattagt |
| | | acaggagcagctcttaccaagttgcatgaattacaagcagaacaaattggttaaaaatcttgatg |
| | | gcaaattttgaaatagcagaaaatgagagaaaaatatgaacataaaaaaaggaaaatttctagaa |
| | | acaatcctagcagaaaaacgacttgaaattgctaaaatgccagaagaacaagtaggaaaagttcg |
| | | tcaaacatacaattttttatgattacttaaaagaacattccgaccagcttcaagtgattgccgaag |
| | | tcaaaaaagcttcgcccagtctaggtgatattaacttagaagtggatatcgttgaccaagccaaa |
| | | aattacgaacaagccggtgccgctatgatttccgtcttaactgaccctgtatttttttaaaggaaa |
| | | tattgaatatctctgtgaaatttcagaaaatgtccaaatccccaccttgaacaaggattttatca |
| | | tcgataaaaaacaaatcaatcgggcagttaatgcgggagcaacagttattttactcattgtcgca |
| | | gtttttgaaaatcaataccccaaactccaaaacctctacaactacgcactttcactaggacttga |
| | | agttcttgttgaaacacataataaagcagaacttgagattgctcatcagcttggagctaaaatta |
| | | ttggagttaataatcgtaatttaaaaacctttgaagtgatcttacaaaattcagtagatttgaca |
| | | ccctactttaaagaagacagtatctacatttccgaatcaggcatttttagcgcaaacgaagccca |
| | | aaaagtttccgatactttcaatggaatattggttggaacagcactcatgcaatcagaaaatctag |
| | | aaaaatctttgaaagatttaaaagtcaagaggaaaacgaatgaaaattaaaatctgtggcttatc |
| | | tacaaaagaagctgttgatacagctgtagaatctggtgtcacacatctcggttttattcttagtc |
| | | cctcaaaacgccaagttgcaccagaaaaaattcttcaaatcacaaacgatgtcccaaaaacagtc |
| | | aaaaaagtaggagtttttgttgatgaacctattgattttgtaaaaaaagccattcaagttgctca |
| | | actcgatctggttcagcttcacggaaatgaagatatgaattacattaatcaactagatatttcgg |
| | | ttattaaagcaataagaccagaccaagaatttaaagaatacgaagatgtaattttattatttgat |
| | | agtccacaagctggaagtggtcaagcatttgattgggactctttggtgaccagcggtctgaaaaa |
| | | taaatttttcatcgctggtggacttaatccagaaaatgtagcagctgctattcaacatttccaa |
| | | atgcctacggtgtggatgtttcttctggagtagaaactgacggaattaaaaaccttacaaaaata |
| | | aaaaactttgttcaaaatgcaagccttgcctcatcaaagcaattatttatagaattttaagaat |
| | | cacaaaaaagctaaatgaaaataagattatcccttatttaatgggaagtttagcagttgagcaaa |
| | | taatcaattttccaacaaatcctgatgacattgatattcaactcaaaacgtctgattttgaaaat |
| | | tttgagcaattaacaagtttaatggaaaaattaggttatcagcttattgacttacatgagcataa |
| | | atttgaaaaagctagtattcatgttggctttgcaagtgtggagacccttaaaaactatgccgggg |
| | | ttgactatttgaccattcaacaagaaagaatggaaaatggcgaaaaatatcatcttccaaatgtt |
| | | gaacaatcccttaaaatctatgaggcagcaaaacgagatgagtggcgaggagggaagcaaaaaga |
| | | ttcctttattttcgatgagttaataaaggaacagaagaggaatgacaatgaatgataatcttatt |
| | | gaagagggtgtagagattcgaaatggtctcattattaagtcaattcaaaaagaagatatattaga |
| | | gctttggcaaattagttatggacctaaatctgatttacattggatgtctttcaacgctccctatt |
| | | ttgaggagccaatcctgagttgggaagaattttcaagaaaaatatctcttaaaataaattaacca |
| | | aatgttgcacttattatctttcaaaatcgaatcattggaatgctgtcagcttattgggaagacgg |
| | | taaattacaaaaatggcttgagtttggtatagtgatttatgatagtaaattgtggggacgtggaa |
| | | ttggacaggatgccttatctttttggttgaagcacctttttgaaacttatccgaagattcagcac |
| | | ataggatttacaacttggtcaggaaatcaaggaatgatgagactaggagaaaaaagtggtctaaa |
| | | acttgaagggcaaatcagaaaagttagatattggcaagaaacttggtatgattcaataaaatatg |
| | | gaattttaagagaagaactaaaaaaataaataaaaaaaatcaaaggagcaacaacatgacctaca |
| | | accaacctaacaacaaaggattttacggccaattcgggggccaattcgtacctgagacactaatg |
| | | acagcagtaaaacaattagaagaagcctacgtagatagtaaaaaagaccctctctttcaagcaga |
| | | acttaaagaattacttaaagactatgttggacgagaaaacccactctattatgcaaaacgcttaa |
| | | cagaatatgcgggcggagcaaaaatttatcttaaaagagaagacctaaaccatacaggagcacac |
| | | aaaattaacaatgccctcggacaagtcctccttgccaaaaaaatgggaaaaaataaagtcattgc |
| | | tgaaacaggtgcaggccaacacggtgtcgcaagcgcaaccgcggctgccctctttggcatggaat |
| | | gtacgatttatatgggtgaagaagacgttaaaagacaatctctcaatgtctttcgcatggaatta |
| | | ctcggggcaaaagttcattcagtaactgatggttcacgcgtacttaaagatgcggttaatgcagc |
| | | acttagagcatgggttgctcaagttgaagatacgcattatgtaatgggctcagttcttggaccac |
| | | atccatttccacaaattgtgcgtgattatcaagctgttattggacaggaagcgcgtgcccaattt |
| | | ttagaaaaagaaaataaacttccagatgctttagtagcttgtgtcggtggaggttcaaattctat |
| | | gggactttttttatcccttcgttaatgatgaatcagttgccatgtatggtgttgaagccgctggcc |
| | | ttgggattgatacaccacatcatgcggcaacaattactaaaggccgccccggtgttcttcacgga |
| | | acactcatggatgtccttcaagatgaaaatggtcaaatgttagaagcctttagtatttcagccgg |
| | | tttagactatccaggaatcggaccagaacactcttatttcaatgctgttggacgagcaaaatatg |
| | | ttgatattacagatgaagaagcacttgaaggttttaaaatcttatctagaactgaaggaattatc |
| | | ccagcactagaaagttctcatgctatcgcctatgcagtcaaattagcaaaagaattaggagcaga |
| | | taaatcaatgattgtttgtctttcaggacgtggagataaggatgtggttcaagttaaagaacgac |
| | | ttgaagcagaaaaagaggtgaaaaaatgaaaactttacaaatgactttaagcaataaaaaaaata |
| | | attttattccttatatcatggctggcgaccatgaaaaaggcttagaaggtcttaaagaaaccatt |
| | | caactgcttgagcaagctgggagttccgctattgaaattggcgttccattttcagatccggttgc |
| | | tgatggtccagtcatcgaacaagcaggtttgcgtgcgttagcaagaaatgtatcactttcaagta |
| | | ttcttgaaaccttaaaaacaattgatacaaaagttcctctagtaattatgacctatttcaatccc |
| | | gtttatcagtttggaattgaaaagtttgttgcagctcttgaaaaaacaccagttaaaggccttat |
| | | cattcctgatttgcctaaagaacatgaggactatatcaaaccatttatcaatgataaagatatct |
| | | gtttagttcctctggtctcattaaccacgccactttctcggcaaaaagaacttgtagccgatgct |
| | | gaaggatttatctatgccgttgcaataaatggagtaactgggaaagaaaatgcttatagtaacca |

TABLE 1-continued

| DNA Sequences | | |
|---|---|---|
| Oper-onic se-quences | Host/ Sequence origin | Sequence |
| | | gcttgaccaacatttaaaagcgttatcttcattaacggatgttcctgttttgacaggatttggaa<br>tttctacattatctgatgtggaccgttttaataaagtgtcctcaggagttattgttggttcaaaa<br>attgttcgtgatttacatgaaggtaaagaaaacgaagttattaaatttattgaaaacgcaatcaa<br>tttttaa (SEQ ID NO: 3) |
| trpDCBA | Prokary-otic/ *C. glutamicum* | atgacttctccagcaacactgaaagttctcaacgcctacttggataaccccactccaaccctgga<br>ggaggcaattgaggtgttcaccccgctgaccgtgggtgaatacgatgacgtgcacatcgcagcgc<br>tgcttgccaccatccgtactcgcggtgagcagttcgctgatattgccggcgctgccaaggcgttc<br>ctcgcggcggctcgtccgttcccgattactggcgcaggtttgctagattccgctggtactggtgg<br>cgacggtgccaacaccatcaacatcaccaccggcgcatccctgatcgcagcatccggtggagtg<br>aagctggttaagcacggcaaccgttcggtgagctccaagtccggctccgccgatgtgctggaag<br>cgctgaatattcctttgggccttgatgtggatcgtgctgtgaagtggttcgaagcgtccaacttc<br>accttcctgttcgcacctgcgtacaaccctgcgattgcgcatgtgcagccggttcgccaggcgct<br>gaaattccccaccatcttcaacacgcttggaccattgctgtccccggcgcgcccggagcgtcaga<br>tcatgggcgtggccaatgccaatcatggacagctcatcgccgaggtcttccgcgagttgggccgt<br>acacgcgcgcttgttgtgcatggcgcaggcaccgatgagatcgcagtccacggcaccaccttggt<br>gtgggagcttaaagaagacggcaccatcgagcattacaccatcgagcctgaggaccttggcctt<br>ggccgctacacccttgaggatctcgtaggtggcctcggcactgagaacgccgaagctatgcgc<br>gctactttcgcgggcaccggccctgatgcacaccgtgatgcgttggctgcgtccgcaggtgcga<br>tgttctacctcaacggcgatgtcgactccttgaaagatggtgcacaaaaggcgctttccttgctt<br>gccgacggcaccacccaggcatggttggccaagcacgaagagatcgattactcagaaaaggagt<br>cttccaatgactagtaataatctgcccacagtgttggaaagcatcgtcgagggtcgtcgcggaca<br>cctggaggaaattcgcgctcgcatcgctcacgtggatgtggatgcgcttccaaaatccacccgtt<br>ctctgtttgattccctcaaccagggtaggggaggggcgcgtttcatcatggagtgcaagtccgca<br>tcgccttctttgggaatgattcgtgagcactaccagccgggtgaaatcgctcgcgtgtactctcg<br>ctacgccagcggcatttccgtgctgtgcgagccggatcgttttggtggcgattacgatcacctcg<br>ctaccgttgccgctacctctcatcttccggtgctgtgcaaagacttcatcattgatcctgtccag<br>gtacacgcggcgcgttactttggtgctgatgccatcctgctcatgctctctgtgcttgatgatga<br>agagtacgcagcactcgctgccgaggctgcgcgttttgatctggatatcctcaccgaggttattg<br>atgaggaggaagtcgcccgcgccatcaagctgggtgcgaagatctttggcgtcaaccaccgcaac<br>ctgcatgatctgtccattgatttggatcgttcacgtcgcctgtccaagctcattccagcagatgc<br>cgtgctcgtgtctgagtctggcgtgcgcgataccgaaaccgtccgccagctaggtgggcactcca<br>atgcattcctcgttggctcccagctgaccagccaggaaaacgtcgatctggcagcccgcgaatta<br>gtctacggccccaacaaagtctgcggactcacctcaccaagtgcagcacaaaccgctcgcgcagc<br>gggtgcggtctacggcgggctcatcttcgaagaggcatcgccacgcaatgtttcacgtgaaacat<br>tgcaaaaaatcatcgccgcagagcccaacctgcgctacgtcgcggtcagccgtcgcacctccggg<br>tacaaggatttgcttgtcgacggcatcttcgccgtacaaatccacgccccactgcaggacagcgt<br>cgaagcagaaaaggcattgatcgccgccgttcgtgaagaggttggaccgcaggtccaggtctggc<br>gcgcgatctcgatgtccagccccttgggggctgaagtggcagctgcggtggagggtgacgtcgat<br>aagctaattcttgatgcccatgaaggtggcagcggggaagtattcgactgggctacggtgccgg<br>ccgctgtgaaggcaaagtctttgctcgcgggaggcatctctccggacaacgctgcgcaggcact<br>cgctgtgggctgcgcaggtttggacatcaactctggcgtggaatacccgccggtgcaggcac<br>gtgggctggggcgaaagacgccggcgcgctgctgaaaattttcgcgaccatctccacattccatt<br>actaaaggtttaaataggatcatgactgaaaaagaaaacttgggcggctccacgctgctgcctgc<br>atacttcggtgaattcggcggccagttcgtcgcggaatccctcctgcctgctctcgaccagctgg<br>agaaggccttcgttgacgcgaccaacagcccagagttccgcgaagaactcggcggctacctcc<br>gcgattacctcggccgcccaaccccgctgaccgaatgctccaacctgccactcgcaggcgaag<br>gcaaaggctttgcgcggatcttcctcaagcgcgaagacctcgtccacggcggtgcacacaaaa<br>ctaaccaggtgatcggccaggtgctgcttgccaagcgcatgggcaaaacccgcatcatcgcag<br>agaccggcgcaggccagcacggcaccgccaccgctctcgcatgtgcgctcatgggcctcgag<br>tgcgttgtctacatgggcgccaaggacgttgcccgccagcagcccaacgtctaccgcatgcagc<br>tgcacggcgcgaaggtcatccccgtggaatctggttccggcaccctgaaggacgccgtgaatg<br>aagcgctgcgcgattggaccgcaaccttccacgagtcccactaccttctcggcaccgccgccg<br>gcccgcacccattcccaaccatcgtgcgtgaattccacaaggtgatctctgaggaagccaaggc<br>acagatgctagagcgcaccggcaagcttcccgacgttgtggtcgcctgtgtcggtggtggctcc<br>aacgccatcggcatgttcgcagacttcattgacgatgaaggtgtagagctcgtcggcgctgagc<br>cagccggtgaaggcctcgactccggcaagcacggcgcaaccatcaccaacggtcagatcggc<br>atcctgcacggcacccgttcctacctgatgcgcaactccgacggccaagtggaagagtcctact<br>ccatctccgccggacttgattacccaggcgtcggcccacagcacgcacacctgcacgccaccg<br>gccgcgccacctacgttggtatcaccgacgccgaagccctccaagcattccagtacctcgcccg<br>ctacgaaggcatcatccccgcactggaatcctcacacgcgttcgcctacgcactcaagcgcgcc<br>aagaccgccgaagaggaaggccagaacttaaccatcctcgtctccctatccggccgtggcgac<br>aaggacgttgaccacgtgcgccgcaccctcgaagaaaatccagaactgatcctgaaggacaac<br>cgatgagccgttacgacgatctttttgcacgcctcgacacggcaggggagggcgcctttgttccc<br>ttcatcatgctgagcgacccttcaccagaggaggctttccagatcatctccacagcaatcgaagc<br>tggcgcagatgcactggaacttggcgtacctttctccgacccagttgccgatggccccaccgtcg<br>cggaatcccacctccgcgcactcgacggcggcgccaccgtagacagcgcactcgagcagatc<br>aagcgcgtgcgcgcagcctacccagaggttcccatcggaatgctcatctacggcaacgttccttt<br>cacccgtggcttggatcgcttctaccaagagttcgctgaagctggcgcagactccatcctcctgc<br>cagacgtcccagtccgcgaaggcgcaccgttttctgcagcagctgcagcagccggaattgatcc<br>catttacatcgctccggccaacgccagcgagaaaaccctcgagggtgtctccgccgcatcaaag<br>ggctacatctacgccatctcccgcgacggcgtcaccggcaccgaacgtgaatcatccaccgac<br>ggcctgtccgcagtggtggacaacatcaagaaatttgatggcgcacccatcctcttgggcttcgg |

TABLE 1-continued

| DNA Sequences | | |
|---|---|---|
| Operonic sequences | Host/ Sequence origin | Sequence |
| | | catctcatcccctcagcacgtggcagacgcgattgcagcgggtgcttccggtgcgatcacgggt tccgcgatcaccaagatcattgcttcccactgcgaaggtgagcacccgaacccgtccaccattcg agatatggacggtttgaagaaggatctcactgagttcatctctgcgatgaaggcagcgaccaaga aggtttag (SEQ ID NO: 4) |

TABLE 2

| Enzymes | | |
|---|---|---|
| Enzyme/ Source Organism | genbank/ uniprot number | Sequence |
| trpD/ *E. coli* | P00904 | MADILLLDNIDSFTYNLADQLRSNGHNVVIYRNHIPAQTLIER LATMSNPVLMLSPGPGVPSEAGCMPELLTRLRGKLPIIGICLG HQAIVEAYGGYVGQAGEILHGKASSIEHDGQAMFAGLTNPLP VARYHSLVGSNIPAGLTINAHFNGMVMAVRHDADRVCGFQF HPESILTTQGARLLEQTLAWAQQKLEPANTLQPILEKLYQAQT LSQQESHQLFSAVVRGELKPEQLAAALVSMKIRGEHPNEIAG AATALLENAAPFPRPDYLFADIVGTGGDGSNSINISTASAFVA AACGLKVAKHGNRSVSSKSGSSDLLAAFGINLDMNADKSRQ ALDELGVCFLFAPKYHTGFRHAMPVRQQLKTRTLFNVLGPLI NPAHPPLALIGVYSPELVLPIAETLRVLGYQRAAVVHSGGMD EVSLHAPTIVAELHDGEIKSYQLTAEDFGLTPYHQEQLAGGTP EENRDILTRLLQGKGDAAHEAAVAANVAMLMRLHGHEDLQ ANAQTVLEVLRSGSAYDRVTALAARG (SEQ ID NO: 5) |
| trpD/ *C. glutamicum* | P06559 | MTSPATLKVLNAYLDNPTPTLEEAIEVFTPLTVGEYDDVHIAA LLATIRTRGEQFADIAGAAKAFLAAARPFPITGAGLLDSAGTG GDGANTINITTGASLIAASGGVKLVKHGNRSVSSKSGSADVLE ALNIPLGLDVDRAVKWFEASNFTFLFAPAYNPAIAHVQPVRQ ALKFPTIFNTLGPLLSPARPERQIMGVANANHGQLIAEVFREL GRTRALVVHGAGTDEIAVHGTTLVWELKEDGTIEHYTIEPED LGLGRYTLEDLVGGLGTENAEAMRATFAGTGPDAHRDALAA SAGAMFYLNGDVDSLKDGAQKALSLLADGTTQAWLAKHEEI DYSEKESSND (SEQ ID NO: 6) |
| trpD* feedback resistant (S149F, A161E)/*C. glutamicum* | P06559* | MTSPATLKVLNAYLDNPTPTLEEAIEVFTPLTVGEYDDVHIAA LLATIRTRGEQFADIAGAAKAFLAAARPFPITGAGLLDSAGTG GDGANTINITTGASLIAASGGVKLVKHGNRSVSSKSGSADVLE ALNIPLGLDVDRAVKWFEAFNFTFLFAPAYNPEIAHVQPVRQ ALKFPTIFNTLGPLLSPARPERQIMGVANANHGQLIAEVFREL GRTRALVVHGAGTDEIAVHGTTLVWELKEDGTIEHYTIEPED LGLGRYTLEDLVGGLGTENAEAMRATFAGTGPDAHRDALAA SAGAMFYLNGDVDSLKDGAQKALSLLADGTTQAWLAKHEEI DYSEKESSND (SEQ ID NO: 7) |
| trpC/ E. *coli* | P00909 | MQTVLAKIVADKAIWVETRKEQQPLASFQNEVQPSTRHFYDA LQGARTAFILECKKASPSKGVIRDDFDPARIAAIYKHYASAISV LTDEKYFQGSFDFLPIVSQIAPQPILCKDFIIDPYQIYLARYYQA DACLLMLSVLDDEQYRQLAAVAHSLEMGVLTEVSNEEELER AIALGAKVVGINNRDLRDLSIDLNRTRELAPKLGHNVTVISES GINTYAQVRELSHFANGFLIGSALMAHDDLNAAVRRVLLGEN KVCGLTRGQDAKAAYDAGAIYGGLIFVATSPRCVNVEQAQE VMAAAPLQYVGVFRNHDIADVADKAKVLSLAAVQLHGNED QLYIDNLREALPAHVAIWKALSVGETLPARDFQHIDKYVFDN GQGGSGQRFDWSLLNGQTLGNVLLAGGLGADNCVEAAQTG CAGLDFNSAVESQPGIKDARLLASVFQTLRAY (SEQ ID NO: 8) |
| trpC/ *C. glutamicum* | P06560 | MTSNNLPTVLESIVEGRRGHLEEIRARIAHVDVDALPKSTRSL FDSLNQGRGGARFIMECKSASPSLGMIREHYQPGEIARVYSRY ASGISVLCEPDRFGGDYDHLATVAATSHLPVLCKDFIIDPVQV HAARYFGADAILLMLSVLDDEEYAALAAEAARFDLDILTEVI DEEEVARAIKLGAKIFGVNHRNLHDLSIDLDRSRRLSKLIPAD AVLVSESGVRDTETVRQLGGHSNAFLVGSQLTSQENVDLAAR ELVYGPNKVCGLTSPSAAQTARAAGAVYGGLIFEEASPRNVS RETLQKIIAAEPNLRYVAVSRRTSGYKDLLVDGIFAVQIHAPL QDSVEAEKALIAAVREEVGPQVQVWRAISMSSPLGAEVAAA VEGDVDKLILDAHEGGSGEVFDWATVPAAVKAKSLLAGGISP |

TABLE 2-continued

| Enzymes | | |
|---|---|---|
| Enzyme/ Source Organism | genbank/ uniprot number | Sequence |
| | | DNAAQALAVGCAGLDINSGVEYPAGAGTWAGAKDAGALLK IFATISTFHY (SEQ ID NO: 9) |
| trpB/ *E. coli* | P0A879 | MTTLLNPYFGEFGGMYVPQILMPALRQLEEAFVSAQKDPEFQ AQFNDLLKNYAGRPTALTKCQNITAGTNTTLYLKREDLLHGG AHKTNQVLGQALLAKRMGKTEIIAETGAGQHGVASALASAL LGLKCRIYMGAKDVERQSPNVFRMRLMGAEVIPVHSGSATL KDACNEALRDWSGSYETAHYMLGTAAGPHPYPTIVREFQRM IGEETKAQILEREGRLPDAVIACVGGGSNAIGMFADFINETNV GLIGVEPGGHGIETGEHGAPLKHGRVGIYFGMKAPMMQTED GQIEESYSISAGLDFPSVGPQHAYLNSTGRADYVSITDDEALE AFKTLCLHEGIIPALESSHALAHALKMMRENPDKEQLLVVNL SGRGDKDIFTVHDILKARGEI (SEQ ID NO: 10) |
| trpB/ *C. glutamicum* | P06561 | MTEKENLGGSTLLPAYFGEFGGQFVAESLLPALDQLEKAFVD ATNSPEFREELGGYLRDYLGRPTPLTECSNLPLAGEGKGFARI FLKREDLVHGGAHKTNQVIGQVLLAKRMGKTRIIAETGAGQ HGTATALACALMGLECVVYMGAKDVARQQPNVYRMQLHG AKVIPVESGSGTLKDAVNEALRDWTATFHESHYLLGTAAGPH PFPTIVREFHKVISEEAKAQMLERTGKLPDVVVACVGGGSNAI GMFADFIDDEGVELVGAEPAGEGLDSGKHGATITNGQIGILH GTRSYLMRNSDGQVEESYSISAGLDYPGVGPQHAHLHATGR ATYVGITDAEALQAFQYLARYEGIIPALESSHAFAYALKRAKT AEEEGQNLTILVSLSGRGDKDVDHVRRTLEENPELILKDNR (SEQ ID NO: 11) |
| trpA/ *E. coli* | P00895 | MQTQKPTLELLTCEGAYRDNPTALFHQLCGDRPATLLLESAD IDSKDDLKSLLLVDSALRITALGDTVTIQALSGNGEALLALLD NALPAGVESEQSPNCRVLRFPPVSPLLDEDARLCSLSVFDAFR LLQNLLNVPKEEREAMFFGGLFSYDLVAGFEDLPQLSAENNC PDFCFYLAETLMVIDHQKKSTRIQASLFAPNEEEKQRLTARLN ELRQQLTEAAPPLPVVSVPHMRCECNQSDEEFGGVVRLLQKA IRAGEIFQVVPSRRFSLPCPSPLAAYYVLKKSNPSPYMFFMQD NDFTLFGASPESSLKYDATSRQIEIYPIAGTRPRGRRADGSLDR DLDSRIELEMRTDHKELSEHLMLVDLARNDLARICTPGSRYV ADLTKVDRYSYVMHLVSRVVGELRHDLDALHAYRACMNM GTLSGAPKVRAMQLIAEAEGRRRGSYGGAVGYFTAHGDLDT CIVIRSALVENGIATVQAGAGVVLDSVPQSEADETRNKARAV LRAIATAHHAQETF (SEQ ID NO: 12) |
| trpA/ *C. glutamicum* | P06562 | MSRYDDLFARLDTAGEGAFVPFIMLSDPSPEEAFQIISTAIEAG ADALELGVPFSDPVADGPTVAESHLRALDGGATVDSALEQIK RVRAAYPEVPIGMLIYGNVPFTRGLDRFYQEFAEAGADSILLP DVPVREGAPFSAAAAAAGIDPIYIAPANASEKTLEGVSAASKG YIYAISRDGVTGTERESSTDGLSAVVDNIKKFDGAPILLGFGIS SPQHVADAIAAGASGAITGSAITKIIASHCEGEHPNPSTIRDMD GLKKDLTEFISAMKAATKKV (SEQ ID NO: 13) |
| Tryptophan Decarboxylase/ *P. cubensis* | P0DPA6 | MQVIPACNSAAIRSLCPTPESFRNMGWLSVSDAVYSEFIGELA TRASNRNYSNEFGLMQPIQEFKAFIESDPVVHQEFIDMFEGIQ DSPRNYQELCNMFNDIFRKAPVYGDLGPPVYMIMAKLMNTR AGFSAFTRQRLNLHFKKLFDTWGLFLSSKDSRNVLVADQFDD RHCGWLNERALSAMVKHYNGRAFDEVFLCDKNAPYYGFNS YDDFFNRRFRNRDIDRPVVGGVNNTTLISAACESLSYNVSYD VQSLDTLVFKGETYSLKHLLNNDPFTPQFEHGSILQGFLNVTA YHRWHAPVNGTIVKIINVPGTYFAQAPSTIGDPIPDNDYDPPP YLKSLVYFSNIAARQIMFIEADNKEIGLIFLVFIGMTEISTCEAT VSEGQHVNRGDDLGMFHFGGSSFALGLRKDCRAEIVEKFTEP GTVIRINEVVAALKA (SEQ ID NO: 14) |
| Tryptophan Decarboxylase/ *P. cyanescens* | ASU62242 | MQVLPACQSSALKTLCPSPEAFRKLGWLPTSDEVYNEFIDDLT GRTCNEKYSSQVTLLKPIQDFKTFIENDPIVYQEFISMFEGIEQS PTNYHELCNMFNDIFRKAPLYGDLGPPVYMIMARIMNTQAGF SAFTKESLNFHFKKLFDTWGLFLSSKNSRNVLVADQFDDKHY GWFSERAKTAMMINYPGRTFEKVFICDEHVPYHGFTSYDDFF NRRFRDKDTDRPVVGGVTDTTLIGAACESLSYNVSHNVQSLD TLVIKGEAYSLKHLLHNDPFTPQFEHGSIIQGFLNVTAYHRWH SPVNGTIVKIVNVPGTYFAQAPYTIGSPIPDNDRDPPPYLKSLV YFSNIAARQIMFIEADNKDIGLIFLVFIGMTEISTCEATVCEGQH VNRGDDLGMFHFGGSSFALGLRKDSKAKILEKFAKPGTVIRIN ELVASVRK (SEQ ID NO: 15) |

TABLE 2-continued

| Enzymes | | |
|---|---|---|
| Enzyme/ Source Organism | genbank/ uniprot number | Sequence |
| Tryptophan Decarboxylase/ *P. cyanescens* | PPQ80975 | MQVLTACYTSTLKSLLPSFDAFRSMGWLPVSDKTYNEWIGDLRSRASDKNYTSQVGLIQPIKDFKAFIESDPVVHQEFITMFEGIEESPRNYEELCHMFNDIFRKAPVYGDLGPPVYMVMARIMNTQAGFSAFTKQSLNSHFKRLFDTWGVFLSSKESRYVLVTDQFDDNHYGWLSDRAKSAMVKHYYGRTFEQVFICDEHAPYHGFQSYDDFFNRRFRDRDIDRPVVGGIENTTLISAACESLSYNVCHDLQSLDTLFVKGESYSLKHLLNDDPFARQFEHGSILQGFLNVTAYHRWHAPVNGTILKIINVPGTYFAQAPHTIGDSLDSDHPPYLKSLAYFSNIAARQIMFIEADNKDIGLIFLVFIGMTEISTCEATVSEGQHVNRGDDLGMFHFGGSSFALGLRKDCKAEIFERFAEQGTVIKINEVVAAVKD (SEQ ID NO: 16) |
| Tryptophan Decarboxylase/ *G. dilepis* | PPQ70875 | MAKTLRPTAQAFRELGWLPASDGVYNKFMKDLTNRASNENHLCHVALLQPIQDFKTFIENDPVVYQEFVCMFEGIEESPRNYHELCNMFNEIFRRAPYYGDLGPPVYMAMAKIMNTRAGFSAFTRESLNFHFKRLFDTWGLFLSSPASRDVLVADKFDSKHYGWFSEPAKAAMMAQYDGRTFEQVFICDETAPYHGFKSYDDFFNRKFRAMDIDRPVVGGIANTTLIGSPCEALSYNVSDDVHSLETLYFKGEGYSLRHLLHDDPSTEQFEHGSIIQGFLNITGYHRWHAPVSGTIMKIVDVPGTYFAQAPSTIGDPFPVNDYDPQAPYLRSLAYFSNIAARQIIFIQADNEDIGLIYLILIGMTEVSTCEALVCPGQHVERGDDLGMFHFGGSSFALGLRKNSKAAILEELKTQGTVIKVNDVIAAVQA (SEQ ID NO: 17) |
| Tryptophan Decarboxylase/ *H. sapiens* | P20711 | MNASEFRRRGKEMVDYMANYMEGIEGRQVYPDVEPGYLRPLIPAAAPQEPDTFEDIINDVEKIIMPGVTHWHSPYFFAYFPTASSYPAMLADMLCGAIGCIGFSWAASPACTELETVMMDWLGKMLELPKAFLNEKAGEGGGVIQGSASEATLVALLAARTKVIHRLQAASPELTQAAIMEKLVAYSSDQAHSSVERAGLIGGVKLKAIPSDGNFAMRASALQEALERDKAAGLIPFFMVATLGTTTCCSFDNLLEVGPICNKEDIWLHVDAAYAGSAFICPEFRHLLNGVEFADSFNFNPHKWLLVNFDCSAMWVKKRTDLTGAFRLDPTYLKHSHQDSGLITDYRHWQIPLGRRFRSLKMWFVFRMYGVKGLQAYIRKHVQLSHEFESLVRQDPRFEICVEVILGLVCFRLKGSNKVNEALLQRINSAKKIHLVPCHLRDKFVLRFAICSRTVESAHVQRAWEHIKELAADVLRAERE (SEQ ID NO: 18) |
| Tryptophan Decarboxylase/ *B. atrophaeus* | I0DFJ0 | MSENLQLSAEEMRQLGYQAVDLIIDHMNHLKSKPVSETIDSDILRNKLTESIPENGSDPKELLHFLNRNVFNQITHVDHPHFLAFVPGPNNYVGVVADFLASGFNVFPTAWIAGAGAEQIELTTINWLKSMLGFPDSAEGLFVSGGSMANLTALTVARQAKLNNDIENAVVYFSDQTHFSVDRALKVLGFKHHQICRIETDEHLRISVSALKKQIKEDRTKGKKPFCVIANAGTTNCGAVDSLNELADLCNDEDVWLHADGSYGAPAILSEKGSAMLQGIHRADSLTLDPHKWLFQPYDVGCVLIRNSQYLSKTFRMMPEYIKDSETNVEGEINFGECGIELSRRFRALKVWLSFKVFGVAAFRQAIDHGIMLAEQVEAFLGKAKDWEVVTPAQLGIVTFRYIPSELASTDTINEINKKLVKEITHRGFAMLSTTELKEKVVIRLCSINPRTTTEEMLQIMMKIKALAEEVSISYPCVAE (SEQ ID NO: 19) |
| Tryptophan Decarboxylase/ *C. roseus* | P17770 | MGSIDSTNVAMSNSPVGEFKPLEAEEFRKQAHRMVDFIADYYKNVETYPVLSEVEPGYLRKRIPETAPYLPEPLDDIMKDIQKDIIPGMTNWMSPNFYAFFPATVSSAAFLGEMLSTALNSVGFTWVSSPAATELEMIVMDWLAQILKLPKSFMFSGTGGGVIQNTTSESILCTIIAARERALEKLGPDSIGKLVCYGSDQTHTMFPKTCKLAGIYPNNIRLIPTTVETDFGISPQVLRKMVEDDVAAGYVPLFLCATLGTTSTTATDPVDSLSEIANEFGIWIHVDAAYAGSACICPEFRHYLDGIERVDSLSLSPHKWLLAYLDCTCLWVKQPHLLLRALTTNPEYLKNKQSDLDKVVDFKNWQIATGRKFRSLKLWLILRSYGVVNLQSHIRSDVAMGKMFEEWVRSDSRFEIVVPRNFSLVCFRLKPDVSSLHVEEVNKKLLDMLNSTGRVYMTHTIVGGIYMLRLAVGSSLTEEHHVRRVWDLIQKLTDDLLKEA (SEQ ID NO: 20) |
| Tryptamine n-methyltrans-ferase/ *P. cubensis* | ASU62238.1 | MHIRNPYRTPIDYQALSEAFPPLKPFVSVNADGTSSVDLTIPEAQRAFTAALLHRDFGLTMTIPEDRLCPTVPNRLNYVLWIEDIFNYTNKTLGLSDDRPIKGVDIGTGASAIYPMLACARFKAWSMVGTEVERKCIDTARLNVVANNLQDRLSILETSIDGPILVPIFEATEEYEYEFTMCNPPFYDGAADMQTSDAAKGFGFGVGAPHSGTVIEMSTEGGESAFVAQMVRESLKLRTRCRWYTSNLGKLKSLKEIVGLLKELEISNYAINEYVQGSTRRYAVAWSFTDIQLPEELSRPSNPELSSLF (SEQ ID NO: 21) |

TABLE 2-continued

| Enzymes | | |
|---|---|---|
| Enzyme/ Source Organism | genbank/ uniprot number | Sequence |
| Tryptamine n-methyltransferase/*P. cyanescens* | PPQ83230.1 | MHIRNPYRSPIDYQALVEAFPPLRPYVTVNQDNTTSIDLTVPEVQRLYTAALLHRDFGLVIDLPEDRLCPTLLTRTPRLNYVLWVEDILKVTNTALGLSEDRPVKGIDIGTGAAAIYPMLACARFKTWSMIGTEIDRKCIDTARVNVLTNNLQDRLSIIETSIDGPILVPIFEATTDYEYDFTMCNPPFYDGAADMQTSDAAKGFGFGVNAPHSGTVIEMSTEGGESAFVAQMVRESLDHRTRCRWFTSNLGKLKSLHEIVGLLREHQISNYAINEYVQGTTRRYAIAWSFTNIRLPEDLTRPSNPELSSLF (SEQ ID NO: 22) |
| Tryptamine n-methyltransferase/*P. cyanescens* | PPQ80976.1 | MHNRNPYRDVIDYQALAEAYPPLKPHVTVNADNTASIDLTIPEVQRQYTAALLHRDFGLTITLPEDRLCPTVPNRLNYVLWIEDIFQCTNKALGLSDDRPVKGVDIGTGASAIYPMLACARFKQWSMIATEVERKCIDTARLNVLANNLQDRLSILEVSVDGPILVPIFDTFERATSDYEFEFTMCNPPFYDGAADMQTSDAAKGFGFGVNAPHSGTVIEMATEGGEAAFVAQMVRESMKLQTRCRWFTSNLGKLKSLHEIVALLRESQITNYAINEYVQGTTRRYALAWSFTDIKLTEELYRPSNPELGPLCSTFV (SEQ ID NO: 23) |
| Tryptamine n-methyltransferase/*G. dilepis* | PPQ70884.1 | MHIRNPYLTPPDYEALAEAFPALKPYVTVNPDKTTTIDFAIPEAQRLYTAALLYRDFGLTITLPPDRLCPTVPNRLNYVLWIQDILQITSAALGLPEARQVKGVDIGTGAAAIYPILGCSLAKNWSMVGTEVEQKCIDIARQNVISNGLQDRITITANTIDAPILLPLFEGDSNFEWEFTMCNPPFYDGAADMETSQDAKGFGFGVNAPHTGTVVEMATDGGEAAFVSQMVRESLHLKTRCRWFTSNLGKLKSLHEIVGLLREHQITNYAINEYVQGTTRRYAIAWSFTDLRLSDHLPRPPNPDLSALF (SEQ ID NO: 24) |
| Tryptamine n-methyltransferase/*H. sapiens* | O95050 | MKGGFTGGDEYQKHFLPRDYLATYYSFDGSPSPEAEMLKFNLECLHKTFGPGGLQGDTLIDIGSGPTIYQVLAACDSFQDITLSDFTDRNREELEKWLKKEPGAYDWTPAVKFACELEGNSGRWEEKEEKLRAAVKRVLKCDVHLGNPLAPAVLPLADCVLTLLAMECACCSLDAYRAALCNLASLLKPGGHLVTTVTLRLPSYMVGKREFSCVALEKEEVEQAVLDAGFDIEQLLHSPQSYSVTNAANNGVCFIVARKKPGP (SEQ ID NO: 25) |
| Tryptamine n-methyltransferase/A. sp. ANC 4654 | WP_086164675.1 | MIYKFYQQHIFPHLLNQVMQTPSLMDQRRQLLLPIAGDVLEIGFGTGVNLPFYQNVETLYALEPNADLYQLAAKRIHESTIHVQHIQAYAEKLPFADASLDHIVSTWTLCSIENLAQALIEMYRVLKPNGTLHLVEHVQYQDNAKLQHLQNLLTPIQKRLADGCHLNRNIEQALRDAHFDFTEQHYFAAQGIPKLAQRMFFARAQKQPE (SEQ ID NO: 26) |
| Tryptamine benzoyl transferase/*O. sativa* subsp. *japonica* | A0A1L2EH62 | MEITSSAMLKTTTTPPHPLAGEKVPLSAFDRAAFDVFVPLVFAYRAPAPSSEAVKEGLRVAVAAYPLVSGRIAVDGQGRRRRRRVLHVNNEGVLVLDATVEVDLDAVLAANVATDLYPALPEHSFGAALLQVQLTRFGCGGLVVGLIGHHHVFDGHSMSTFCATWARAVRDSEAFIVPSPSLDRAITGVPRSPPAPVFDHRSIEFKVGNKSSDSSGAAAAAAVEKIANIGVRFTAKFVAELKARVGGRCSTFECVLAHAWKKITAARGLKPEEFTRVRVAVNCRRRANPPAPADLFGNMVLWAFPRLQVRRLLSSSYRDVVGAIRAAVARVDAEYIQSFVDYVEVADARGEELAATAAEPGETLCPDLEVDSWLGFRFHEMDLGTGPPAAVLSPDLPIEGLMILVPVGGDGGGVDLFVALADDHAQAFEQICYSLEEHAMIHSHL (SEQ ID NO: 27) |
| Serotonin N-acetyltransferase/*H. sapiens* | Q16613 | MSTQSTHPLKPEAPRLPPGIPESPSCQRRHTLPASEFRCLTPEDAVSAFEIEREAFISVLGVCPLYLDEIRHFLTLCPELSLGWFEEGCLVAFIIGSLWDKERLMQESLTLHRSGGHIAHLHVLAVHRAFRQQGRGPILLWRYLHHLGSQPAVRRAALMCEDALVPFYERFSFHAVGPCAITVGSLTFMELHCSLRGHPFLRRNSGC (SEQ ID NO: 28) |
| Dopamine N-acetyltransferase/*D. melanogaster* | Q94521 | MEVQKLPDQSLISSMMLDSRCGLNDLYPIARLTQKMEDALTVSGKPAACPVDQDCPYTIELIQPEDGEAVIAMLKTFFFKDEPLNTFLDLGECKELEKYSLKPLPDNCSYKAVNKKGEIIGVFLNGLMRRPSPDDVPEKAADSCEHPKFKKILSLMDHVEEQFNIFDVYPDEELILDGKILSVDTNYRGLGIAGRLTERAYEYMRENGINVYHVLCSSHYSARVMEKLGFHEVFRMQFADYKPQGEVVFKPAAPHVGIQVMAKEVGPAKAAQTKL (SEQ ID NO: 29) |

TABLE 2-continued

Enzymes

| Enzyme/ Source Organism | genbank/ uniprot number | Sequence |
|---|---|---|
| Arylalkyla-mine N-acetyltrans-ferase/*D. rerio* | Q9PVD7 | MMAPQVVSSPFLKPFFLKTPISVSSPRRQRRHTLPASEFRNLTP QDAISVFEIEREAFISVSGECPLTLDEVLVFLGQCPELSMGWFE EGQLVAFIIGSGWDKEKLEQEAMSTHVPDSPTVHIHVLSVHR HCRQQGKGSILLWRYLQYLRCLPGLRRALLVCEEFLVPFYQK AGFKEKGPSAISVAALTFTEMEYQLGGLAYARRNSGC (SEQ ID NO: 30) |
| Tryptamine hydroxycin-namoyltrans-ferase/*O. sativa* | Q338X7 | MAAVTVEITRSEVLRPSPASAGGGEMVPLTVFDRAATDGYIP TMFAWDAAAAAALSNDAIKDGLAAVLSRFPHLAGRFAVDER GRKCFRLNNAGARVLEASAAGDLADALAHDVAAHVNQLYP QADKDRVDEPLLQVQLTRYTCGGLVIGAVSHHQVADGQSMS VFFTEWAAAVRTAGAALPTPFLDRSAVAAPRIPPAPAFDHRN VEFRGEGSRSHSYGALPLERMRNLAVHFPPEFVAGLKARVGG ARCSTFQCLLAHAWKKITAARDLSPKEYTQVRVAVNCRGRA GPAVPTDYFGNMVLWAFPRMQVRDLLSASYAAVVGVIRDA VARVDERYIQSFVDFGEVAAGDELAPTAAEPGTAFCPDLEVD SWIGFRFHDLDFGGGPPCAFLPPDVPIDGLLIFVPSCAAKGGVE MFMALDDQHVEALRQICYSMD (SEQ ID NO: 31) |
| Tryptamine 4-hydroxylase/ *P. cubensis* | P0DPA7.1 | MIAVLFSFVIAGCIYYIVSRRVRRSRLPPGPPGIPIPFIGNMFDM PEESPWLTFLQWGRDYNTDILYVDAGGTEMVILNTLETITDLL EKRGSIYSGRLESTMVNELMGWEFDLGFITYGDRWREERRMF AKEFSEKGIKQFRHAQVKAAHQLVQQLTKTPDRWAQHIRHQI AAMSLDIGYGIDLAEDDPWLEATHLANEGLAIASVPGKFWVD SFPSLKYLPAWFPGAVFKRKAKVWREAADHMVDMPYETMR KLAPQGLTRPSYASARLQAMDLNGDLEHQEHVIKNTAAEVN VGGGDTTVSAMSAFILAMVKYPEVQRKVQAELDALTNNGQI PDYDEEDDSLPYLTACIKELFRWNQIAPLAIPHKLMKDDVYR GYLIPKNTLVFANTWAVLNDPEVYPDPSVFRPERYLGPDGKP DNTVRDPRKAAFGYGRRNCPGIHLAQSTVWIAGATLLSAFNI ERPVDQNGKPIDIPADFTTGFFRHPVPFQCRFVPRTEQVSQSVS GP (SEQ ID NO: 32) |
| Tryptamine 4-hydroxylase/ *P. cyanescens* | ASU62250.1 | MIVLLVSLVLAGCIYYANARRVRRSRLPPGPPGIPLPFIGNMFD MPSESPWLRFLQWGRDYHTDILYLNAGGTEIIILNTLDAITDLL EKRGSMYSGRLESTMVNELMGWEFDLGFITYGERWREERRM FAKEFSEKNIRQFRHAQIKAANQLVRQLIKTPDRWSQHIRHQI AAMSLDIGYGIDLAEDDPWIAATQLANEGLAEASVPGSFWVD SFPALKYLPSWLPGAGFKRKAKVWKEGADHMVNMPYETMK KLTVQGLARPSYASARLQAMDPDGDLEHQEHVIRNTATEVN VGGGDTTVSAVSAFILAMVKYPEVQRQVQAELDALTSKGVV PNYDEEDDSLPYLTACVKEIFRWNQIAPLAIPHRLIKDDVYRG YLIPKNALVYANSWAVLNDPEEYPNPSEFRPERYLSSDGKPDP TVRDPRKAAFGYGRRNCPGIHLAQSTVWIAGATLLSVFNIERP VDGNGKPIDIPATFTTGFFRHPEPFQCRFVPRTQEILKSVSG (SEQ ID NO: 33) |
| Tryptamine 4-hydroxylase/ *P. cyanescens* | PPQ98746.1 | MINLPLSLVLVGCVYYIVSRRIRRSRLPPGPPGIPIPFVGNMYD MPSESPWLTFLQWGREYNDRGLTTIFRVESTMVNKLMGWEF DLGFITYGDRWREERRMFSKEFSEKAIKQFRHSQVKAAHRFV QQLAANGEPSRLPHYIRHQIAAMSLDIGYGVDLAQDDPWLEA AHLANEGLATASVPGTFWIDSFPALKYLPSWFPGAGFKRQAK IWKEAADHMVNMPYERMKKLAPQGLARPSYASARLQAMDP NGDLEYQEQVIKNTASQVNVGGGDTTVSAVSAFILAMVIYPE VQRKVQAELDAVLSNGRIPDYDEENDSMPYLTACVKELFRW NQIAPLAIPHKLVKDDIYRGYLIPKNTLVFANSWAVLNDPEVY PDPSVFRPERYLGPDGKPNDTVRDPRKAAFGYGRRNCPGIHL ALSTVWITAATLLSVFDIERPVDHKGNPIDIPAAFTKGFFRHPE PFQCRFVPRNEDSLKSLSGL (SEQ ID NO: 34) |
| Tryptamine 4-hydroxylase/ *G. dilepis* | PPQ70878.1 | MQGNPAVLLLLLTLTLCVYYAHSRRARRARLPPGPPGIPLPFV GNLFDMPSNSPWLTYLQWGETYQTDIIYLNAGGTEMVILNTL EAITDLLEKRGSIYSGRFESTMVNELMGWDFDLGFITYGERW REERRMFSKEFNEKNIKQFRHAQIRAANLLVGQLTKTPERWH QLIRHQIAAMSLDIGYGIDLLEGDPWLEATQLANEGLAIASVP GSFWVDSLPILKYMPSWFPGAEFKRKAKVWRESTDHMINMP YEKMKKLMVQDLVRPSYASARLQEMDPNGDLQHQEHVIRN TAMEVNVGGADTTVSAVAAFILAMVKYPDVQRKVQAELDA VGCRDELPEFDEDNDALPYLTACVKEIFRWNQVAPLAIPHRL DKDDHYRGYIIPKNALVFANTWAVLNDPSVYPDPSEFRPERY LGPDGKPDPRIRDPRKAAFGYGRRACPGIHLAQSTVWIVGAT LLSVFDIERPMDANGKPIDIPAAFTTGFFRYSIHDCLVVETMHP ANTVCVDIPNPSDADSFLVPKRLSNPHPIIDLPSRNPACQEDGV VALSNAWRSTLPVQDV (SEQ ID NO: 35) |

TABLE 2-continued

| Enzymes | | |
|---|---|---|
| Enzyme/ Source Organism | genbank/ uniprot number | Sequence |
| P450 reductase/*S. cerevisiae* | NP_011908.1 | MPFGIDNTDFTVLAGLVLAVLLYVKRNSIKELLMSDDGDITA VSSGNRDIAQVVTENNKNYLVLYASQTGTAEDYAKKFSKEL VAKFNLNVMCADVENYDFESLNDVPVIVSIFISTYGEGDFPDG AVNFEDFICNAEAGALSNLRYNMFGLGNSTYEFFNGAAKKAE KHLSAAGAIRLGKLGEADDGAGTTDEDYMAWKDSILEVLKD ELHLDEQEAKFTSQFQYTVLNEITDSMSLGEPSAHYLPSHQLN RNADGIQLGPFDLSQPYIAPIVKSRELFSSNDRNCIHSEFDLSGS NIKYSTGDHLAVWPSNPLEKVEQFLSIFNLDPETIFDLKPLDPT VKVPFPTPTTIGAAIKHYLEITGPVSRQLFSSLIQFAPNADVKE KLTLLSKDKDQFAVEITSKYFNIADALKYLSDGAKWDTVPMQ FLVESVPQMTPRYYSISSSSLSEKQTVHVTSIVENFPNPELPDA PPVVGVTTNLLRNIQLAQNNVNIAETNLPVHYDLNGPRKLFA NYKLPVHVRRSNFRLPSNPSTPVIMIGPGTGVAPFRGFIRERVA FLESQKKGGNNVSLGKHILFYGSRNTDDFLYQDEWPEYAKKL DGSFEMVVAHSRLPNTKKVYVQDKLKDYEDQVFEMINNGAF IYVCGDAKGMAKGVSTALVGILSRGKSITTDEATELIKMLKTS GRYQEDVW (SEQ ID NO: 36) |
| P450 reductase/*A. niger* | GAQ41948.1 | MAQLDTLDLVVLAVLLVGSVAYFTKGTYWAVAKDPYASTG PAMNGAAKAGKTRNIIEKMEETGKNCVIFYGSQTGTAEDYAS RLAKEGSQRFGLKTMVADLEEYDYENLDQFPEDKVAVFVLA TYGEGEPTDNAVEFYQFFTGDDVAFESGASADEKPLSKLKYV AFGLGNNTYEHYNAMVRQVDAAFQKLGAQRIGSAGEGDDG AGTMEEDFLAWKEPMWAALSESMDLQEREAVYEPVFCVTE NESLSPEDESVYLGEPTQSHLQGTPKGPYSAHNPFIAPIAESRE LFTVKDRNCLHMEISIAGSNLSYQTGDHIAVWPTNAGAEVDR FLQVFGLEGKRDSVINIKGIDVTAKVPIPTPTTYDAAVRYYME VCAPVSRQFVATLAAFAPDEESKAEIVRLGSDKDYFHEKVTN QCFNIAQALQSITSKPFSAVPFSLLIEGITKLQPRYYSISSSSLVQ KDKISITAVVESVRLPGASHMVKGVTTNYLLALKQKQNGDPS PDPHGLTYSITGPRNKYDGIHVPVHVRHSNFKLPSDPSRPIIMV GPGTGVAPFRGFIQERAALAAKGEKVGPTVLFFGCRKSDEDF LYKDEWKTYQDQLGDNLKIITAFSREGPQKVYVQHRLREHSE LVSDLLKQKATFYVCGDAANMAREVNLVLGQIIAAQRGLPA EKGEEMVKHMRSSGSYQEDVWS (SEQ ID NO: 37) |
| P450 reductase/*P. cyanescens* | PPQ81263.1 | MTDPNRTTFSSALHPLAVVSMASSSSDVFVLGLGVVLAALYIF RDQLFAASKPKVAPVSTTKPANGSANPRDFIAKMKQGKKRIV IFYGSQTGTAEEYAIRLAKEAKQKFGLASLVCDPEEYDFEKLD QLPEDSIAFFVVATYGEGEPTDNAVQLLQNLQDDSFEFSNGER KLSGLKYVVFGLGNKTYEHYNLIGRTVDAQLAKMGAVRVGE RGEGDDDKSMEEDYLEWKDGMWDAFAAAMGVEEGQGGDS ADFVVSELESHPPEKVYLGEYSARALTKTKGIHDAKNPLAAPI TVARELFQSVVDRNCVHVEFNIEGSGITYQHGDHVGLWPLNP DVEVERLLCVLGLTEKRDAVISIESLDPALAKVPFPVPTTYAA VLRHYIDVSAVAGRQILGTLSKFAPTPEAEAFLKNLNTNKEEY HNVVANGCLKLGEILQVATGNDITVAPTPGNTTKWPIPFDIIV SAIPRLQPRYYSISSSPKVHPNTIHATVVVLKYENVPTDPIPRK WVYGVGSNFLLNLKHAINKEPVPFITQNGEQRVGVPEYLIAG PRGSYKTESHFKAPIHVRRSTFRLPTNPKSPVIMIGPGTGVAPF RGFVQERVALARRSVEKNGPESLNDWGRISLFYGCRRSDEDF LYKDEWPQYQEELKGKFKLHCAFSRENYKPDGSKIYVQDLI WEDREHIADAILNGKGYVYICGEAKSMSKQVEEVLARILGEA KGGSGAVEGVAEIKLLKERSRLMLDYELAFRKFSQLQFARVA TFAMLRSSFSLQRLFSTSSALRNVQRPIRDHLQKQDAPWEPRV AESAQSVSEEILKAQTPLQVPTNAKATTSDSRTDSREPLTAYD LQLVKKRVREWSEQAMIALRNRADDFTAHTKTTFSQLGLQL NRVTGYEEIEALKRGVVEQEERINVARQAARKAKVAYEEAV VQRSNSQREVNDLLQRKSSWMDSDVGRFTTLVRQDHLYEQE EARAKAAVEETEEAVDREFSKLLRTILARYHEEQVWSDKIRS ASTYGSLAALGLNMLVFIMAIVVVEPWKRRRLAQTFERKIEE LSEENGIKLDATMLSIAQQIEQQVNLIGSLKDDISRNAPVIPEP AQEVRAETEIEEETSPFVSLEFLPLSRRQLEVAAVGAGAFASN LWFGFGDDALELLMLSTRANKVPPRNLSRIHMTSFIIKAHEDR PTNSTWKQDLECAFCRIIRGELPASKVYENDKVIAILDIMPLRK GHTLVIPKAHISRLSELPSELASSVGEAVCKVAHALTQALDNT GLNVVCNQEYAQAVPHVHYHVIPAPKFGYPGHGVESTNGVV GGKAPLTHREMHQKEFEAREELDDDDAKVLLKSIRARL (SEQ ID NO: 38) |

TABLE 2-continued

| Enzymes | | |
|---|---|---|
| Enzyme/ Source Organism | genbank/ uniprot number | Sequence |
| P450 reductase/*P. cyanescens* | PPQ83917.1 | MSVSEDDHRGLLIVYATETGNAQDAADYIARQCRRIAFQCRV<br>VNIDSFLLPDLLSETIVIFVVSTTGSGVEPRSMTPLWTSLLRGD<br>LPTDTFEDLYFSVFGLGDTAYEKFCWAAKKLSRRLESIGGIEF<br>YMRGEGDEQHPLGIDGALQPWTDGLINKLLEVAPLPPGEEIKP<br>INDVPLPRVLLKDTSKTALNHSADPLKSDLQYHKAIVKKNDRI<br>TAADWYQDVRHLVFDFQDNIQYSPGDVAVIHPVALEHDVDA<br>FLVTMSWQNIADEPFEIEQAMYDQSLPDHLPPITTLRTLFTRFL<br>DFNAVPRRSFFQYLRYFTSDEREQEKLDEFLSAAGADELYEY<br>CYRVRRTIHEVLSEFRHVKIPKGYIFDVFPPLRPREFSIASSIKT<br>HLHQIHLCVAIVKYRTKLKIPRKGVCTYYLSILKPGDTLLVGIR<br>RGLLRLPGKNDTPVIFIGPGTGIAPMRSAIEQRIANGCHENTLY<br>FGCRSASKDQHYGSEWQAYAANQELKYRSAFSRDGVEGEAR<br>VYVQDLIRQDSERIWDLVGHHKAWVLVSGSSNKMPAAVKD<br>AVAYAVEKYGGLSAEEAKEYVHLMVKEGRLIEECWS<br>(SEQ ID NO: 39) |
| P450 reductase/*P. cyanescens* | PPQ77370.1 | MSLNGSGLLTPSSEVTLSSPSTPVLIYTFPQSNGTRPKSPVYIHI<br>DDPGVQVSTLVEYISSQPENSSSVYIYDVAEQVGFGTSTKQW<br>AKQGLDISPVVDLQTRAGAGLSLVGRLSQGTSIDAVKGTVLT<br>AYTTPSGLALMAPSFAYLPVPSSTTRLIIQVPTVTPVGETLTLS<br>PTLSPLASVWSILPENVAVLLSSSPQQTVDFATLAYKVIDSHIV<br>HLFDHHSSAREIGRTFTPLTTIGKSGLTLQEAVKQAGYEPLEY<br>HGDPEAKTIVVLLNSSLALSLKAAVSVGTSGLGVVVVNVLRP<br>WDEAAIQTIIPSSATIVHVLDDVPNAVTQGSLYVDVFSALWST<br>TPKRSVHSHRITPSQTQKFIAAGGEFLRFVEEVTHIAVSEPSVA<br>SIKKTLFFSVPDSPLALLSRFVQELFLTKRTISSRHLTDYDVYS<br>KPGGISAQRLLISRDKSTDNVPVQAILPLDPNSVGHSDFLGVL<br>DHNLLKTHSLLKHAKKGSIVVVASPWTPDEFSANITYEVAEVI<br>TSRQLSVYTIDVKSIANDLELFIQEQKIEKGEAQVLLFEFVFLR<br>FYLGAAATEQAIIQLMSVLFDDIDLTKFSAAAWLGLKPVVVA<br>LPEVTPSDSPTLKEFEANAIAVETSEGQTVVNGARLSTWHDA<br>AKHLLFPSAFSPPTDPDSLSNPALRPEVPDTTFLVTCTVNKRLT<br>PLEYDRNVFHLEFDTSGTGLKYAIGEALGVHGWNDEQEVLDF<br>CEWYGVDPDRLITIPVIGSDDGKMHTRTVLQALQQQIDLFGRP<br>PKSFYTDLAEYATVDVDRYALRFIGSPEGVSTFKKMSEKDTV<br>SFGDVLKKYKSARPGIERLCELIGDIKPRHYSIASAQSVVGDR<br>VDLLVVTVDWLTPEGSPRYGQCTRYLAGLKIGQKVTVSIKPS<br>VMKLPPNLKQPLIMAGLGTGAAPFRAFLQHLAWLASKGEEIG<br>PVFYYFGSRYQAAEYLYGEEIEAFILGGVITRAGLAFSRDGPK<br>KVYIQHKMLEDSETLAKMLHDDDGVFYLCGPTWPVPDVYEA<br>LVNALVKYKGSDPVKAGEYLESLKEEERYVLEVY<br>(SEQ ID NO: 40) |
| 4-hydroxy-tryptamine kinase/ *P. cubensis* | P0DPA8 | MAFDLKTEDGLITYLTKHLSLDVDTSGVKRLSGGFVNVTWRI<br>KLNAPYQGHTSIILKHAQPHMSTDEDFKIGVERSVYEYQAIKL<br>MMANREVLGGVDGIVSVPEGLNYDLENNALIMQDVGKMKT<br>LLDYVTAKPPLATDIARLVGTEIGGFVARLHNIGRERRDDPEF<br>KFFSGNIVGRTTSDQLYQTIIPNAAKYGVDDPLLPTVVKDLVD<br>DVMHSEETLVMADLWSGNILLQLEEGNPSKLQKIYILDWELC<br>KYGPASLDLGYFLGDCYLISRFQDEQVGTTMRQAYLQSYART<br>SKHSINYAKVTAGIAAHIVMWTDFMQWGSEEERINFVKKGV<br>AAFHDARGNNDNGEITSTLLKESSTA<br>(SEQ ID NO: 41) |
| 4-hydroxy-tryptamine kinase/*P. cyanescens* | PPQ83229.1 | MAFDLKTPEGLLLYLTRHLSLDVDPSGVKRLSGGFVNVTWRI<br>RLNAPYQGHTSIILKHAQPHLSSDEDFKIGVERSAYEYQALKV<br>MSANQEVLGGDDSRVSVPEGLHYDVENNALIMQDVGTMKT<br>LLDYATAKPPLSTEIASLVGTEIGAFIARLHNLGRKRRDQPAF<br>KFFSGNIVGRTTADQLYQTIIPNAAKYGINDPLLPTVVKDLVG<br>EVMNSEETLIMADLWSGNILLEFVEGNPSELKKIWLVDWELC<br>KYGPASLDMGYFLGDCYLIARFQDELVGTTMRKAYLKGYAR<br>TAKGTINYSKVTASIGAHLVMWTDFMKWGNYEEREEFVKKG<br>VEALHDAWEDNNDGEITSVLVNEASST<br>(SEQ ID NO: 42) |
| 4-hydroxy-tryptamine kinase/*P. cyanescens* | PPQ98758.1 | MAFDLKTVEGLIVYLTKCLSLEVDSSGVKRLSGGFVNVTWRI<br>RLNAPYQGHTSIILKHAQPHMSTDKDFKIGVERSVYEYQALK<br>VISANREALGGIDSRVSAPEGLHYDVENNALIMQDVGTLKTL<br>MDYVIEKPAISTEMARLIGTEIGDFVARLHSIGRQKRDQPDFK<br>FFSGNIVGRTTADQLYQTILPNTAKYGIDDPLLPTVVKDLVDE |

TABLE 2-continued

Enzymes

| Enzyme/ Source Organism | genbank/ uniprot number | Sequence |
|---|---|---|
| | | AMQSEETLIMADLWTGNILVEFEEGNLSVLKKIWLVDWELCKYGPVRLDMGYFLGDCFLISRFKNEQVAKAMRQAFLQRYNRVSDTPINYSVATTGIAAHIVMWTDFMNWGTEEERKEYVKKGVAGIHDGRNHNVDGEITSILMQEASTA (SEQ ID NO: 43) |
| 4-hydroxy-tryptamine kinase/ *G. dilepis* | PPQ70874.1 | MTFDLKTEEGLLVYLTQHLSLDVDLDGLKRLSGGFVNITWRIRLNAPFKGYTNIILKHAQPHLSSDENFKIGVERSAYEYRALKIVSESPILSGDDNLVFVPQSLHYDVVHNALIVQDVGSLKTLMDYVTARPSLSSEMAKLVGGQIGAFIARLHNIGRENKDHPEFNFFSGNIVGRTTAVQLYETIVPNATKYDIDDPIIPVVVQELIEEVKGSDETLIMADLWGGNILLEFGKDSSDLGKIWVVDWELCKYGPPSLDMGYFLGDCFLLAQFQDEKVATAMRRAYLENYAKIAKVPMDYDRSTTGIGAHLVMWTDFMNWGSDEERKTSVEKGVRAFHDAKRDNKEGEIPSILLRESSRT (SEQ ID NO: 44) |
| Multicopper oxidase/*S. cerevisiae* | NP 116612.1 | MLFYSFVWSVLAASVALAKTHKLNYTASWVTANPDGLHEKRMIGFNGEWPLPDIHVEKGDRVELYLTNGFQDNTATSLHFHGLFQNTSLGNQLQMDGPSMVTQCPIVPGQTYLYNFTVPEQVGTFWYHAHMGAQYGDGMRGAFIIHDPEEPFEYDHERVITLSDHYHENYKTVTKEFLSRYNPTGAEPIPQNILFNNTMNVTLDFTPGETYLFRFLNVGLFVSQYIILEDHEMSIVEVDGVYVKPNFTDSIYLSAGQRMSVLIKAKDKMPTRNYAMMQIMDETMLDVVPPELQLNQTIQMRYGHSLPEARALNIEDCDLDRATNDFYLEPLIERDLLAHYDHQIVMDVRMVNLGDGVKYAFFNNITYVTPKVPTLTTLLTSGKLASDPRIYGDNINAQLLKHNDIIEVVLNNYDSGRHPFHLHGHNFQIVQKSPGFHVDEAYDESEQDEMTVPYNESAPLQPFPERPMVRDTVVLEPSGHVVLRFRADNPGVWYFHCHVDWHLQQGLASVFIEAPVLLQEREKLNENYLDICKAADIPVVGNAAGHSNDWFDLKGLPRQPEPLPKGFTTEGYLALIISTIIGVWGLYSIAQYGIGEVIPNDEKVYHTLREILAENEIEVSRG* (SEQ ID NO: 45) |
| aralkylamine N-acetyltransferase/*Bos taurus* | O02785 | MSTPSIHCLKPSPLHLPSGIPGSPGRQRRHTLPANEFRCLTPKDAAGVFEIEREAFISVSGNCPLNLDEVRHFLTLCPELSLGWFVEGRLVAFIIGSLWDEERLTQESLTLHRPGGRTAHLHALAVHHSFRQQGKGSVLLWRYLQHAGGQPAVRRAVLMCEDALVPFYQRFGFHPAGPCAVVVGSLTFTEMHCSLRGHAALRRNSDR (SEQ ID NO: 46) |
| Tryptamine 5-hydroxylase/ Schistoso-*mamansoni* | O96370 | MISTESDLRRQLDENVRSEADESTKEECPYINAVQSHHQNVQEMSIIISLVKNMNDMKSIISIFTDRNINILHIESRLGRLNMKKHTEKSEFEPLELLVHVEVPCIEVERLLEELKSFSSYRIVQNPLMNLPEAKNPTLDDKVPWFPRHISDLDKVSNSVLMYGKELDADHPGFKDKEYRKRRMMFADIALNYKWGQQIPIVEYTEIEKTTWGRIYRELTRLYKTSACHEFQKNLGLLQDKAGYNEFDLPQLQVVSDFLKARTGFCLRPVAGYLSARDFLSGLAFRVFYCTQYIRHQADPFYTPEPDCCHELLGHVPMLADPKFARFSQEIGLASLGTSDEEIKKLATCYFFTIEFGLCRQDNQLKAYGAGLLSSVAELQHALSDKAVIKPFIPMKVINEECLVTTFQNGYFETSSFEDATRQMREFVRTIKRPFDVHYNPYTQSIEIIKTPKSVAKLVQDLQFELTAINESLLKMNKEIRSQQFTTNKIVTENRSSGS* (SEQ ID NO: 47) |
| Acetylserotonin O-methyltransferase/*Homo sapiens* | P46597 | MGSSEDQAYRLLNDYANGFMVSQVLFAACELGVFDLLAEAPGPLDVAAVAAGVRASAHGTELLLDICVSLKLLKVETRGGKAFYRNTELSSDYLTTVSPTSQCSMLKYMGRTSYRCWGHLADAVREGRNQYLETFGVPAEELFTAIYRSEGERLQFMQALQEVWSVNGRSVLTAFDLSVFPLMCDLGGGAGALAKECMSLYPGCKITVFDIPEVVWTAKQHFSFQEEEQIDFQEGDFFKDPLPEADLYILARVLHDWADGKCSHLLERIYHTCKPGGGILVIESLLDEDRRGPLLTQLYSLNMLVQTEGQERTPTHYHMLLSSAGFRDFQFKKTGAIYDAILARK (SEQ ID NO: 48) |
| Noribogaine 10-O-methyltransferase/ *Tabernantheiboga* | A0A2Z5P0W7 | DAMKSAELFKAQAHIFKQVFCFTNGASLKCAVQLGIPDAIDNHGKAMTLSELTDALPINPSKAPHIHRLMRILVTAGFFVEERLGNGKEEKANGYALTPSSRLLLKNKPLSLRASALTMLDPVTVKTWNALSEWFQNEDQTAFETAHGKNMWDFFAEDPGLSKKFNESMASDSQLVTEVLVTKCKFVFEGLTSMVDVGGGTGTVAGAIAKTFPSLRCTVFDLPHVVANLEPTENLDFVAGDMFGKIPPANAIFLKWVLHDWNDEDCVKILKNCKRAIPGKEKGGKVIIVDIIMETEKHDIDEFDYAKMCMDMEMLVLCNSKERTEKELAMLVSEAGFSGYKIFPVLGIRSLIEVYP (SEQ ID NO: 49) |

EXAMPLES

These examples are provided for illustrative purposes only and not to limit the scope of the claims provided herein.

Example 1: Detection of 4-hydroxytryptamine in Engineered Cells

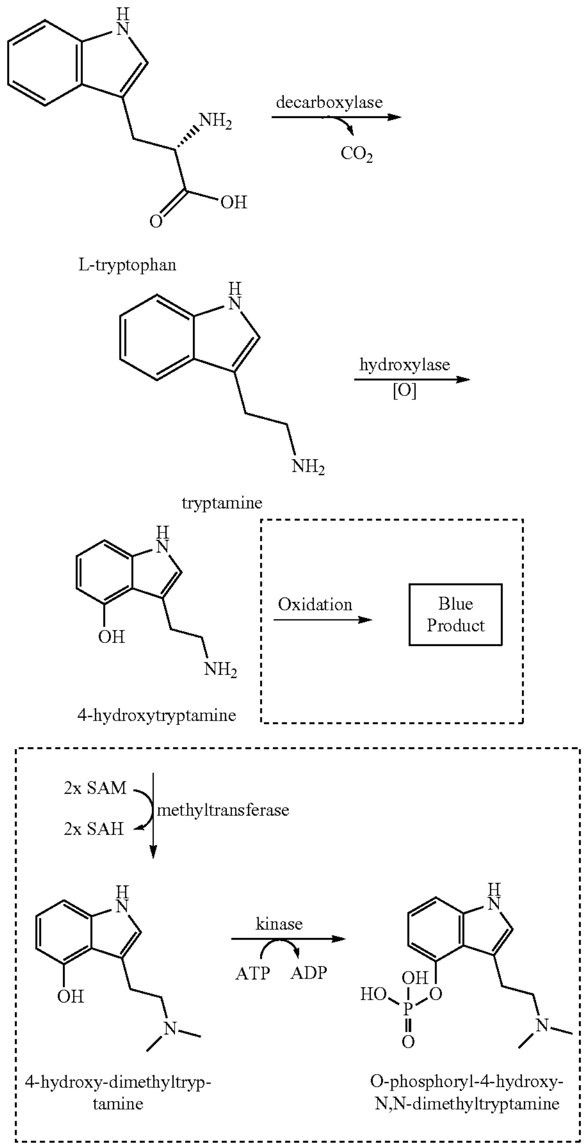

L-tryptophan tryptamine 4-hydroxytryptamine 4-hydroxy-dimethyltryptamine

O-phosphoryl-4-hydroxy-N,N-dimethyltryptamine 4-hydroxytryptamine can be oxidized to a blue product to screen for high biosynthetic flux through the upstream pathway (blue box). Alternatively, 4-hydroxytryptamine can be employed for conversion to O-phosphoryl-4-hydroxy-N,N-dimethyltryptamine, or psilocybin, by expression of the methyltransferase or kinase.

Example 2. Yeast and Bacterial Strains and Growth Conditions

Single gene expression plasmids were transformed into chemically competent TG1 *E. coli* and multigene plasmids were transformed into TransforMax™ EPI300™ (Epicentre) electrocompetent *E. coli*. Strains were constructed using chemical or electro-competency. Selections were performed on LB containing ampicillin (25 mg/L) and kanamycin (25 mg/L) as indicated. The background strain MG1655 with lambda DE3 (a phage construct that expresses T7 RNA polymerase under the control of a lacUV5 promoter) was used as a host strain and propagated at 37° C. *S. cerevisiae* strain BY4741 (MATa his3Δ1 leu2Δ0 met15Δ0 ura3Δ0) was used for experiments in this study and propagated at 30° C.

*E. coli* cultures were propagated in LB broth (1-liter medium contained 10 grams of tryptone, 5 grams of yeast extract, and 10 grams of sodium chloride). Yeast cultures were grown in YPD (10 g/L Bacto Yeast Extract; 20 g/L Bacto Peptone; 20 g/L D-glucose). Lithium acetate transformation method was used to transform yeast with plasmids containing the respective auxotrophic markers. Selection was performed on synthetic dropout media (6.7 g/L Difco yeast nitrogen base without amino acids; 2 g/L synthetic defined amino acid mix minus the respective autotrophy, without yeast nitrogen base (US Biological); 20 g/L D-glucose or the respective carbon source; 20 g/L BD Difco agar was used for plates). pH was adjusted when appropriate with NaOH or HCl.

Plasmids and Cloning

A hierarchical Golden Gate cloning scheme was used for assembling coding sequence part plasmids, yeast protein expression cassettes and multigene plasmids. All protein coding sequences were synthesized or PCR amplified to omit internal BsaI and BsmBI sites for use in golden gate cloning. The protein coding sequences for fungal pathway enzymes were codon optimized for *E. coli* or *S. cerevisiae* and synthesized by Integrated DNA Technologies (Coralville, IA).

Example 3. Production of Substituted Tryptamines by Fed Substituted Indoles and Anthranilates The background strain MG1655 with lambda DE3 is a phage construct that expresses T7 RNA polymerase under the control of a lacUV5 promoter and was used as a host strain. The strain was modified to have the tryptophan biosynthetic pathway (e.g., trpE, trpD, trpC, trpB, and trpA) and tryptophan deaminase (tnaA) knocked out. This genetic material was removed by modified λ red system as described by Datsenko and Wanner (2000). The resulting strain was named bNAB001.

Figure 2:
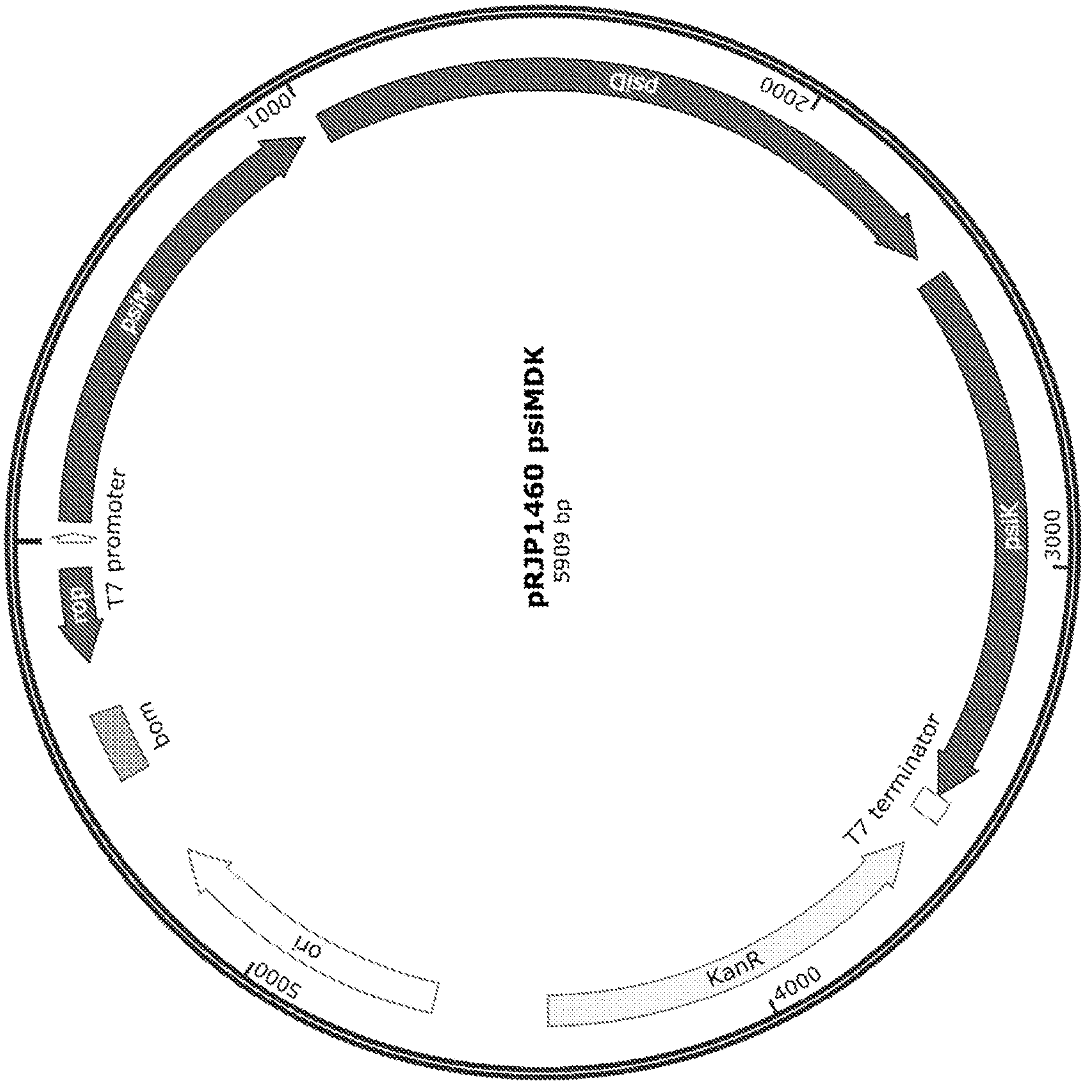
FIG. 2 depicts a non-limiting example of a plasmid map suitable for overexpression of psilocybin synthase (e.g., SEQ ID NO: 21), tryptophan decarboxylase (e.g., SEQ ID NO: 14) and 4-hydroxytryptamine kinase (e.g., SEQ ID NO: 41) in bacteria in accordance with embodiments of the disclosure.
Figure 3:
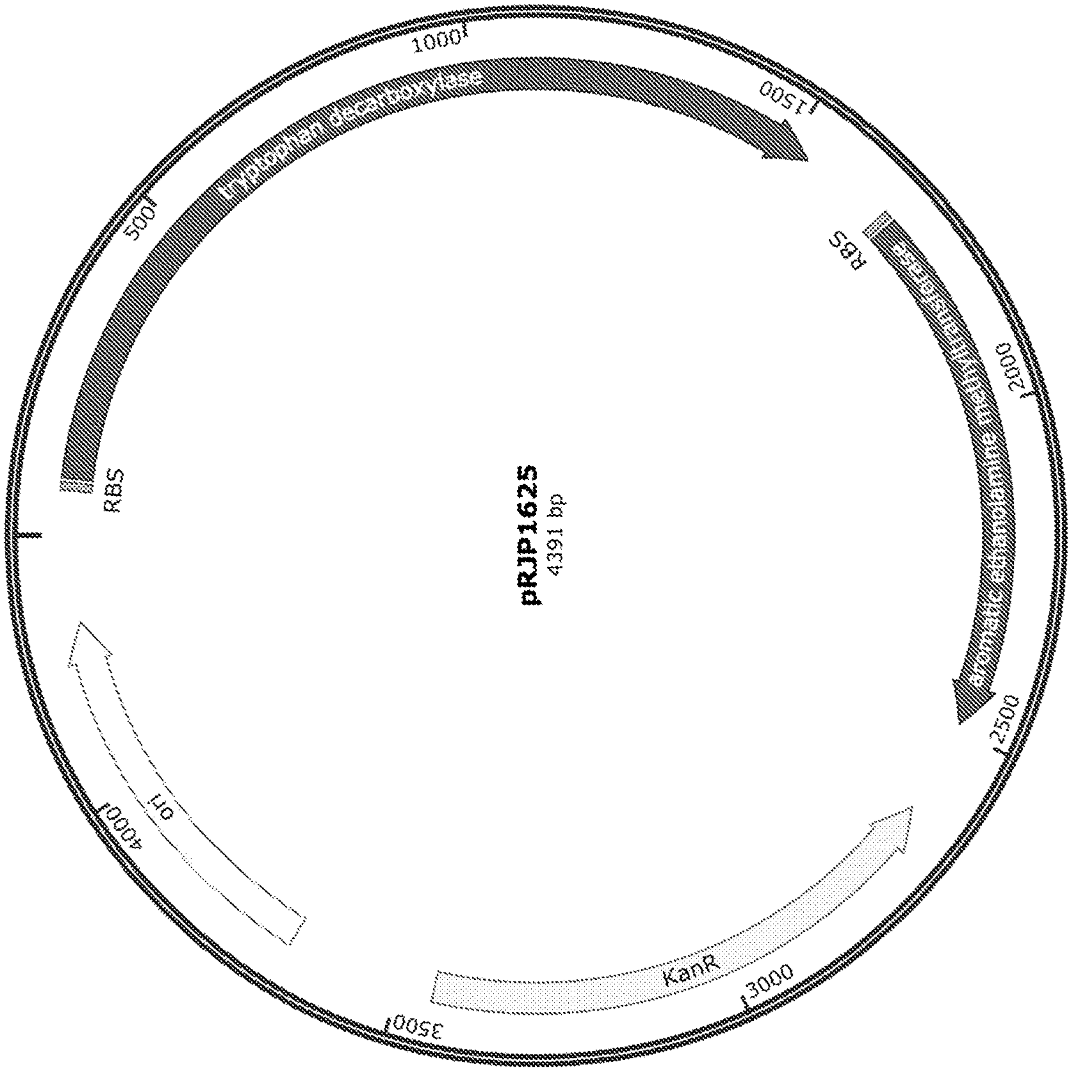
FIG. 3 depicts a non-limiting example of a plasmid map suitable for the production of N-methyl derivatives in bacteria by overexpression of tryptophan decarboxylase (e.g., SEQ ID NO: 19) and ethanolamine methyltransferase (e.g., SEQ ID NO: 25) in accordance with embodiments of the disclosure.

The tryptophan biosynthetic pathway, trpDCBA (SEQ ID NO: 1), was cloned under Lad operon control in an ampicillin resistance plasmid with p15a origin and was named pRJP1376 (FIG. 1). This plasmid was introduced into bNAB001 and resulted in strain bNAB002. Accordingly, the bNAB002 strain, upon isopropyl β-D-1-thiogalactopyranoside (IPTG) induction, allows for expression of trpDCBA operon for substituted tryptophan biosynthesis upon addition of substituted anthranilate and substituted indole addition. To further convert resulting substituted tryptophan compounds into downstream tryptamines, two plasmids were cloned. Coding sequences for tryptophan decarboxylase from *P. cubensis* (psiD, SEQ ID NO: 14) for converting substituted tryptophans to tryptamines; 4-hydroxytryptamine kinase from *P. cubensis* (psiK, SEQ ID NO: 41); and tryptamine N-methyltransferase from *P. cubensis* (psiM, SEQ ID NO: 21) were cloned into a plasmid containing a kanamycin resistance gene and BR322 origin of replication and was named pRJP1460 (FIG. 2). Coding sequences were oriented in a multi-cistronic operon downstream of a T7 promoter sequence. This plasmid was transformed into bNAB002 and the resulting strain was named bNAB003. Coding sequences for tryptophan decarboxylase from *B. atrophaeus* (SEQ ID NO: 19) and aromatic ethanolamine methyltransferase from *H. sapiens* (SEQ ID NO: 25) were cloned downstream of promoter and ribosome binding sequences with a kanamycin resistance gene and BR322 origin of replication sequences to form plasmid pRJP1625 (FIG. 3). The pRJP1625 plasmid was transformed into bNAB002 and the resulting strain was named bNAB004.

An overnight bNAB003 culture was used to inoculate 1 L of LB (plus kanamycin and ampicillin) culture at 0.1 $OD_{600}$. The culture was grown to $OD_{600}$ of 0.5 and cooled to 18° C. on ice before induction with 0.5 mM of IPTG for expression of trpDCBA pathway proteins and psiMDK pathway proteins. The culture was transferred to a shaker at 18° C. with 200 RPM shaking for 16 hours. The cells were harvested, washed with sterile water, and resuspended in M9 media (0.2% glucose, 40 mM $Na_2HPO_4$, 20 mM $KH_2PO_4$, 1 mM $MgSO_4$, 0.1 mM $CaCl_2$, 0.5 mM IPTG, with added 100 mg/L of L-serine, 2 g/L sodium citrate, and 2 g/L yeast extract). The culture was split into 10 mL cultures in sterile culture tubes. 4 mM of 5-hydroxyindole, 4-hydroxyindole, 7-hydroxyindole, and 4-chloroindole were added to separate tubes. After 3 days of incubation at 30° C., media from cultures were sampled by centrifuging 1 mL of culture at 18000 rpm and transferring clarified media to sample vials. Analysis was performed by chromatography/mass spectrometry (LCMS) with a 1260 Infinity LC System connected to a 6120 Quadrupole Mass Spectrometer (Agilent Technologies). Zorbax Eclipse Plus C18 guard column (4.6 cm×12.5 cm, 5 μm packing, Agilent Technologies) was connected to a Zorbax Eclipse Plus C18 column (4.6 mm×100 mm, 3.5 μm packing, Agilent Technologies) at 20° C. using a 0.5 mL/min. flow rate. Water and acetonitrile mobile phases contained 0.1% formic acid as the pH modifier. The elution gradient (water:acetonitrile volume ratio) was as follows: 98:2 (0-2 min), linear ramp from 98:2 to 5:95 (2-17 min), 5:95 (17-22 min), linear ramp from 5:95 to 98:2 (22-23 min), and 98:2 (23-28 min). Absorbance was measured using a diode array detector for UV-Vis analysis. MS was conducted in atmospheric pressure ionization-positive electrospray (API-ES positive) mode at 100-V fragmentor voltage with ion detection set to both full scanning mode (50-1200 m/z). Detection of tryptamines was conducted by extraction of ion masses of corresponding tryptamine not found in the unfed control sample. In the 5-hydroxyindole fed culture, 5-hydroxytryptamine was detected. In the 4-hydroxyindole culture, 4-hydroxytryptamine, 4-phosphoryloxytryptamine, and 4-phosphoryloxy-N,N-dimethyltryptamine were detected. In the 7-hydroxyindole fed culture, 7-hydroxytryptamine, 7-phosphoryloxytryptamine, and 7-phosphoryloxy-N,N-dimethyltryptamine were detected. In the 4-chloroindole fed culture, 4-chloro-N,N-dimethyltryptamine was detected (see FIG. 4).

An overnight bNAB004 culture was used to inoculate 1 L of LB (plus kanamycin and ampicillin) culture at 0.1 $OD_{600}$. The culture was grown to $OD_{600}$ of 0.5 and cooled to 18° C. on ice before induction with 0.5 mM of IPTG for expression of trpDCBA pathway proteins and psiMDK pathway proteins. The culture was transferred to a shaker at 18° C. with 200 RPM shaking for 16 hours. The cells were harvested, washed with sterile water, and resuspended in M9 media (0.2% glucose, 40 mM $Na_2HPO_4$, 20 mM $KH_2PO_4$, 1 mM $MgSO_4$, 0.1 mM $CaCl_2$, 0.5 mM IPTG, with added 100 mg/L of L-serine, 2 g/L sodium citrate, and 2 g/L yeast extract). The culture was split into 10 mL cultures in sterile culture tubes. 4 mM of 5-hydroxyindole, 4-chloroindole, and 5-bromoanthranilate were added to separate tubes. After 3 days of incubation at 30° C., media from cultures were sampled by centrifuging 1 mL of culture at 18000 rpm and transferring clarified media to sample vials. Analysis was performed by chromatography/mass spectrometry (LCMS) with a 1260 Infinity LC System connected to a 6120 Quadrupole Mass Spectrometer (Agilent Technologies). Zorbax Eclipse Plus C18 guard column (4.6 cm×12.5 cm, 5 μm packing, Agilent Technologies) was connected to a Zorbax Eclipse Plus C18 column (4.6 mm×100 mm, 3.5 μm packing, Agilent Technologies) at 20° C. using a 0.5 mL/min flow rate. Water and acetonitrile mobile phases contained 0.1% formic acid as the pH modifier. The elution gradient (water:acetonitrile volume ratio) was as follows: 98:2 (0-2 min), linear ramp from 98:2 to 5:95 (2-17 min), 5:95 (17-22 min), linear ramp from 5:95 to 98:2 (22-23 min), and 98:2 (23-28 min). Absorbance was measured using a diode array detector for UV-Vis analysis. MS was conducted in atmospheric pressure ionization-positive electrospray (API-ES positive) mode at 100-V fragmentor voltage with ion detection set to both full scanning mode (50-1200 m/z). Detection of tryptamines was conducted by extraction of ion masses of corresponding tryptamine not found in the unfed control sample. In the 5-hydroxyindole fed culture, 5-hydroxytryptamine, 5-hydroxymethyltryptamine, and 5-hydroxy-N,N-dimethyltryptamine were detected. In the 4-chloroindole fed culture, 4-chlorotryptamine and 4-chloro-N,N-dimethyltryptamine were detected. In the 5-bromoanthranilate fed culture, 5-bromotryptamine, 5-bromo-N-methyltryptamine, and 5-bromo-N,N-dimethyltryptamine were detected (see FIG. 4).

Example 4. Production of Substituted Tryptamines by Engineered Yeast

Figure 5:
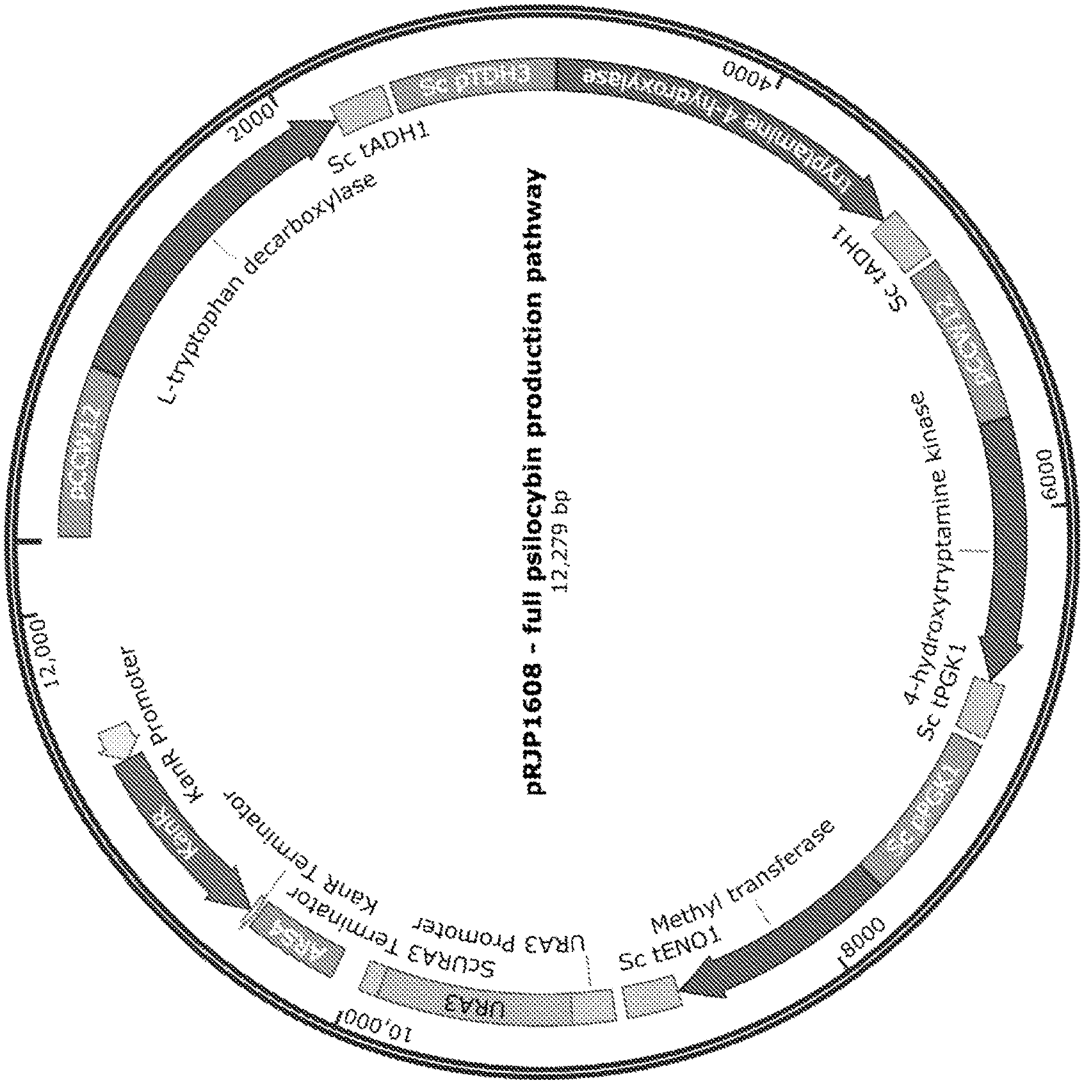
FIG. 5 depicts a non-limiting example of a plasmid map suitable for the production of N-methyl tryptamine derivatives in yeast by overexpression of tryptophan decarboxylase (e.g., SEQ ID NO: 19), 4-hydroxytryptamine kinase (e.g., SEQ ID NO: 41), psilocybin synthase (e.g., SEQ ID NO: 21) and tryptamine 4-hydroxylase (e.g., SEQ ID NO: 33) in accordance with embodiments of the disclosure.
Figure 6:
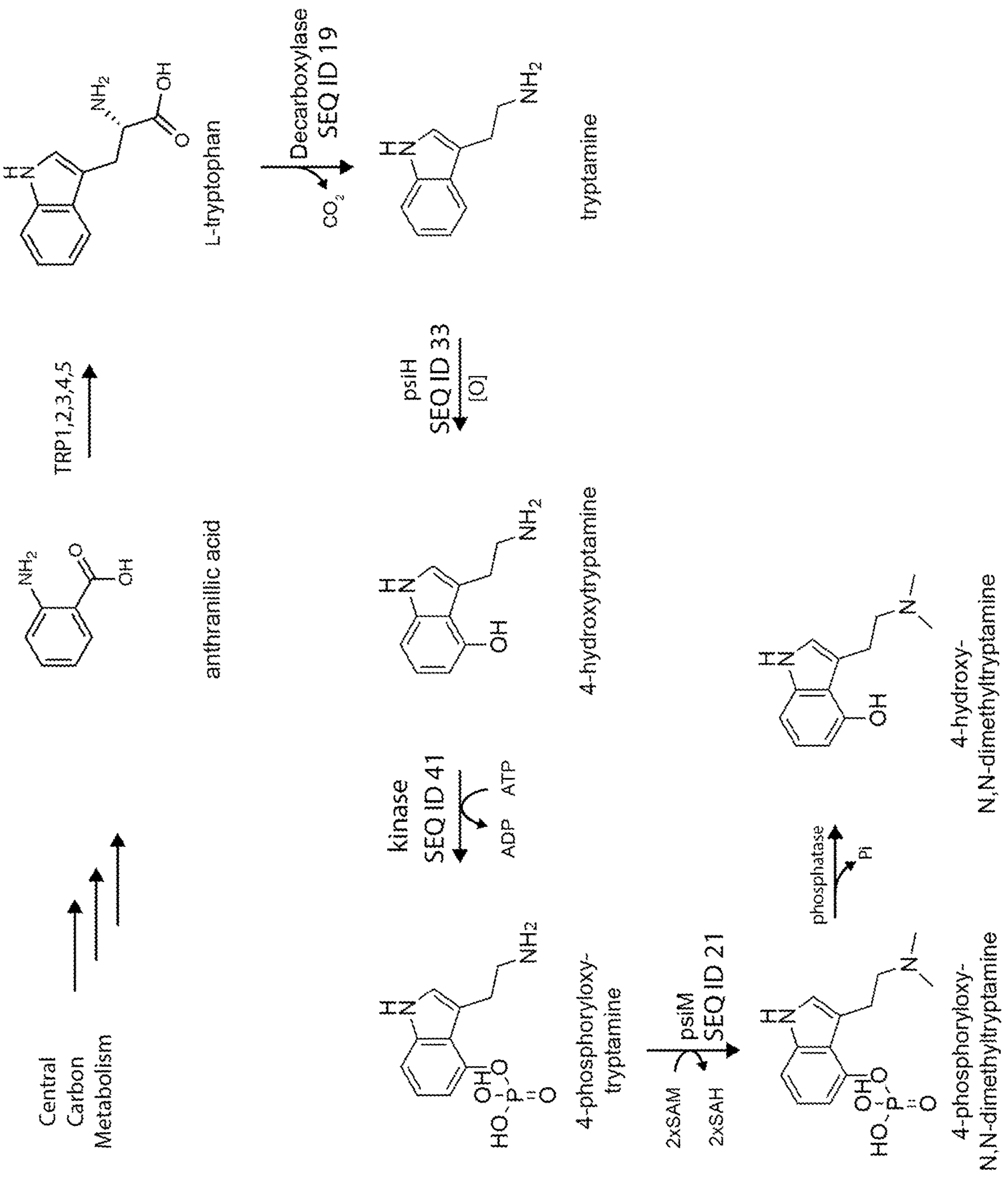
FIG. 6 depicts a non-limiting example of a biosynthetic pathway converting anthranilic acid present in yeast metabolism to tryptamines by enzymes encoded in pRJP1608 in accordance with embodiments of the disclosure.
Figure 7:
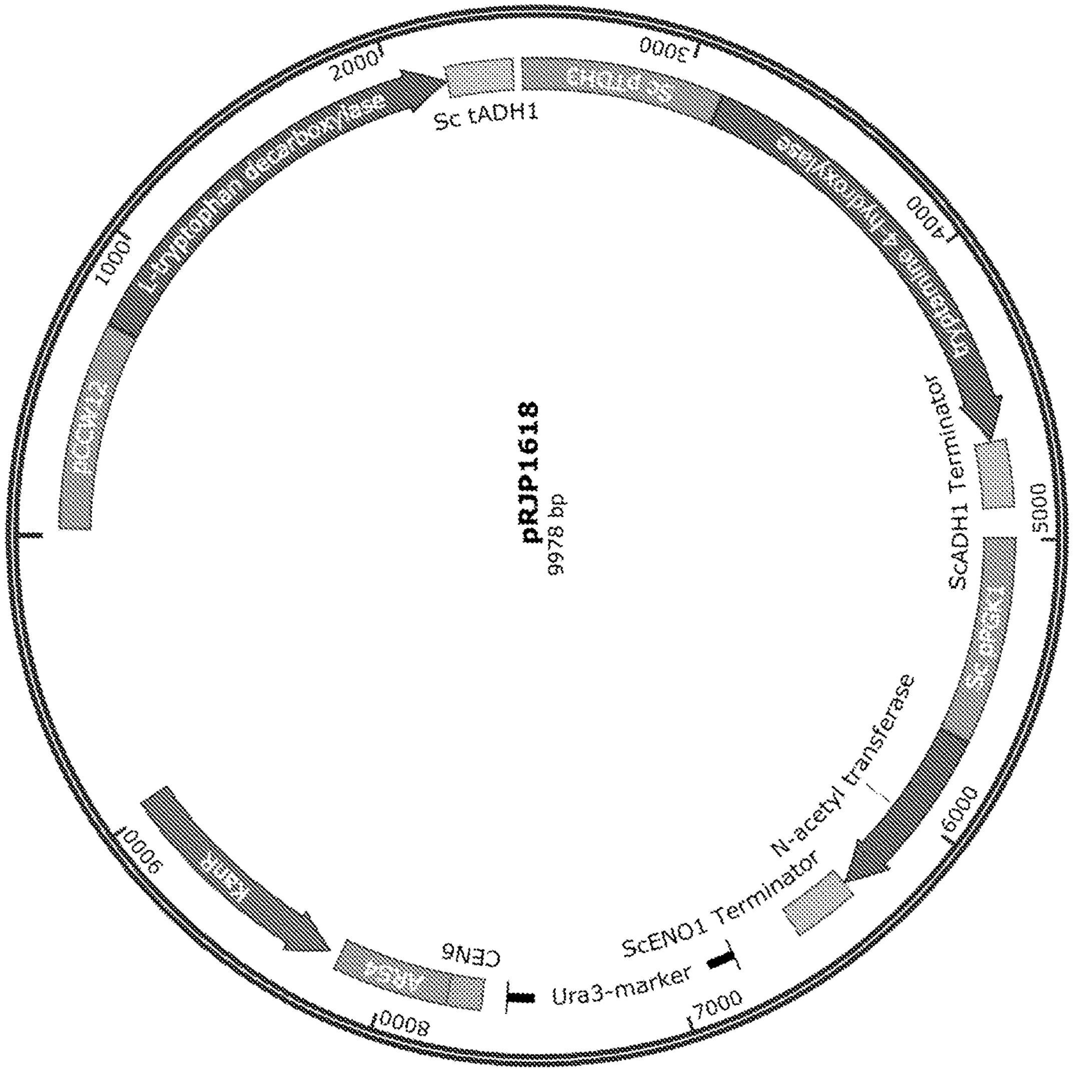
FIG. 7 depicts a non-limiting example of a plasmid map for the production of N-acetyl tryptamine derivatives in yeast by overexpression of tryptophan decarboxylase (e.g., SEQ ID NO: 19), tryptamine 4-hydroxylase (e.g., SEQ ID NO: 33) and N-acetyltransferase (e.g., SEQ ID NO: 28) in accordance with embodiments of the disclosure.

Anthranilate biosynthetically produced from central carbon metabolism (i.e., hydrogen substituted anthranilate) can be metabolized to form substituted tryptamines with genetic modification. Substitutions of the amine position of tryptamine and indole ring were investigated. A multigene plasmid with CEN6/ARS4 replication sequences, URA3 expression cassette and kanamycin resistance was cloned to contain coding sequences for tryptophan decarboxylase from *B. atrophaeus* (SEQ ID NO: 19), tryptophan 4-hydroxylase from *P. cyanescens* (SEQ ID NO: 33), 4-hydroxytryptamine kinase from *P. cubensis* (psiK, SEQ ID NO: 41), and tryptamine N-methyltransferase from *P. cubensis* (psiM, SEQ ID NO: 21) under control of high activity yeast promoter and terminator pairs (e.g., promoters pCCW12, pTDH3, and pPGK1, or terminators tADH1, tPGK1, and tENO1) and was named plasmid pRJP1608 (FIG. 5). The biosynthetic pathway converting anthranilic acid present in the yeast metabolism to tryptamines by enzymes encoded in pRJP1608 is outlined in FIG. 6. A second multigene plasmid with CEN6/ARS4 replication sequences, URA3 expression cassette, and kanamycin resistance was cloned to contain coding sequences for tryptophan decarboxylase from *B. atrophaeus* (SEQ ID NO: 19), tryptophan 4-hydroxylase from *P. cyanescens* (SEQ ID NO: 33), and aralkylamine N-acetyltransferase from *B. taurus* (SEQ ID NO: 46) under control of high activity yeast promoter and terminator pairs (e.g., promoters pCCW12, pTDH3, and pPGK1, or terminators tADH1, tPGK1, and tENO1) and was named plasmid pRJP1618 (FIG. 7). The biosynthetic pathway converting anthranilic acid present in the yeast metabolism to tryptamines by enzymes encoded in pRJP1618 is outlined in FIG. 8.

*S. cerevisiae* strain BY4741 (MATa his3Δ1 leu2Δ0 met15Δ0 ura3Δ0) was used for experiments in this study and propagated at 30° C. The pRJP1608 plasmid was transformed into BY4741 by lithium acetate protocol and selected for on synthetic complete medium lacking uracil. The resulting strain, yNAB001, was isolated and genotyped. The pRJP1618 plasmid was transformed into BY4741 by lithium acetate protocol and selected for on synthetic complete medium lacking uracil. The resulting strain, yNAB002, was isolated and genotyped.

Colonies of yNAB001 and yNAB002 were used to inoculate 5 mL cultures of synthetic complete medium and were grown at 30° C. in a rotary shaker at 225 rpm. Media from cultures were sampled by centrifuging 1 mL of culture at 18000 rpm and transferring clarified media to sample vials. Analysis was performed by chromatography/mass spectrometry (LCMS) with a 1260 Infinity LC System connected to a 6120 Quadrupole Mass Spectrometer (Agilent Technologies). Zorbax Eclipse Plus C18 guard column (4.6 cm×12.5 cm, 5 μm packing, Agilent Technologies) was connected to a Zorbax Eclipse Plus C18 column (4.6 mm×100 mm, 3.5 μm packing, Agilent Technologies) at 20° C. using a 0.5 mL/min. flow rate. Water and acetonitrile mobile phases contained 0.1% formic acid as the pH modifier. The elution gradient (water:acetonitrile volume ratio) was as follows: 98:2 (0-2 min), linear ramp from 98:2 to 5:95 (2-17 min), 5:95 (17-22 min), linear ramp from 5:95 to 98:2 (22-23 min), and 98:2 (23-28 min). Absorbance was measured using a diode array detector for UV-Vis analysis. MS was conducted in atmospheric pressure ionization-positive electrospray (API-ES positive) mode at 100-V fragmentor voltage with ion detection set to both full scanning mode (50-1200 m/z).

Figure 8:
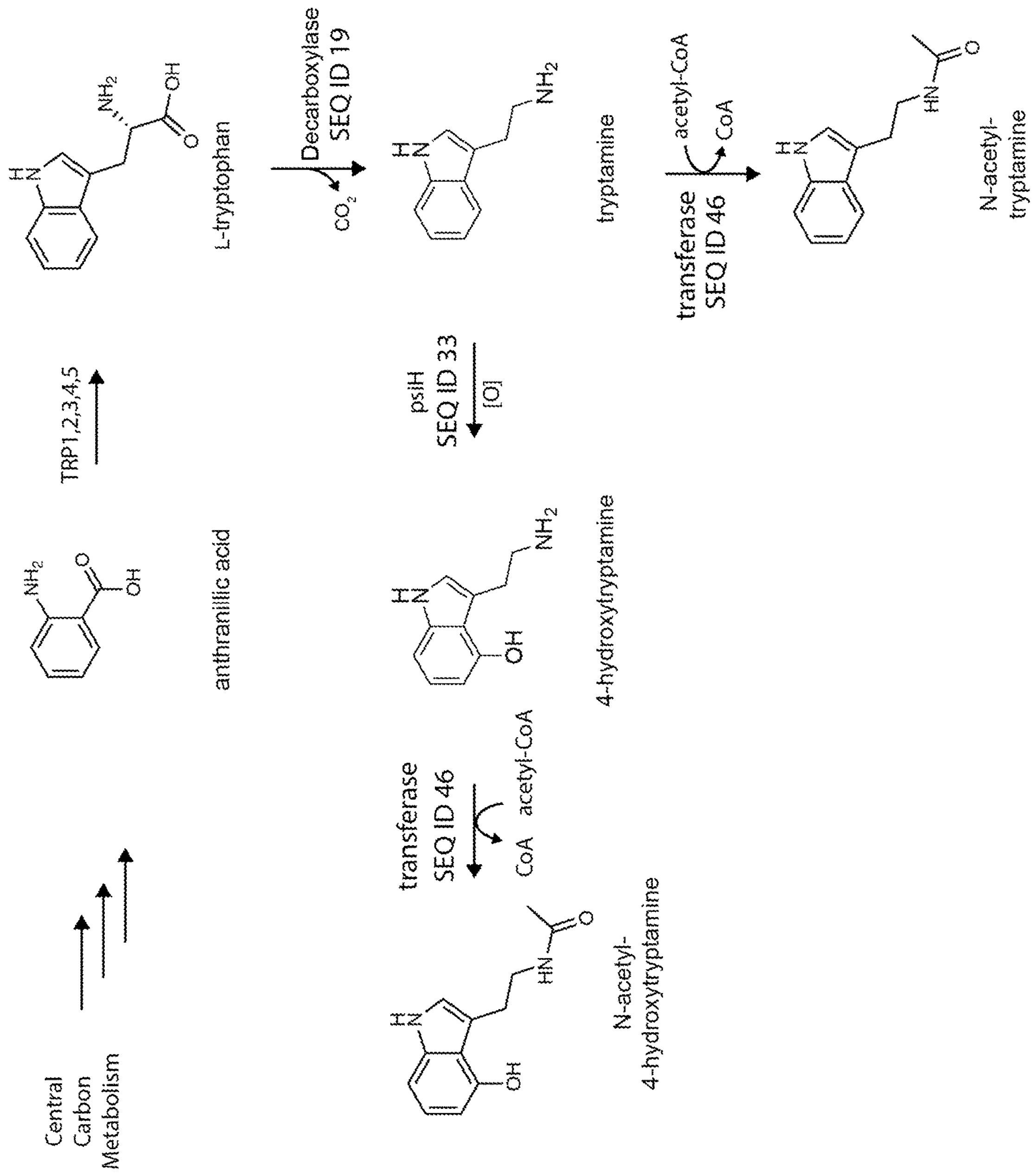
FIG. 8 depicts a non-limiting example of a biosynthetic pathway converting anthranilic acid present in yeast metabolism to tryptamines by enzymes encoded in pRJP1618 is accordance with embodiments of the disclosure.
Figure 9:
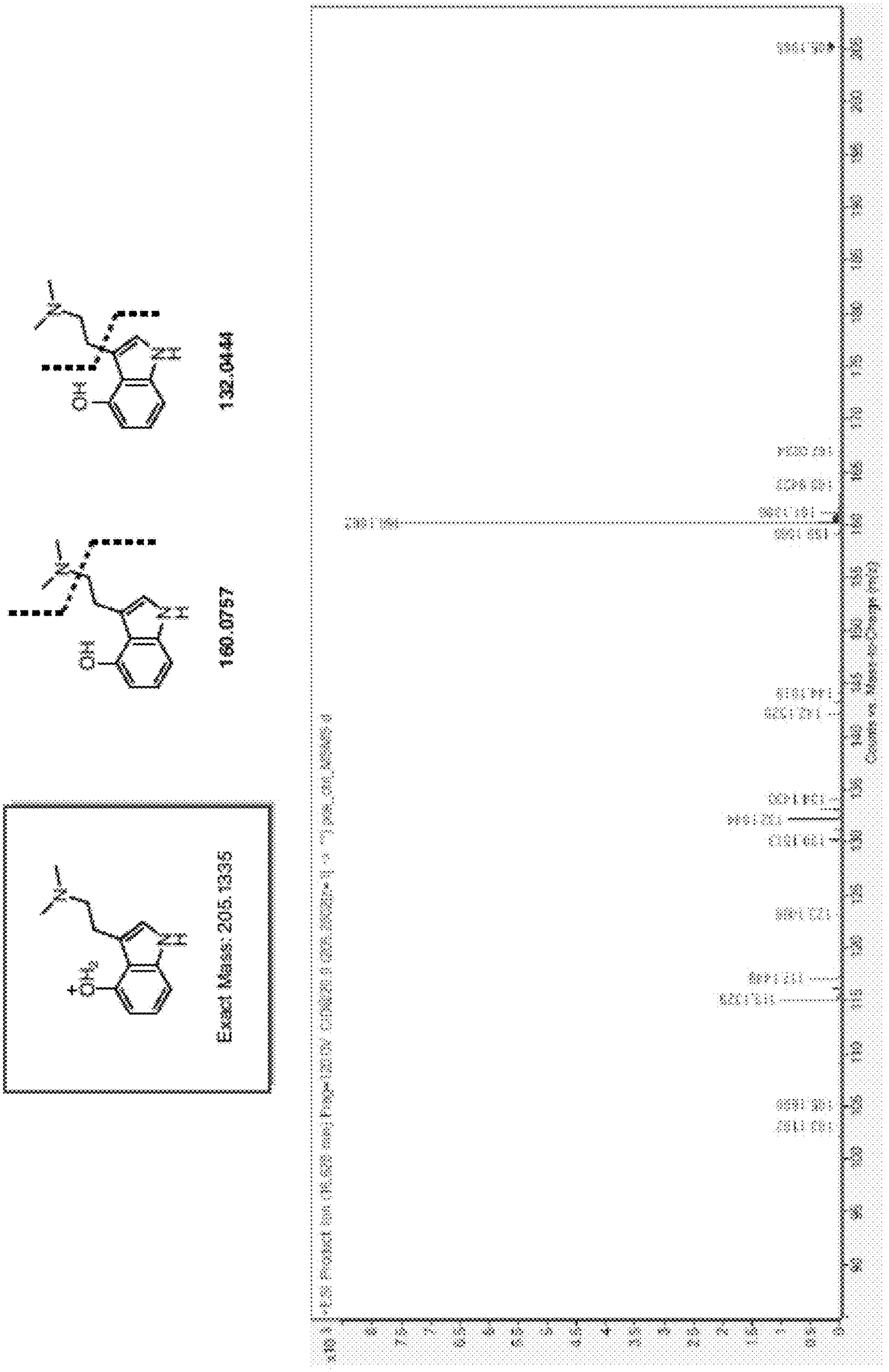
FIG. 9 depicts a non-limiting example of tandem mass spectrometry (MS/MS) of 4-hydroxy-N,N-dimethyl-tryptamine derived from engineered yeast cells in accordance with embodiments of the disclosure.
Figure 10:
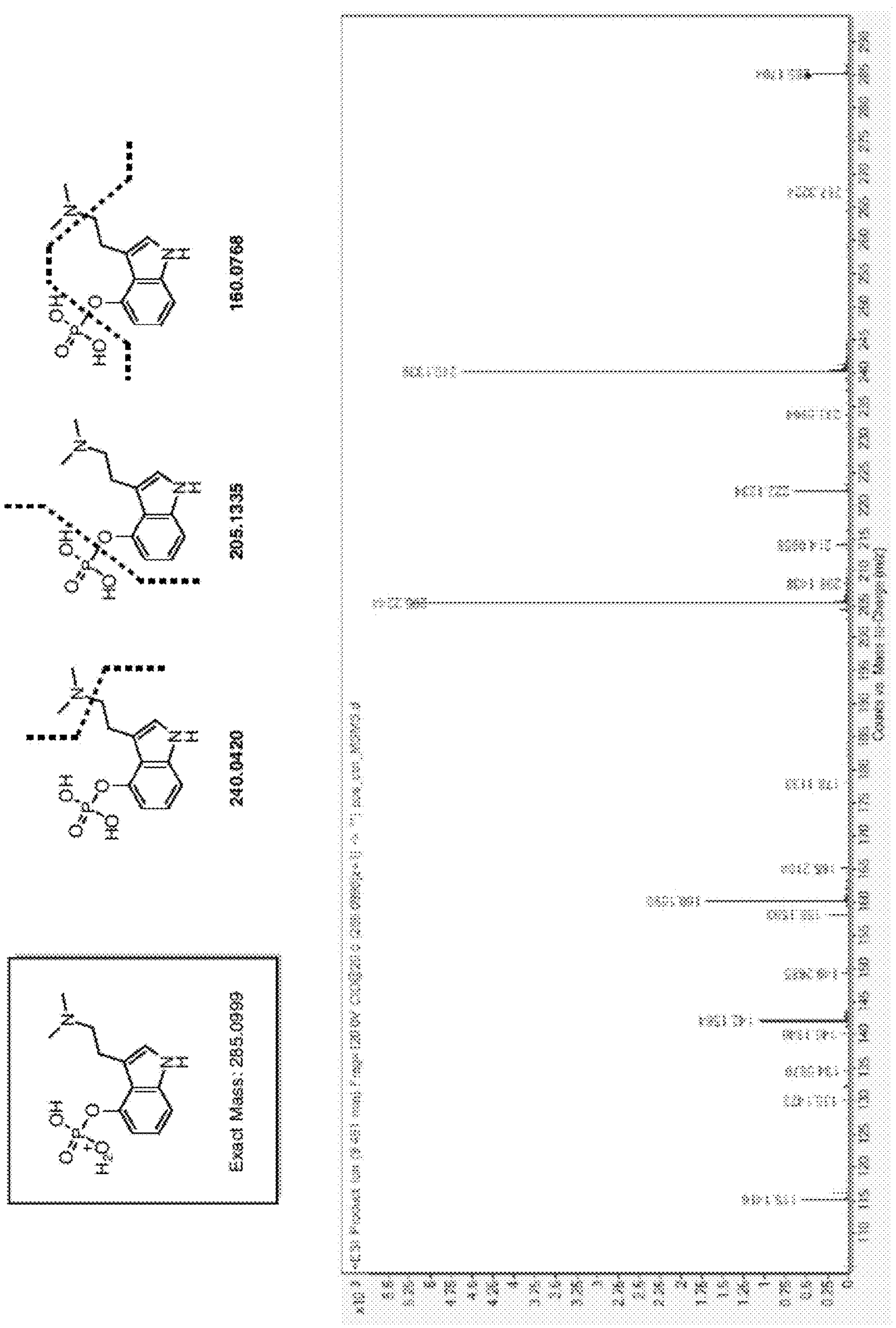
FIG. 10 depicts a non-limiting example of tandem mass spectrometry (MS/MS) of psilocybin derived from engineered yeast cells in accordance with embodiments of the disclosure.
Figure 12:
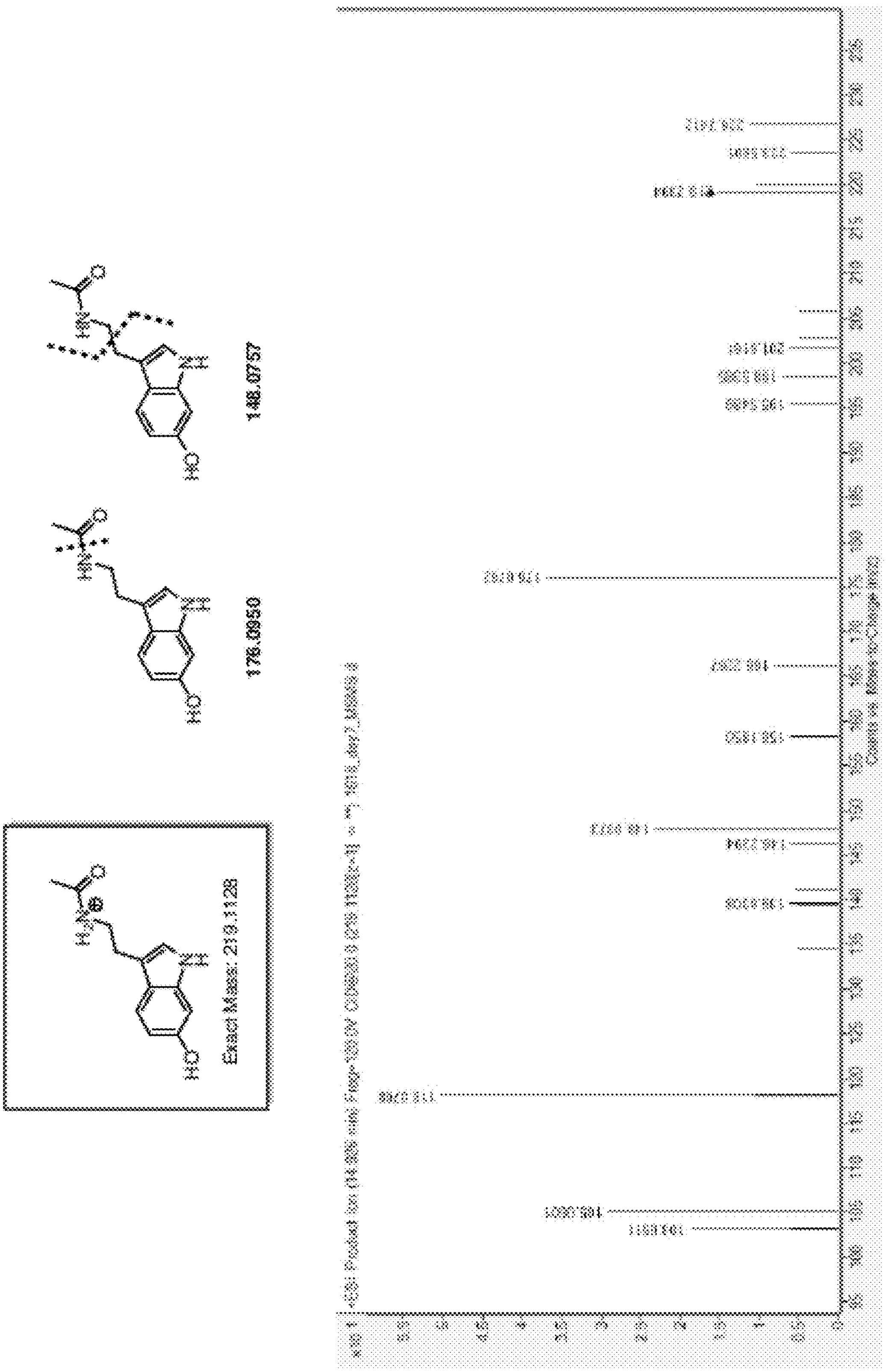
FIG. 12 depicts a non-limiting example of tandem mass spectrometry (MS/MS) of 4-hydroxy-N-acetyltryptamine derived from engineered yeast cells in accordance with embodiments of the disclosure.

Detection of tryptamines was conducted by extraction of ion masses of corresponding tryptamine not found in the unfed control sample. Additionally, tandem MS/MS was conducted. In the culture of yNAB001, ion masses for tryptamine, 4-hydroxytryptamine, 4-phosphoryloxytryptamine, 4-hydroxy-N,N-dimethyltryptamine, and 4-phosphoryloxy-N,N-dimethyltryptamine were detected (FIG. 6). Tandem MS/MS fragmentation data was collected for 4-hydroxy-N,N-dimethyltryptamine at a positive ion mass of 205.1335 m/z (FIG. 9) and 4-phosphoryloxy-N,N-dimethyltryptamine at a positive ion mass of 285.0999 m/z (FIG. 10). In the culture of yNAB002, ion masses for tryptamine, 4-hydroxytryptamine, N-acetyl-tryptamine, and 4-hydroxy-N-acetyl-tryptamine were detected (FIG. 8). Tandem MS/MS fragmentation data was collected for N-acetyl-tryptamine at a positive ion mass of 203.1179 m/z (FIG. 11) and 4-hydroxy-N-acetyl-tryptamine at a positive ion mass of 219.1128 (FIG. 12). Media from an untransformed strain of BY4741 detected only trace levels of tryptamine and no other aforementioned tryptamines from yNAB001 and yNAB002 media.

Figure 13:
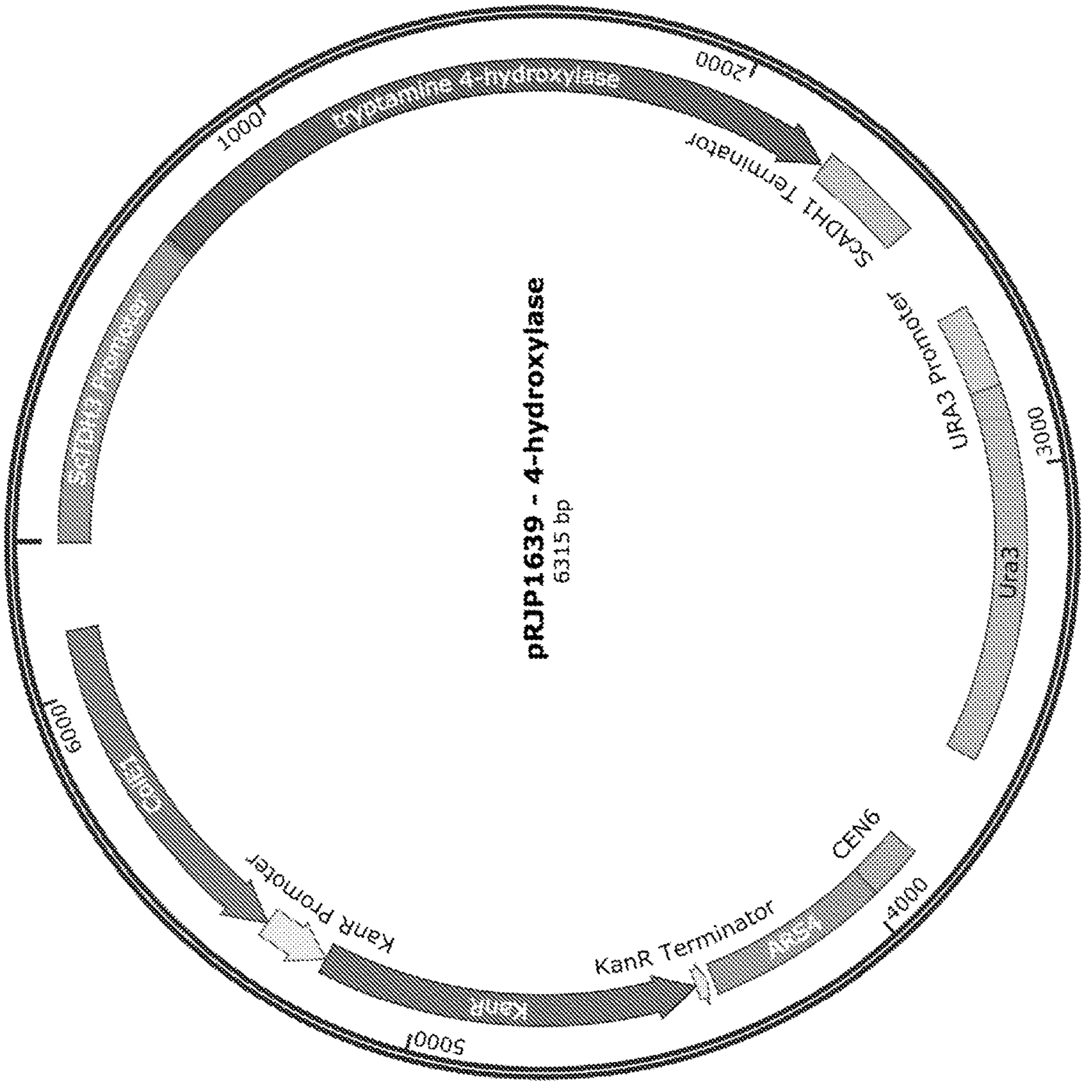
FIG. 13 depicts a non-limiting example of a plasmid map for the overexpression tryptamine 4-hydroxylase (e.g., SEQ ID NO: 33) in yeast in accordance with embodiments of the disclosure.
Figure 14:
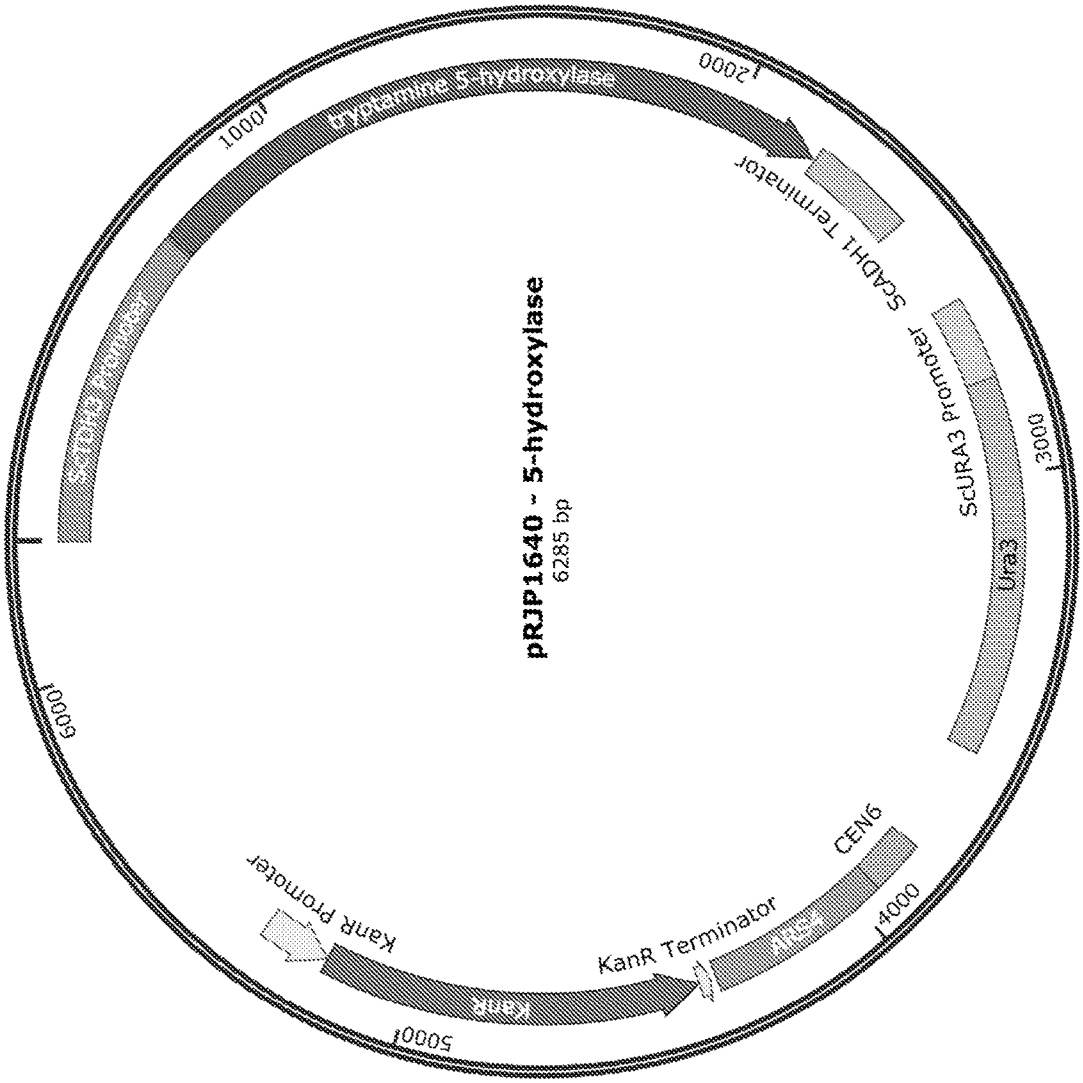
FIG. 14 depicts a non-limiting example of a plasmid map for the overexpression of tryptamine 5-hydroxylase (e.g., SEQ ID NO: 47) in yeast in accordance with embodiments of the disclosure.
Figure 15:
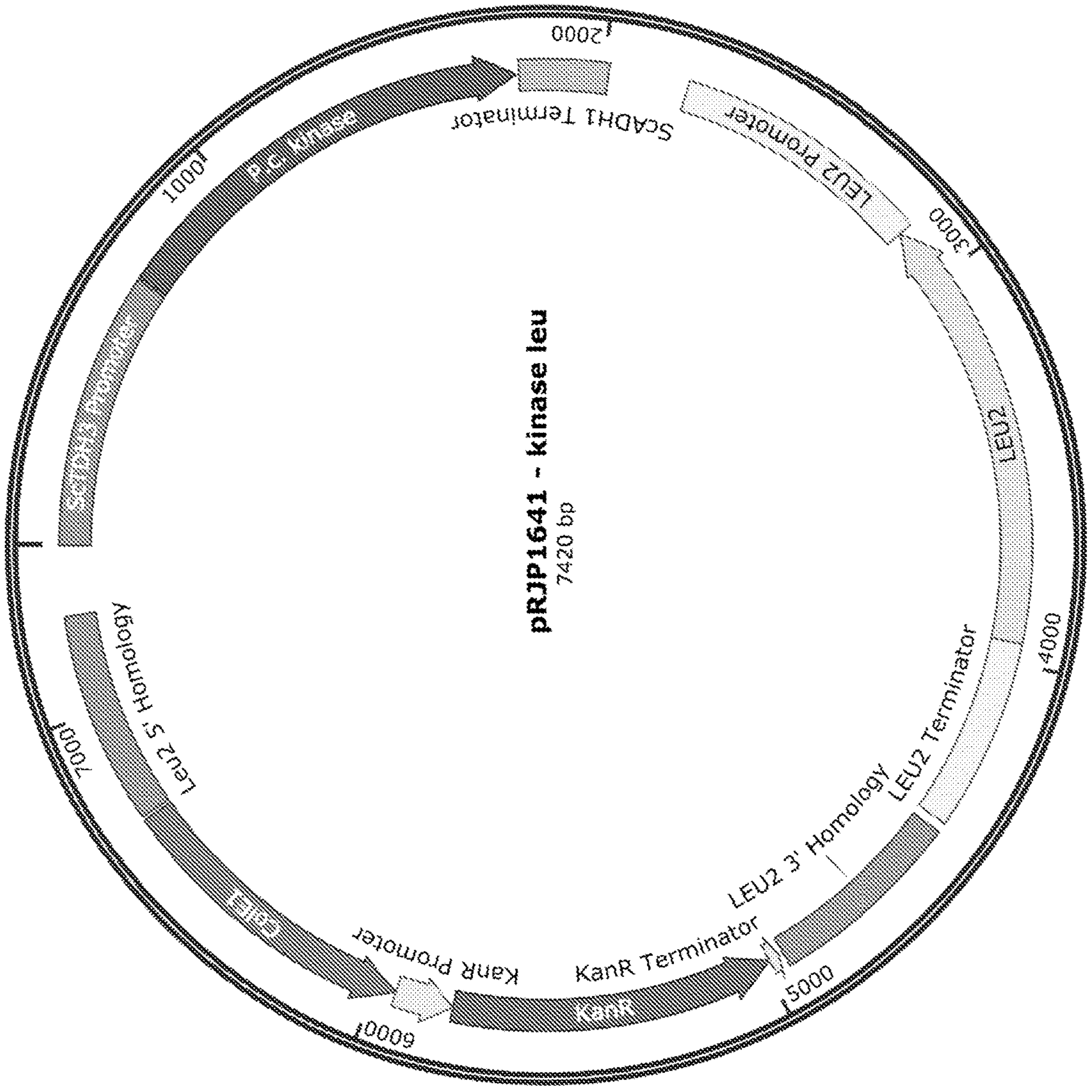
FIG. 15 depicts a non-limiting example of a plasmid map for the overexpression of 4-hydroxytryptamine kinase (e.g., SEQ ID NO: 41) in yeast in accordance with embodiments of the disclosure.

Example 5. Production of Tryptamine Derivatives from Fed Tryptamines Using Engineered Cells Microbes can be genetically modified to express metabolic enzymes capable of derivatizing tryptamines. Hydroxyl and phosphoryloxy substitutions to indole positions of tryptamines was investigated by expressing heterologous enzymes in yeast and feeding tryptamines with various amine substitutions. A single gene expression plasmid with CEN6/ARS4 replication sequences, URA3 expression cassette, and kanamycin resistance was cloned to contain a coding sequence for tryptamine 4-hydroxylase from *P. cyanescens* (SEQ ID NO: 33) and was named pRJP1639 (FIG. 13). A single gene expression plasmid with CEN6/ARS4 replication sequences, URA3 expression cassette, and kanamycin resistance was cloned to contain a coding sequence for tryptamine 5-hydroxylase from *S. mansoni* (SEQ ID NO: 47) and was named pRJP1640 (FIG. 14). A single gene expression plasmid with CEN6/ARS4 replication sequences, LEU2 expression cassette, and kanamycin resistance was cloned to contain a coding sequence for 4-hydroxytryptamine kinase from *P. cubensis* (SEQ ID NO: 41) and was named pRJP1641 (FIG. 15).

*S. cerevisiae* strain BY4741 (MATa his3Δ1 leu2Δ0 met15Δ0 ura3Δ0) was used for experiments in this study and was propagated at 30° C. The pRJP1639 plasmid was transformed into BY4741 by lithium acetate protocol and selected for on synthetic complete medium lacking uracil. The resulting strain, yNAB003, was isolated and genotyped. The pRJP1640 plasmid was transformed into BY4741 by lithium acetate protocol and selected for on synthetic complete medium lacking uracil. The resulting strain, yNAB004, was isolated and genotyped. The plasmid pRJP1641 was linearized by NotI digestion and transformed into strain yNAB003 by lithium acetate protocol and selected for on synthetic complete medium lacking leucine. The resulting strain, yNAB005, was isolated and genotyped.

Overnight grown cultures of yNAB003, yNAB004, and yNAB005 were used to inoculate 250 mL cultures of synthetic complete medium and were grown at 30° C. in a rotary shaker at 225 rpm. Cultures were concentrated into 25 mL of synthetic complete medium lacking uracil and transferred to 5 mL culture tubes. 5 mM of various tryptamines (including 5-methoxy-N,N-dimethyltryptamine, N,N-diisopropyltryptamine, N-methyl-N-isopropyltryptamine, N,N-dimethyltryptamine, N,N-tetramethylenetryptamine, and N,N-dipropyltryptamine) were added to separate tubes (FIG. 16). After 3 days of incubation at 30° C., media from cultures were sampled by centrifuging 1 mL of culture at 18000 rpm and transferring clarified media to sample vials. Analysis was performed by chromatography/mass spectrometry (LCMS) with a 1260 Infinity LC System connected to a 6120 Quadrupole Mass Spectrometer (Agilent Technologies). Zorbax Eclipse Plus C18 guard column (4.6 cm×12.5 cm, 5 μm packing, Agilent Technologies) was connected to a Zorbax Eclipse Plus C18 column (4.6 mm×100 mm, 3.5 μm packing, Agilent Technologies) at 20° C. using a 0.5 mL/min flow rate. Water and acetonitrile mobile phases contained 0.1% formic acid as the pH modifier. The elution gradient (water:acetonitrile volume ratio) was as follows: 98:2 (0-2 min), linear ramp from 98:2 to 5:95 (2-17 min), 5:95 (17-22 min), linear ramp from 5:95 to 98:2 (22-23 min), and 98:2 (23-28 min). Absorbance was measured using a diode array detector for UV-Vis analysis. MS was conducted in atmospheric pressure ionization-positive electrospray (API-ES positive) mode at 100-V fragmentor voltage with ion detection set to both full scanning mode (50-1200 m/z). Detection of tryptamines was conducted by extraction of ion masses of corresponding tryptamine not found in the unfed control sample or the original tryptamine chemical stock. 4-hydroxy derivatives of fed tryptamines were identified for the yNAB003 culture. 5-hydroxy derivatives of fed tryptamines were identified for the yNAB004 culture. Ion masses for 4-hydroxy-N,N-dipropyltryptamine and 4-phosphoryloxy-N,N-dipropyltryptamine were identified in the yNAB005 culture media fed with N,N-dipropyltryptamine (see FIG. 16).

Example 6. Colorimetric Screening for High Hydroxylation Activity

Figure 17:
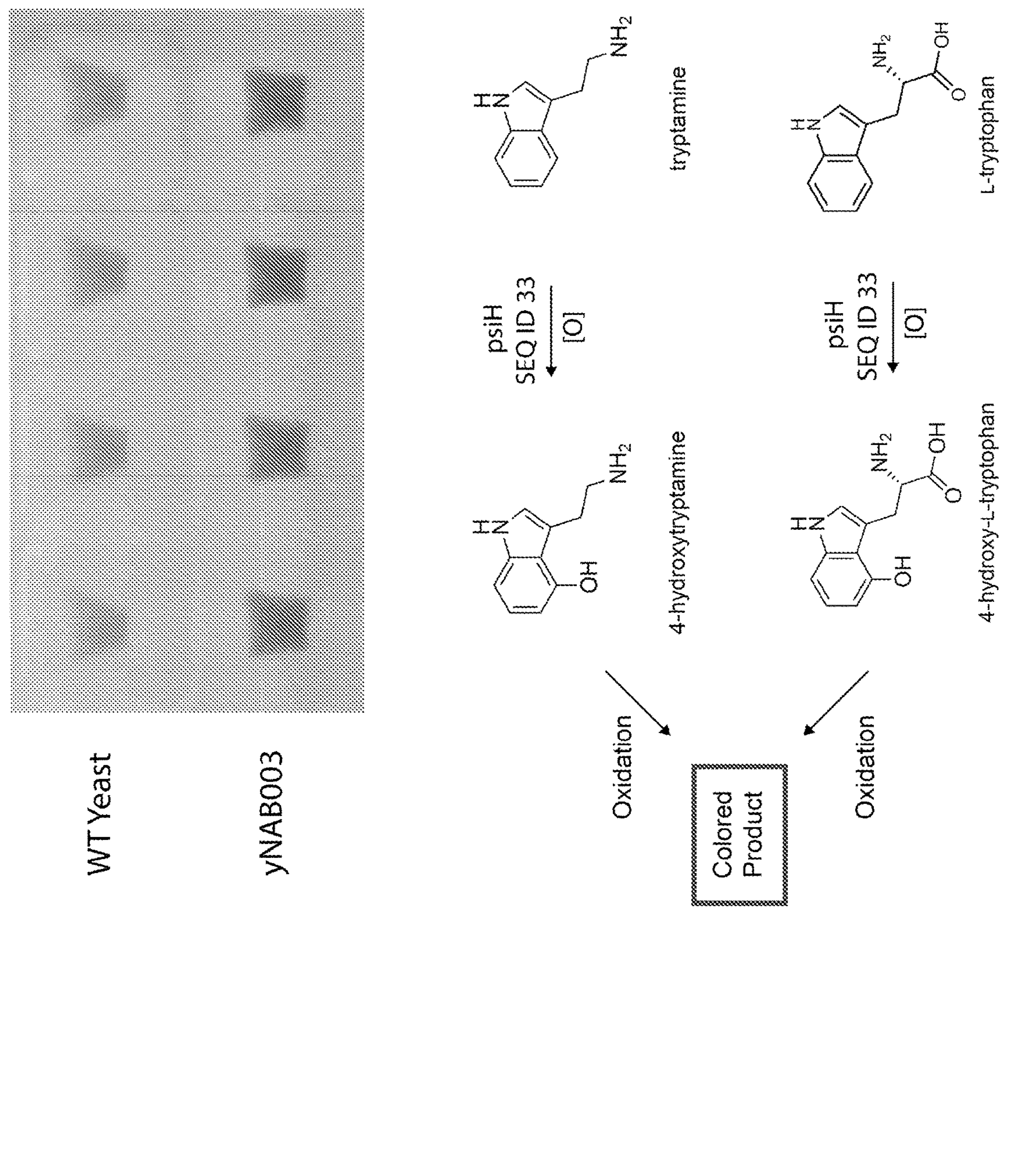
FIG. 17 depicts a non-limiting example of a colorimetric screening assay as an indicator of hydroxylase activity in yeast in accordance with embodiments of the disclosure.

Without addition of a protecting group at the hydroxyl position of 4-hydroxy-tryptamine and 4-hydroxytryptophan, the compounds will oxidize to a colored compound. Accordingly, subsequent hydroxylase and oxidation activity on tryptamine and tryptophan can be used as an indicator of hydroxylase activity. To demonstrate this activity, color formation of the strain yNAB003 with high tryptamine 4-hydroxylase from *P. cyanescens* (SEQ ID NO: 33) was compared to activity of WT BY4741. Four separate 3 mL cultures were started for WT BY4741 and yNAB003 for 3 days at 30° C. in synthetic complete media with 4 mM added tryptamine at 750 rpm of high frequency shaking. After culturing, these cultures were centrifuged to pellet the cells for observation of pigment formation. The formation of blue product was observed in the yNAB003 cultures as an indication of tryptamine 4-hydroxylase activity and was not observed in the WT BY4741 cultures (FIG. 17).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of synthesizing a tryptamine derivative from a substituted tryptamine, the method comprising cultivating an engineered microbial cell comprising one or more nucleic acid sequences encoding one or more of:

(i) a tryptamine 4-hydroxylase comprising an amino acid sequence having at least 80% sequence identity to any one of SEQ ID NOS: 32-35;

(ii) a tryptamine 5-hydroxylase comprising an amino acid sequence having at least 80% sequence identity to SEQ ID NO: 47;

(iii) a kinase comprising an amino acid sequence having at least 80% sequence identity to any one of SEQ ID NOS: 41-44;

(iv) a P450 reductase comprising an amino acid sequence having at least 80% sequence identity to any one of SEQ ID NOS: 36-40; and (v) a transferase comprising an amino acid sequence having at least 80% sequence identity to any one of SEQ ID NOS: 21-31 or 46, in the presence of a substituted tryptamine to produce the tryptamine derivative, wherein:

a) the substituted tryptamine comprises tryptamine, 5-hydroxytryptamine, or 5-phosphoryloxytryptamine, and the tryptamine derivative is:

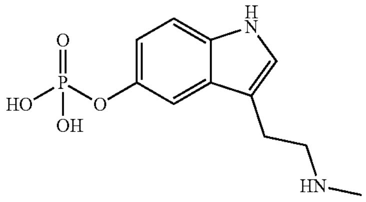 [SMILES: CNCCc1c[nH]c2ccc(OP(=O)(O)O)cc12]

(5-phosphoryloxy-N-methyltryptamine);

b) the substituted tryptamine comprises N,N-dipropyltryptamine or 4-hydroxy-N,N-dipropyltryptamine and the tryptamine derivative is:

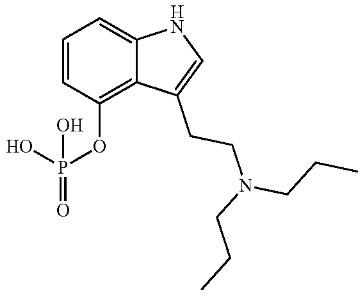 [SMILES: CCCN(CCC)CCc1c[nH]c2cccc(OP(=O)(O)O)c12]

(4-phosphoryloxy-N,N-dipropyltryptamine);

c) the substituted tryptamine comprises N,N-dipropyltryptamine or 5-hydroxy-N,N-dipropyltryptamine and the tryptamine derivative is:

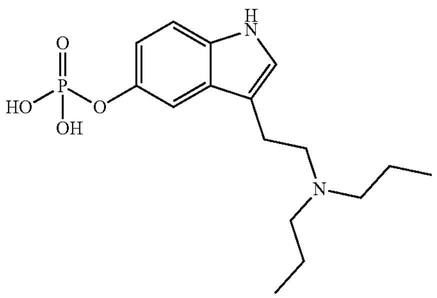 [SMILES: CCCN(CCC)CCc1c[nH]c2ccc(OP(=O)(O)O)cc12]

(5-phosphoryloxy-N,N-dipropyltryptamine);

d) the substituted tryptamine comprises 7-hydroxytryptamine or 7-phosphoryloxytryptamine, and the tryptamine derivative is:

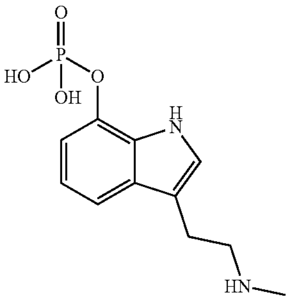 [SMILES: CNCCc1c[nH]c2c(OP(=O)(O)O)cccc12]

(7-phosphoryloxy-N-methyltryptamine);

e) the substituted tryptamine comprises ibogamine or 4-hydroxyibogamine, and the tryptamine derivative is:

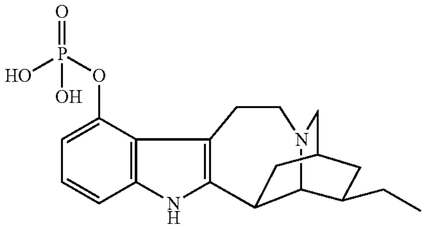 [SMILES: CCC1CC2CC3c4[nH]c5cccc(OP(=O)(O)O)c5c4CCN(C2)C13]

(4-phosphoryloxyibogamine) or

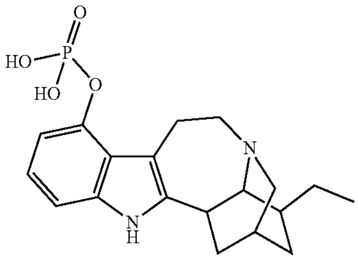 [SMILES: CCC1CC2CC3c4[nH]c5cccc(OP(=O)(O)O)c5c4CCN(C2)C13]

(4-phosphoryloxyibogamine);

f) the substituted tryptamine comprises ibogamine or 4-hydroxyibogamine, and the tryptamine derivative is:

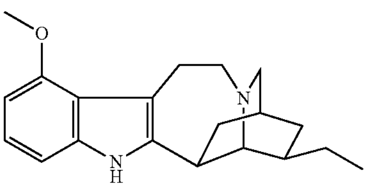 [SMILES: CCC1CC2CC3c4[nH]c5cccc(OC)c5c4CCN(C2)C13]

(4-methoxyibogamine);

g) the substituted tryptamine comprises ibogamine and the tryptamine derivative is:

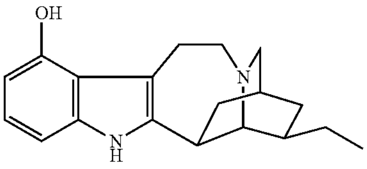 [SMILES: CCC1CC2CC3c4[nH]c5cccc(O)c5c4CCN(C2)C13]

(4-hydroxyibogamine) or

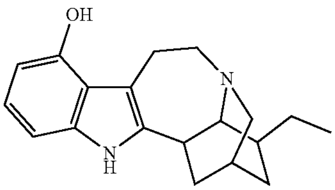 [SMILES: CCC1CC2CC3c4[nH]c5cccc(O)c5c4CCN(C2)C13]

(4-hydroxyibogamine);

h) the substituted tryptamine comprises tryptamine, 4-hydroxytryptamine, 4-methoxytryptamine, 5-hydroxytryptamine, 5-methoxytryptamine, N,N-dimethyltryptamine, 4-hydroxy-N,N-dimethyltryptamine, 5-hydroxy-N,N-dimethyltryptamine, or 5-methoxy-N, N-dimethyltryptamine, and the tryptamine derivative is:

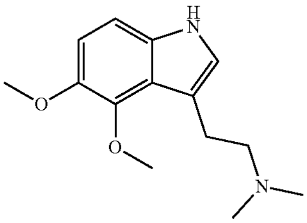

(4,5-dimethoxy-N,N-dimethyltryptamine); or i) the substituted tryptamine comprises tryptamine, 4-hydroxytryptamine, or N-acetyltryptamine, and the tryptamine derivative is:

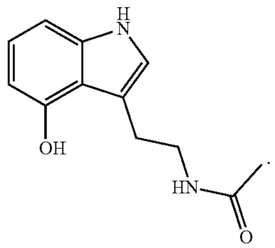 [SMILES: CC(=O)NCCc1c[nH]c2cccc(O)c12]

2. The method of claim 1, wherein the engineered microbial cell is a eukaryotic cell.

3. The method of claim 2, wherein the eukaryotic cell is a yeast cell.

4. The method of claim 3, wherein the yeast cell is of the species *Saccharomyces cerevisiae.*

5. The method of claim 1, wherein the engineered microbial cell is a prokaryotic cell.

6. The method of claim 5, wherein the prokaryotic cell is a bacterial cell.

7. The method of claim 6, wherein the bacterial cell is of the species *Escherichia coli* or *Corynebacterium glutamicum*.

8. The method of claim 1, wherein the substituted tryptamine is produced biosynthetically by the engineered microbial cell.

9. The method of claim 1, wherein the engineered microbial cell secretes the tryptamine derivative into a culture broth.

10. The method of claim 1, wherein the engineered microbial cell is a lysate of the engineered microbial cell.

11. The method of claim 1, wherein the substituted tryptamine is fed to the engineered microbial cell.

* * * * *